(12) United States Patent
Davis et al.

(10) Patent No.: US 6,239,259 B1
(45) Date of Patent: May 29, 2001

(54) MULTIVALENT AND MULTISPECIFIC ANTIGEN-BINDING PROTEIN

(75) Inventors: Paul J. Davis, Bedford; Cornelis P. Logt van der; Martine E. Verhoeyen, both of Northampton, all of (GB)

(73) Assignee: Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/171,025

(22) PCT Filed: Mar. 26, 1997

(86) PCT No.: PCT/EP97/01609

§ 371 Date: Dec. 28, 1998

§ 102(e) Date: Dec. 28, 1998

(87) PCT Pub. No.: WO97/38102

PCT Pub. Date: Oct. 16, 1997

(30) Foreign Application Priority Data

Apr. 4, 1996 (EP) .................................................. 96302412

(51) Int. Cl.⁷ ............................. C07K 16/00; C07K 1/00; C12P 21/08; A61K 39/395; G01N 33/53
(52) U.S. Cl. .................. 530/387.3; 530/350; 530/387.1; 530/402; 530/808; 424/136.1; 424/134.1; 424/133.1; 435/69.1; 435/7.1
(58) Field of Search .............................. 530/350, 387.1, 530/402, 808, 387.3; 424/136.1, 133.1, 134.1; 435/7.1, 69.6

(56) References Cited

U.S. PATENT DOCUMENTS 4,946,778 * 8/1990 Ladner et al. ....................... 435/69.6
5,132,405 * 7/1992 Huston et al. ...................... 530/387.3

FOREIGN PATENT DOCUMENTS

| 93 11161 | 6/1993 | (WO) . |
| 94 09131 | 4/1994 | (WO) . |
| 94 13804 | 6/1994 | (WO) . |
| 94 13806 | 6/1994 | (WO) . |
| 97 14719 | 4/1997 | (WO) . |

OTHER PUBLICATIONS

Pei et al. Proc. Natl. Acad. Sci. 94: 9637–9642, Sep. 1997.*
Tutt et al. J. Immunol. 147: 60–69, 1991.*
Jung et al. Eur. J. Immunol. 21: 2431–2435, 1991.*
P. Holliger et al: "Diabodies": Small bivalent and bispecific antibody fragments—Proceedings of the National Academy of Sciences of the USA, vol. 90 No. 14, Jul. 15, 1993, pp. 6444–6448, XP002014058.

* cited by examiner

Primary Examiner—Lynette R. F. Smith
Assistant Examiner—S. Devi
(74) Attorney, Agent, or Firm—Pillsbury Madison & Sutro LLP

(57) ABSTRACT

A multivalent antigen-binding protein comprises a first polypeptide comprising, in series, three or more variable domains of an antibody heavy chain and a second polypeptide comprising, in series, three of more variable domains of an antibody light chain, said first and second polypeptides being linked by association of the respective heavy chain and light chain variable domains, each associated variable domain pair forming an antigen binding site. Methods for their production and uses thereof, in particular for therapeutic and diagnostic applications, are disclosed.

11 Claims, 50 Drawing Sheets

FIG. 1B
E
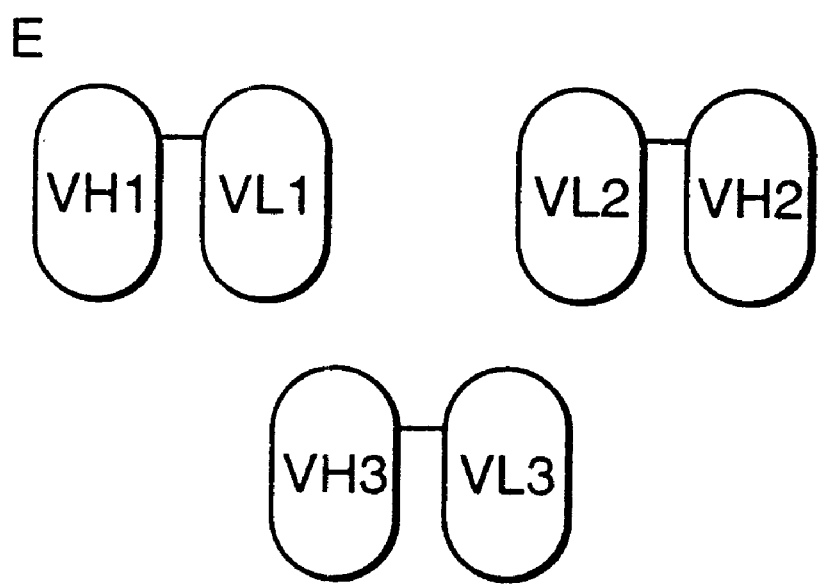
F
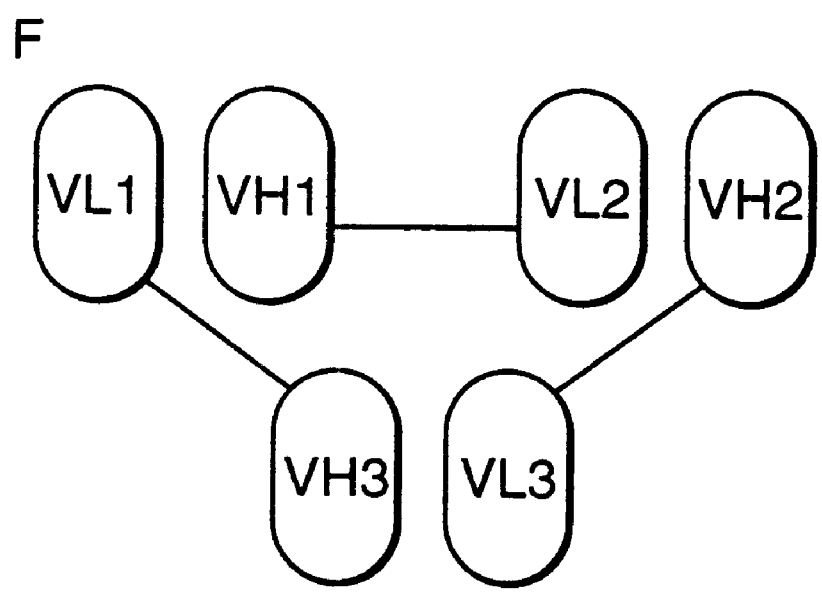

FIG. 2A1

```
                    M  K  Y  L  L  P  T
       AAGCTTGCATGCAAATTCTATTTCAAGGAGACAGTCATAATGAAATACCTATTGCCTACG pelB   A  A  A  G  L  L  L  L  A  A  Q  P  A  M  A  Q  V  Q  L  Q
leader GCAGCCGCTGGATTGTTATTACTCGCTGCCAACCAGCGATGGCCCAGGTGCAGCTGCAG E  S  G  Q  L  V  K  P  G  G  Q  L  T  L  S  C  A  T  S
       GAGTCAGGGGAGACTTAGTGAAGCCTGGAGGGTCCCTGACACTCTCCTGTGCAACCTCT G  F  T  F  S  S  Y  A  F  S  W  V  R  Q  T  S  D  K  S  L
       GGATTCACTTTCAGTAGTTATGCCTTTTCTTGGGTCCGCCAGACTTCAGACAAGAGTCTG E  W  V  A  T  I  S  S  T  D  T  Y  T  Y  Y  S  D  N  V  K
       GAGTGGGTCGCAACCATCAGTAGTACTGATACTTATACCTATTATTCAGACAATGTGAAG VH4715 G  R  F  T  I  S  R  D  N  G  K  N  T  L  Y  L  Q  M  S  S
       GGGCGCTTCACCATCTCCAGAGACAATGGCAAGAACACCCTGTACCTGCAAATGAGCAGT L  K  S  E  D  T  A  V  Y  Y  C  A  R  H  G  Y  Y  G  K  G
       CTGAAGTCTGAGGACACAGCCGTGTATTACTGTGCAAGACATGGGTACTATGGTAAAGGC
```

```
T  S  E  D  S  A  V  Y  Y  C  G  R  R  F  D  Y  W  G  Q  G
ACCTCTGAGGACTCTGCGGTCTATTACTGTTCAAGACGCTTTGACTACTGGGGCCAAGGG

T  T  V  T  V  S  S
ACCACCGTCACCGTCTCCTCAATAAGCTAGGGAGCTGCATGCAAATTCTATTTCAAG

M  K  Y  L  L  P  T  A  A  A  G  L  L  L  L  A
pelB   GAGACAGTCATATGAAATACCTATTGCCTACGGCAGCCGCTGGATTGTTATTACTCGCT
leader A  Q  P  A  M  A  D  I  E  L  T  Q  S  P  S  S  M  Y  A  S
GCCCAACCAGCGATGGCCGACATCGAGCTCACCCAGTCTCCATCTTCCATGTATGCATCT L  G  E  R  I  T  I  T  C  K  A  S  Q  D  I  N  T  Y  L  T
CTAGGAGAGAGAATCACTATCACTTGCAAGGCGAGTCAGGACATTAATACCTATTTAACC W  F  Q  Q  K  P  G  K  P  K  T  L  I  Y  R  A  N  R  L
VL3418  TGGTTCCAGCAGAAACCAGGGAAATCTCCCAAGACCCTGATCTATCGTGCAAACAGATTG
```

FIG. 2BI

```
L  D  G  V  P  S  R  F  S  G  S  G  S  G  Q  D  Y  S  L  T
CTAGATGGGTCCCATCAGGTTCAGTGGCAGTGGATCTGGGACAAGATTATTCTCACC

I  S  S  D  Y  H  D  M  G  I  Y  Y  C  L  Q  Y  D  E  F
ATCAGCAGCCTGGACTATGAAGATATGGGAATTTATTATTGTCTACAATATGATGAGTTG

K  T  F  G  Q  G  T  K  L  E  I  K  R  G  G  G  G  S  G  G
TACACGTTCGGAGGGGGGACCAAGCTCGAGATCAAACGGGGTGGAGGCGGTTCAGGCGGA

G  G  S  G  G  G  G  V  D  I  E  L  T  Q  S  P  P  S  L
GGTGGCTCTGGCGGTGGCGGAGTCGACATCGAACTCACTCAGTCTCCATTCTCCCTGACT

V  T  A  G  E  K  V  T  M  M  C  K  X  S  Q  T  L  M  N  S
GTGACAGCAGGAGAGAAGGTCACTATGAATTGCAAGTCCGGTCAGAGTCTGTTAAACAGT
```

Linker

```
V  N  Q  R  N  Y  L  T  W  Y  Q  Q  K  P  G  Q  P  P  K  L
GTAAATCAGAGAGGAACTACTTGACCTGGTACCAGCAGAAGCCAGGCCAGCCTCCTAAACTG

L  I  Y  W  A  S  T  R  E  S  G  V  P  D  R  F  T  A  S  G
TTGATCTACTGGGCATCCACTAGGGAATCTGGAGTCCCTGATCGCTTCACAGCCAGTGGA

S  G  T  D  F  T  L  T  I  S  S  V  Q  A  E  D  L  A  V  Y
TCTGGAACAGATTTCACTCTCACCATCAGCAGTGTGCAGGCTGAAGACCTGGCAGTTTAT

Y  C  Q  N  D  Y  T  Y  P  F  T  F  G  G  G  T  K  L  E  I
TACTGTCAGAATGATTATACTTATCCGTTCACGTTCGGAGGGGGGACCAAGCTCGAAATC
```

Hydro-11 tag
```
K  R  G  S  G  S  G  N  S  G  K  G  Y  L  K
AAACGGGGATCCGGTAGCGGGAACTCCGGTAAGGGGTACCTGAAGTAATAAGCGGCCGCG
```

AATTC

FIG. 3A1

```
                    M  K  Y  L  L  P  T
AAGCTTGCATGCAAATTCTATTTCAAGGAGACAGTCATAATGAAATACCTATTGCCTACG pelB    A  A  A  G  L  L  L  L  A  A  Q  P  A  M  A   Q  V  Q  L  Q
leader  GCAGCCGCTGGATTGTTATTACTCGCTGCCCAACCAGCGATGGCCCAGGTGCAGCTGCAG E  S  G  P  G  L  V  A  P  S  Q  S  L  S  I  T  C  T  V  S
        GAGTCAGGACCTGGCCTGGTGGCCCCTCACAGAGCCTGTCCATCACATGCACCGTCTCA G  F  S  L  T  G  Y  G  V  N  W  V  R  Q  P  P  G  K  G  L
        GGGTTCTCATTAACCGGCTATGGTGTAAACTGGGTTCGCCAGCCTCCAGGAAAGGGTCTG E  W  L  G  M  I  W  G  D  G  N  T  D  Y  N  S  A  L  K  S
        GAGTGGCTGGGAATGATTTGGGGTGATGGAAACACAGACTATAATTCAGCTCTCAAATCC
```

FIG. 3A2

VHlys

R L S I S K D N S K S Q V F L K M N S L
AGACTGAGCATCAGCAAGGACAACTCCAAGAGCCAAGTTTCTTAAAAATGAACAGTCTG

H T D D T A R Y Y C A R E R D Y R L D Y
CACACTGATGACACAGCCAGGTACTACTGTGCCAGAGAGAGATTATAGGCTTGACTAC

W G H G T T V T V S S | G G G G S G G G G
TGGGGCGAAGGCACCACCGTCACCGTCTCCTCAGGTGGAGGCGGTTCAGGCGGAGGTGGC

Linker | S G G G G S | D I E L T Q S P A S L A S
TCTGGCGGTGGCGGATCGGACATCGAGCTCACCCAGTCTCCAGCCTCCCTTTCTGCGTCT V G E T V T I T C R A S G N I R N Y L A
GTGGGAGAAACTGTCACCATCACATGTCGAGCAAGTGGGAATATTCACAATTATTTAGCA

FIG. 3A3

VLlys

```
W  Y  Q  Q  K  Q  G  K  S  P  Q  L  L  V  Y  Y  T  T  L
TGGTATCAGCAGAAACAGGGAAATCTCCTCAGCTCCTGGTCTATTATACAACCTTA

A  D  G  V  P  S  R  F  S  G  S  G  S  G  T  Q  Y  S  L  K
GCAGATGGTGTGCCATCAAGGTTCAGTGGCAGTGGATCAGGAACACAATATTCTCTCAAG

H  N  S  H  Q  P  E  D  F  G  S  Y  Y  C  Q  H  F  W  S  T
ATCAACAGCCTGCAACCTGAAGATTTTTGGAGTTATTACTGTCAACATTTTTGGAGTACT

P  R  T  P  G  G  G  T  K  L  E  I  K  R     E  Q  K  L  I  S
CCTCGGACGTTCGGTGGAGGCACCAAGCTCGAGATCAAACGGGAACAAAAACTCATCTCA
```

Myc-tag
```
E  E  D  L  N
GAAGAGGATCTGAATTAATAAGATCAAATAAGGATCCAGCTCGAATTC
```

FIG. 3BI

```
                        M   K   Y   L   L   P   T
          AAGCTTGCATGCAAATTCTATTTCAAGGAGACAGTCATAATGAAATACCTATTGCCTACG pelB      A   A   A   G   L   L   L   L   A   A   Q   P   A   M   A   Q   V   Q   L   Q
leader    GCAGCCGCTGCTGGATTGTTATTACTCGCTGCCCAACCAGCGATGGCCCAGGTGCAGCTGCAG E   S   G   G   G   D   L   V   K   P   G   G   S   L   T   L   S   C   A   T   S
          GAGTCAGGGGGAGACTTAGTGAAGCCTGGAGGGTCCCTGACACTCTCCTGTGCAACCTCT G   F   T   F   S   S   Y   A   F   S   W   V   R   Q   T   S   D   K   S   L
          GGATTCACTTTCAGTAGTTATGCCTTTTCTTGGGTCCGCCAGACTTCAGACAAGAGTCTG E   W   V   A   T   I   S   T   D   T   Y   T   Y   Y   S   D   N   V   K
          GAGTGGGTCGCAACCATCAGTACTGATACTTATACCTATTATTCAGACAATGTGAAG
```

FIG. 3B2

```
VH4715  G  R  F  T  I  S  R  D  N  G  K  N  T  L  Y  L  Q  M  S
        GGGCGCTTCACCATCTCCAGAGACAATGGGCAAGAACACCCTGTACCTGCAAATGAGCAGT

L  K  E  D  T  A  V  Y  Y  C  A  R  H  G  Y  Y  G  K  G
        CTGAAGTCTGAGGACACAGCCGTGTATTACTGTGCAAGACATGGGTACTATGGTAAAGGC

Y  F  D  Y  W  G  Q  G  T  T  V  T  V  S  S    G  G  G  S
        TATTTTGACTACTGGGGCCAAGGGACCACGGTCACCGTCTCCTCAGGTGGAGGCGGTTCA

Linker  G  G  G  G  S  G  G  G  G  S   D  I  E  L  T  Q  S  P  S
        GGCGGGAGGTGGCGGTTCTGGCGGTGGCGGATCGGACATCGAGCTCACTCAGTCTCCATTCTCC L  T  V  T  A  G  E  K  V  T  M  N  C  K  S  G  Q  S  L  L
        CTGACTGTGACAGCAGGAGAGAAGGTCACTATGAATTGCAAGTCCGGTCAGAGTCTGTTA
```

```
 N  S  V  N  Q  R  N  Y  L  T  W  Y  Q  Q  K  P  G  Q  P  P
AACAGTGTAAATCAGAGGAACTACTTGACCTGGTACCAGCAGAAGCCAGGGCAGCCTCCT

K  L  L  I  Y  W  A  S  T  R  E  S  S  G  V  P  D  R  F  T  A
AAACTGTTGATCTACTGGGCATCCACTAGGGAATCTTCTGGAGTCCCTGATCGCTTCACAGCC

S  G  S  G  T  D  F  T  L  T  I  S  S  V  Q  A  E  D  L  A
AGTGGATCTGGAACAGATTTCACTCTCACCATCAGCAGTGTGCAGGCTGAAGACCTGGCA

V  Y  Y  C  Q  N  D  Y  T  Y  P  F  T  F  G  Q  T  K  L
GTTTATTACTGTCAGAATGATTATACTTATCCGTTCACGTTCGGAGGGGGACCAAGCTC
```

Hydro2-tag
```
 E  I  K  R  G  S  G  G  N  S  G  K  G  Y  L  K
GAGATCAAACGGGATCCGGTAGCGGGAACTCCGGTAAGGGGTACCTGAAGTAATAAGAT

CAAACGGTAATAAGGATXXAGCTCGAATTC
```

EXON 1 cc|ATGGGATGGAGCTGTATCATCCTCTTCTTGGTAGCAACAGCTACAG|gt
  | M  G  W  S  C  I  I  L  F  L  V  A  T  A  T | aaggggctcacagtagcaggcttgaggtctggacatatatatgggtgaca atgacatccactttgcctttctctccacag|GTGTCCACTCCC|AGGTCCAA
                               | G  V  H  S |Q  V  Q
                                             EXON 2

|CTGCAG|
| L  Q |

FIG. 9A

| M. | 1 | 2 | 3 | 4 |

40 kDa -
30 kDa -

←VL3-HII

FIG. 9B

| M. | 1 | 2 | 3 | 4 |

40 kDa -
30 kDa -

←VH3
←VL3-HII

FIG. 12A

```
       D  I  E  L  T  Q  S  P  A  S  L  S  A  S  V  G  E
GAATTCGGCCGACATCGAGCTCACCCAGTCTCCAGCCTCCCTTTCTGCTGTGTGGGAGA

T  V  T  I  T  C  R  A  S  G  N  I  H  N  Y  L  A  W  Y  Q
AACTGTCACCATCACACATGTCGAGCAAGTGGGAATATTCACAATTATTAGCATGGTATCA

Q  K  Q  G  K  S  P  Q  L  L  V  Y  Y  T  T  T  L  A  D
GCAGAAACAGGGAAATCTCCTCAGCTCCTGGTCTATTATACAACAACCTTAGCAGATGG

V  P  S  R  F  S  G  S  G  S  G  T  Q  Y  S  L  K  I  N
TGTGCCATCAAGGTTCAGTGGCAGTGGATCAGGAACACAATATTCTCAAGATCAACAG

L  Q  P  E  D  F  G  S  Y  Y  C  H  R  W  S  T  P  R  T  F
CCTGCAACCTGAAGATTTTGGGAGTTATTACTGTCAACATTTTTGGAGTACTCCTCGGAC

G  G  G  T  K  L  E  I  K  R              G  G  G  S  G  G  G  S
GTTCGGGTGGAACCAAGCTCGAGATCAAACGGGGTGGAGGCGGTTCAGGCGGGAGGTGGCTC
```

VLLys

FIG. 12B

Linker

| G | G | G | G | S | Q | V | Q | L | Q | E | S | G | P | G | L | V | A | P | S |
|---|---|---|---|---|---|---|---|---|---|---|---|---|---|---|---|---|---|---|---|

TGGCGGTGGCTGGGATCGCAGGTGCAGCTGCAGGAGTCAGGACCTGGCCTGGTGGCGCCCTC

| Q | S | L | T | C | T | V | S | G | F | S | L | T | G | T | G | V | N |
|---|---|---|---|---|---|---|---|---|---|---|---|---|---|---|---|---|---|

ACAGAGCCTGTCCATCACATGCACCGTCTCAGGGTTCTCATTAACCGGCTATGGTGTAAA

| W | V | R | Q | P | P | G | K | G | L | E | W | L | G | M | I | W | G | D | G |
|---|---|---|---|---|---|---|---|---|---|---|---|---|---|---|---|---|---|---|---|

CTGGGTTCGCCAGCCTCCAGGAAAGGGTCTGGAGTGGCTGGGAATGATTTGGGGTGATGG

VHLys

| N | T | D | Y | N | S | A | L | K | S | R | L | S | I | S | K | D | N | S | K |
|---|---|---|---|---|---|---|---|---|---|---|---|---|---|---|---|---|---|---|---|

AAACACAGACTATAATTCAGTCTCTCAAATCCAGACTGAGCATCAGCAAGGACAACTCCAA

| S | Q | V | F | L | K | M | N | S | L | H | T | D | D | T | A | P | Y | Y | C |
|---|---|---|---|---|---|---|---|---|---|---|---|---|---|---|---|---|---|---|---|

GAGCCAAGTTTCTTAAAAATGAACAGTCTGCACACTGATGACACAGCCAGTACTACTG

| A | R | E | R | D | Y | R | L | D | Y | W | G | Q | G | T | T | V | T | V | S |
|---|---|---|---|---|---|---|---|---|---|---|---|---|---|---|---|---|---|---|---|

TGCCAGAGAGAGAGATTATAGGCTTGACTACTGGGGCCAAGGGACCACGGTCACCGTCTC

CTCATGATAAGCTT

FIG. 13A

```
pelB                                              M  K  Y  L  L  P  T  A
leader  AAGCTTGCAAATTCTATTTCAAGGAGACAGTCATAATGAAATACCTATTGCCTACGGCAG A  A  G  L  L  L  L  A  A  Q  P  A  M  A  Q  V  Q  L  Q  Q
        CCGCTGGATTGTTATTACTCGCTGCCCAACCAGCGATGGCCCAGGTGCAGCTGCAGCAGT S  G  P  E  L  V  K  P  G  A  S  V  K  M  S  C  K  A  S  G
        CAGGACCTGAGCTGGTAAAGCCTGGGGCTTCAGTGAAGATGTCCTGCAAGGCTTCTGGAT Y  T  F  T  S  Y  V  M  H  W  V  K  Q  K  P  G  Q  G  L  E
        ACACATTCACTAGCTATGTTATGCACTGGGTGAAACAGAAGCCTGGGCAGGGCCTTGAGT W  I  G  Y  I  Y  P  Y  N  D  G  T  K  Y  N  E  K  F  K  G
VH3418  GGATTGGATATATTTATCCTTACAATGATGGTACTAAGTACAATGAGAAGTTCAAGGCA
```

FIG. 13B

```
K  A  T  L  T  S  D  K  S  S  S  T  A  Y  M  E  L  S  S  L
AGGCCACACTGACTTCAGACAAATCCTCCAGCACAGCCTACATGGAGCTCAGCAGCCTGA

T  S  E  D  S  A  V  Y  Y  C  S  R  R  F  D  Y  W  G  Q  G
CCTCTGAGGACTCTGCGGTCTATTACTGTTCAAGACGCTTTGACTACTGGGGCCAAGGGA

T  T  V  T  V  S  S
CCACGGTCACCGTCTCCTCAATAATAAGAGCTTGCATGCAAATTCTATTTCA

M  K  Y  L  L  P  T  A  A  A  G  L  L  L  L
AGGAGACAGTCATAATGAAATACCTATTGCCTACGGCAGCCGCTGGATTGTTATTACTCG pelB    A  A  Q  P  A  M  A    D  I  E  L  T  Q  S  P  S  S  M  Y  A
leader  CTGCCCAACCAGCCATGGCCGACATCGAGCTCACCCAGTCTCCATCTTCCATGTATGCAT
```

FIG. 13C

```
S  L  G  E  R  I  T  C  K  A  S  Q  D  I  N  T  Y  L
CTCTAGGAGAGAATCACTTGCAAGGCGAGTCAGGACATTAATACCTATTTAA

T  W  F  Q  Q  K  P  G  K  S  P  K  T  L  I  Y  R  A  N  R
CCTGGTTCCAGCAGAAACCAGGGAAATCTCCCAAGACCCTGATCTATCGTGCAAACAGAT

VL3418  L  D  Q  V  P  S  R  F  S  G  S  G  Q  D  Y  S  L
         TGCTAGATGGGGTCCCATCAAGGTTCAGTGGCAGTGGATCTGGGCAAGATTATTCTCTCA

T  I  S  S  L  D  Y  E  D  M  G  I  Y  Y  C  L  Q  Y  D  E
CCATCAGCAGCCTGGACTATGAAGATATGGGAATTTATTATTGTCTACAATATGATGAGT

L  Y  T  F  G  G  G  T  K  L  E  I  K  R
TGTACACGTTCGGAGGGGGACCAAGCTCGAGATCAAACGGTAATAATGATCAAACGGT

ATAAGGATCCAGCTCGAATTC
```

FIG. 14A pelB leader

```
                          M  K  Y  L  L  P  T
AAGCTTGCATGCAAATTCTATTTCAAGGAGACAGTCATAATGAAATACCTATTGCCTACG

A  A  A  G  L  L  L  L  A  A  Q  P  A  M  A   Q  V  Q  L  Q
GCAGCCGCTGGATTGTTATTACTCGCTGCCCAACCAGCGATGGCCCAGGTGCAGCTGCAG

E  S  G  Q  S  L  T  L  S  C  A  T  S
GAGTCAGGGGAGACTTAGTGAAGCCTGGAGGGTCCCTGACACTCTCCTGTGCAACCTCT

G  F  T  F  S  S  Y  A  F  S  W  V  R  Q  T  S  D  K  S  L
GGATTCACTTTCAGTAGTTATGCCTTTTCTTGGGTCCGCCAGACCTCAGACAAGAGTCTG

E  W  V  A  T  I  S  S  T  D  T  Y  T  Y  Y  S  D  N  V  K
GAGTGGGTCGCAACCATTAGCAGTAGTACTGATACTTATACCTATTATTCAGACAATGTGAAG
```

```
Q  R  F  T  I  S  R  D  N  Q  K  N  T  L  Y  L  Q  M  S  S
GGGGCGCTTCACCATCTCCAGAGACAATCAGAAGAACACCCTGTACCTGCAAATGAGCAGT

L  K  E  D  T  A  V  Y  Y  C  A  R  R  G  Y  Y  G  K  G
CTGAAAGTCTGAGGACACAGCCGTGTATTACTGTGCAAGACATGGGTACTATGGTAAAGGC

Y  F  D  Y  W  G  Q  G  T  T  V  T  V  S  S
TATTTTGACTACTGGGGCCAAGGGACCACGGTCACCGTCTCCTCATAATAAGAGCTATGG

M  K  Y  L  L  P  T
GAGCTTGCATGCAAATTCTATTTCAAGGAGACAGTCATAATGAAATACCTATTGCCTACG pelB
leader  A  A  A  G  L  L  L  L  A  A  Q  P  A  M  A   D  I  E  L  T
        GCAGCCGCTGGATTGTTATTACTCGCTGCCCAACCAGCCATGGCCGACATCGAGCTCACT
```

FIG. 14C

Q S P F S L T V T A Q E K V T M N C K Q
CAGTCTCCATTCTCCCTGACTGTGACAGCAGGAGAAGGTCACTATGAATTGCAAGTCC

G Q S L L N S V N Q R N Y L T W Y Q Q R
GGTCAGAGTCTGTTAAACAGTGTAAATCAGAGGAACTACTTGACCTGGTACCAGCAGAAG

P G Q P P K L L I Y N A S T R E S G V P
CCAGGGCAGCCCTCCTAAACTGTTGATCTACTAGGGCATCCACTAGGGAATCTGGAGTCCCT

D R F T A S G S G T D F F L T I S S V Q
GATCGCTTCACAGCCAGTGGATCTGGAACAGATTTCACTCTCACCATCAGCAGTGTGCAG

A E D L A V Y Y C Q N D Y T Y P F T F G
GCTGAAGACCTGGCAGTTTATTACTGTCAGAATGATTATACTTATCCGTTCACGTTCGGA

VL4715

G G T K L E I K R  E Q K L I S E E D L N
GGGGGGACCAAGCTCGAGATCAAACGGGAACAAAAACTCATCTCAGAGAGGATCTGAAT
Myc-tag

TAATAAGATCAAACGGTAATAAGGATCCAGCTCGAATTC

FIG. 15A pelB leader

```
                              M  K  Y  L  L  P  T
AAGCTTGCATGCAAATTCTATTTCAAGGAGACAGTCATAATGAAATACCTATTGCCTACG

A  A  A  G  L  L  L  L  A  A  Q  P  A  M  A  |Q  V  Q  L  Q|
GCAGCCGCTGGATTGTTATTACTCGCTGCCCAACCAGCCGATGGCCCAGGTGCAGCTGCAG

|E  S  G  G  D  L  V  K  P  G  G  S  L  T  L  S  C  A  T  S|
GAGTCAGGGGGAGACTTAGTGAAGCCTGGAGGGTCCCTGACACTCTCCTGTGCAACCTCT

|G  F  T  F  S  Y  A  F  S  W  V  R  Q  T  S  D  K  S  L|
GGATTCACTTTCAGTAGTTATGCCTTTTCTTGGGTCCGCCAGACCTCAGACAAGAGTCTG

|E  W  V  A  T  I  S  T  D  T  Y  Y  S  D  N  V  K|
GAGTGGGTCGCAACCATCAGTACTGATACTTATTATTCAGACAATGTGAAG

|G  R  F  T  V  S  R  D  N  G  K  N  T  L  Y  L  Q  M  S|
GGGCGCTTCACCATCTCCAGAGACAATGGCAAGAACACCCTGTACCTGCAAATGAGCAGT
```

| L | K | S | D | T | A | V | Y | Y | C | A | R | H | G | Y | Y | G | K | G |
|---|---|---|---|---|---|---|---|---|---|---|---|---|---|---|---|---|---|---|

CTGAAGTCTGAGGACACAGCCGTGTATTACTGTGCAAGACATGGGTACTATGGTAAAGGC

| Y | F | D | Y | W | G | Q | G | T | V | T | V | S | S |
|---|---|---|---|---|---|---|---|---|---|---|---|---|---|

TATTTTGACTACTGGGGCCAAGGGACCGTCACCGTCTCCTCAGGTGGAGGCGGTTCA

Linker

| G | G | G | G | S | G | G | G | G | S |
|---|---|---|---|---|---|---|---|---|---|

GGCGGAGGTGGCTCTGGCGGTGGCGGATCGGA

| D | E | L | T | Q | S | P | F | S |
|---|---|---|---|---|---|---|---|---|

CATCGGA CGACATCGAGCTCACTCAGTCTCCATTCTCC

| L | T | V | T | A | E | K | V | T | M | N | C | K | S | S | Q | S | L | L |
|---|---|---|---|---|---|---|---|---|---|---|---|---|---|---|---|---|---|---|

CTGACTGTGACAGCAGAGAAGGTCACTATGAATTGCAAGTCCAGTCAGAGTCTGTTA

| N | S | V | N | Q | R | N | Y | L | T | W | Y | Q | Q | K | P | G | Q | P |
|---|---|---|---|---|---|---|---|---|---|---|---|---|---|---|---|---|---|---|

AACAGTGTAAATCAGAGAAACTACTTGACCTGGTACCAGCAGAAGCCAGGGCAGCCTCCT

K L L I Y W A S T R E S G V P D R F T A
AAACTGTTGATCTACTGGGCATCCACTAGGGAATCTGGAGTCCCTGATCGCTTCACAGCC

G S G T D F T L T I S S V Q A E D L A
AGTGGATCTGGAACAGATTTCACTCTCACCATCAGCAGTGTGCAGGCTGAAGACTTGGCA

V Y Y C Q N D Y T Y P F T F G G G T K L
GTTTATTACTGTCAGAATGATTATACTTATCCGTTCACGTTCGGAGGGGGACCAAGCTC

Myc-tag E I K R E Q K L I S E E D L N
GAGATCAAACGGGAACAAAAACTCATCTCAGAAGAGGATCTGAATTAATAAGATCAAACG

GTAATAAGGATCCAGCTCGAATTC

FIG. 16A1

```
                 M  K  Y  L  L  P  T
AAGCTTGCATGCAAATTCTATTTCAAGGAGACAGTCATAATGAAATACCTATTGCCTACG pelB   A  A  A  G  L  L  L  L  A  A  Q  P  A  M  A   Q  V  Q  L  Q
leader GCAGCCGCTGGATTGTTATTACTCGCTGCCCAACCAGCGATGGCCCAGGTGCAGCTGCAG E  S  G  G  G  D  L  V  K  P  G  E  S  L  K  L  S  C  A  T  S
       GAGTCAGGGGGAGACTTAGTGAAGCCTGGAGAGTCCCTGAAACTCTCCTGTGCAACCTCT G  F  T  F  S  Y  Y  A  F  S  W  V  R  Q  T  S  D  K  S  L
       GGATTCACTTTCAGTTATTATGCCTTTTCTTGGGTCCGCCAGACCTCAGACAAGAGTCTG E  W  V  A  T  I  S  S  T  D  T  Y  T  Y  Y  S  D  N  V  K
       GAGTGGGTTGCAACCATTAGTAGTACTGATACTTATACCTATTATTCAGACAATGTGAAG G  R  F  T  I  S  R  D  N  G  K  N  T  L  Y  L  Q  M  S
       GGGCGCTTCACCATCTCCAGAGACAATGGCAAGAACACCCTGTACCTGCAAATGAGCAGT VH4715 L  K  S  E  D  T  A  V  Y  Y  C  A  R  H  G  Y  Y  G  K  G
       CTGAAGTCTGAGGACACAGCCGTGTATTACTGTGCAAGACATGGGTACTATGGTAAAGGC
```

FIG. 16A2

Linker: G G G G S A
GGCGGAGGTGGCTCTGGCTCTGGCGGTGGCGGATCGGCC

K F D Y W G Q G T T V T V S S G G G G S
TATTTTGACTACTGGGGCCAAGGGACCACGGTCACCGTCTCCTCAGGTGGAGGCGGTTCA

Q V Q L Q Q
CAGGTCCAGCTGCAACAG

S G P E L V K P G A S V K M S C K A S
TCAGGACCTGAGCTGGTGAAGCCTGGGGCTTCAGTGAAGATGTCCTGCAAGGCTTCTGGA

G Y T F T S Y V M H W V K Q K P G Q G L E
TACACATTCACTAGCTATGTTATGCACTGGGTGAAACAGAAGCCTGGGCAGGGCCTTGAG

W I G Y I N P Y N D G T K Y N E K F K G
TGGATTGGATATATTAATCCTTACAATGATGGTACTAAGTACAATGAGAAGTTCAAAGGC

VH3418: K A T L T S D K S S S T A Y M E L S S L
AAGGCCACACTGACTTCAGACAAATCCTCCAGCACAGCCTACATGGAGCTCAGCAGCCTG

FIG. 16A3

```
T  S  E  D  S  A  V  Y  Y  C  S  R  F  D  Y  W  G  Q  G
ACCTCTGAGGACTCTGCGGTCTATTACTGTTCAAGACGCTTTGACTACTGGGGCCAAGGG

T  T  V  T  V  S  S
ACCACCGTCACCGTCTCCTCATAATAAGCTAGCGGAGCTGCATGCAAATTCTATTTCAAG

M  K  Y  L  L  P  T  A  A  A  G  L  L  L  L  A
pelB
leader GAGACAGTCATAATGAAATACCTATTGCCTACGGCAGCCGCTGGATTGTTATTACTCGCT A  Q  P  A  M  A  D  I  E  L  T  Q  S  P  S  S  M  Y  A  S
GCCCAACCAGCGGATGGCCGACATCGAGCTCACCCAGTCTCCATCTTCCATGTATGCATCT L  G  E  R  I  T  I  T  C  K  A  S  Q  D  I  N  T  Y  L  T
CTAGGAGAGAGAATCACTATCACTTGCAAGGCGAGTCAGGACATTAATACCTATTTAACC W  F  Q  Q  K  P  G  K  E  P  K  T  L  I  Y  R  A  N  R  L
TGGTTCCAGCAGAAACCAGGGAAATCTCCCAAGACCCTGATCTATCGTGCAAACAGATTG

L D G V P S R F S G S G S G Q D Y S L T
CTAGATGGGGTCCCATCAGGTTCAGTGGCAGTGGATCTGGGCAAGATTATTCTCACC

I S S L D Y E D M G I Y Y C L Q Y D E L
ATCAGCAGCCTGGACTATGAAGATATGGGAATTTATTATTGTCTACAATATGATGAGTTG

Y T F G G G T K L E I K R G G G G S G
TACACGTTCGGAGGGGGGACCAAGCTCGAGATCAAACGGGGTGGAGGCGGTTCAGGCGGA

Linker
G G S G G G G V D I E L T Q S P F S L T
GGTGGCTCTGGCGGTGGCGGGGTCGACATCGAACTCACTCAGTCTCCATTCTCCCTGACT V T A G E K V T M N C K S G Q S L L N S
GTGACAGCAGGAGAGAAGGTCACTATGAATTGCAAGTCCGGTCAGAGTCTGTTAAACAGT

V N Q R N Y L T W Y Q Q K P G Q P P K L
GTAAATCAGAGGAACTACTTGACCTGGTACCAGCAGAAGCCAGGGCAGCCTCCTAAACTG

L I Y W A S T R E S G V P D R F T A S G
TTGATCTACTGGGCATCCACTAGGGAATCTGGAGTCCCTGATCGCTTCACAGCCAGTGGA

S G T D F T L T I S S V Q A E D L A V Y
TCTGGAACAGATTTCACTCTCACCATCAGCAGTGTGCAGGCTGAAGACCTGGCAGTTTAT

Y C Q N D Y T Y P F T F G G G T K L E I
TACTGTCAGAATGATTATACTTATCCGTTCACGTTCGGAGGGGGGACCAAGCTCGAAATC

K R
AAACGGTAATAAGCGGGCCCGCGGAATTC pGOSA.E

MULTIVALENT AND MULTISPECIFIC ANTIGEN-BINDING PROTEIN

FIELD OF THE INVENTION

The present invention relates to multivalent and multi-specific antigen binding proteins, methods for their production and uses thereof. In particular, the invention relates to binding proteins comprising polypeptides which associate to form multivalent or multispecific multimers.

BACKGROUND OF THE INVENTION

Antibodies are protein molecules having a structure based on a unit comprising four polypeptides, two identical heavy chains and two identical light chains, which are covalently linked together by disulphide bonds. Each of these chains is folded in discrete domains. The C-terminal regions of both heavy and light chains are conserved in sequence and are called the constant regions, comprising one or more so-called C-domains. The N-terminal regions of the heavy and light chains, also known as V-domains, are variable in sequence and determine the specificity of the antibody. The regions in the variable domains of the light and heavy chains ($V_L$ and $V_H$ respectively) responsible for antigen binding activity are known as the hypervariable or complementarity determining regions (CDR). Natural antibodies have at least two identical antigen-binding sites defined by the association of the heavy and light chain variable regions.

It is known that proteolytic digestion of an antibody can lead to the production of antibody fragments. Such fragments, or portions, of the whole antibody can exhibit antigen binding activity. An example of a binding fragment is an $F_{ab}$ fragment which comprises a light chain associated with the $V_H$ and $C_{H1}$ domains of a heavy chain. The bivalent $F(ab^1)_2$ fragment comprises two such $F_{ab}$ fragments connected together via the hinge region, giving two antigen binding sites. $F_v$ fragments, consisting only of the V-domains of the heavy and light chains associated with each other may also be obtained. These $F_v$ fragments are monovalent for antigen binding. Smaller fragments such as individual V-domains (domain antibodies or dABs, Ward et al Nature, 341, 544 (1989) and individual CDR's (Williams et al, Proc. Natl. Acad. Sci, U.S.A., 86, 5537 (1989)) have also been shown to retain the binding characteristics of the parent antibody although generally most naturally occurring antibodies need both a $V_H$ and $V_L$ to retain full immunoreactivity.

Antibody fragments comprising $V_H$ and $V_L$ domains associated together to have antigen binding activity have also been described. The single chain $F_v$ fragment (scFv) comprises a $V_H$ domain linked to a $V_L$ domain by a flexible polypeptide linker such that the domains can associate to form an antigen binding site (see, for example, EP-B-0281604, Enzon Labs Inc).

Microbial expression systems for producing active antibody fragments are known in the literature. The production of Fab in various hosts such as *E. coli*. (Better et al, Science, 240, 104, (1988)), yeast (Horwitz et al, Proc. Natl. Acad. Sci, U.S.4, 85, 8678 (1988)) and the filamentous fungus *Trichoderma reesei* (Nyyssönen et al, Bio/Technology, 11, 591 (1993)) have previously been described, for example. It is also known that plants can be used as hosts for the production of SCFv fragments (Owen et al, Bio/Technology, 10, 790 (1992)) as well as whole antibodies.

An advantage of using antibody fragments rather than whole antibodies in diagnosis and therapy lies in their smaller size. They are likely to be less immunogenic than whole antibodies and more able to penetrate tissue. A disadvantage associated with the use of fragments such as the $F_{ab}$, $F_v$, and $S_cF_v$ antibody fragments described above, however is that they have only one binding site for antigen binding as compared to the two or more sites contained in the whole antibody, preventing polyvalent binding to the antigen and hence leading to reduced avidity.

In an attempt to overcome this problem, attention has been directed to providing multivalent antigen binding proteins, that is binding proteins having more than one antigen binding site. In addition, there has been interest in producing antigen-binding proteins having multiple specificities capable of binding to different antigenic determinants and containing antigen binding domains derived from different sources. Antigen-binding proteins having distinct binding specificities may be useful, for example, in targeting effector cells to target cells by virtue of the specific binding of the different binding domains. By way of illustration, a bispecific antigen binding protein having specificity for both tumour cells and cytotoxic drugs may be used to target specifically cytotoxic drug to tumour cell in an efficient manner. By avoiding the need for chemical modification, adverse immune responses may be avoided.

Hitherto, the potential application of multivalent and multispecific antigen binding proteins have been hindered by the difficulties in generating and purifying such molecules.

Recombinant antigen-binding proteins having two binding sites may be prepared by methods such as chemical cross-linking of cysteine residues, either through cysteine residues introduced at the C-terminus of the $V_H$ of an $F_V$ (Cumber et al, J.Immunol., 149, 120 (1992)), through the hinge cysteine residues in $F_{ab}$ to generate $(Fab^1)_2$ (Carter et al, Bio/Tech., 10, 163 (1992)) or at the C-terminus of the $V_L$ of an scFv (Pack and Plückthun, Biochemistry, 31, 1579 (1992)). Alternatively, the production of bivalent and bispecific antibody fragments based on the inclusion of $F_{ab}$ fragments of C-terminal peptide sequences which promote dimerisation has been described. (Kostelny et al, (1992) J.Immunol., 148, 1547).

Bivalent or bispecific antibody fragments comprising a binding complex containing two polypeptide chains, one comprising two heavy chain variable domains ($V_H$) in series and the other comprising two light chain variable domains ($V_L$) in series are described in our pending European Patent Application No. 95307332.7.

Multivalent and/or multispecific antibody fragments are described in WO 94/09131 (Scotgen Limited). Specific binding proteins having two binding regions, contained at least in part on first and second polypeptide chains which chains additionally incorporate associating domains capable of binding to each other causing the polypeptide chains to combine are disclosed therein. It is disclosed that the first and second binding regions preferably are antibody antigen-binding domains, for example comprising $V_H$ and $V_L$ regions contained in a Fab fragment or in a single-chain Fv fragment, or may be derived from just one of the $V_H$ or $V_L$ regions of an antibody. The associating domains may suitably be derived from an antibody and may be inter alia antibody $V_H$ and $V_L$ regions. It is further disclosed that using a $V_H/V_L$ domain combination to achieve association leads to the creation of a supplementary Fv domain such that the antibody produced may be trivalent. Schematic representations of the arrangements suggested in WO 94/09131 to produce trivalent fragments are shown in FIG. 1A. WO 93/11161 (Enzon Inc) describes multivalent antigen-binding proteins comprising two or more single-chain protein molecules, each single chain molecule comprising first and second polypeptides each comprising the binding portion of the variable region of an antibody heavy or light chain with the polypeptides being linked together via a peptide linker. Hypothetical trimers and tetramers are discussed, comprising three or four single-chain antigen binding proteins as appropriate. Schematic representations of the trivalent arrangements suggested are shown in FIG. 1B.

WO 91/19739 (Celltech Limited) discloses multivalent antigen binding proteins comprising an Fv fragment bound to at least one further Fv fragment by a connecting structure which links the Fv fragments together but which maintains them spaced apart such that they can bind to adjacent antigenic determinants. Conveniently the connecting structure consists of a spacing polypeptide and a linkage unit such as a cross-linking maleimide linker or a molecule which allows for non-covalent binding. Particularly preferred connecting structures which are disclosed are based on antibody joining and hinge region sequences.

SUMMARY OF THE INVENTION

According to the present invention there is provided a multivalent antigen binding protein comprising:

a first polypeptide comprising in series, three or more variable domains of an antibody heavy chain; and a second polypeptide comprising, in series, three or more variable domains of an antibody light chain, said first and second polypeptides being linked by association of the respective heavy chain and light chain variable domains, each associated variable domain pair forming an antigen binding site.

As used herein, the term multivalent means more than one antigen binding site.

Preferably the first polypeptide comprises three variable domains of an antibody heavy chain and the second polypeptide comprises three variable domains of an antibody light chain, providing a trivalent protein.

It will be appreciated that the polypeptides may comprise heavy or light chains, variable domains, as appropriate, or functional equivalents thereof.

The respective heavy or light-chain variable domains may suitably be linked without any intervening linker. According to a preferred embodiment, however, the variable domains contained in the individual polypeptides are linked by peptide linkers. Preferably the peptide linker is flexible, allowing the variable domains to flex in relation to each other such that they can bind to multiple antigenic determinants simultaneously. It will be appreciated that the binding of the linker to the individual heavy or light chain variable domains will be such that it does not affect the binding capacity of the binding site formed by the associated variable domain pair. Conveniently the peptide linker comprises from 16 to 19 amino acid residues. A preferred, peptide linker for heavy chain domains is $(Gly_4Ser)_3AlaGlySerAla$ (residues numbered 121–139 of SEQ ID NO:27) and for the light chain domains is $(Gly_4Ser)_3Val$.

It will be appreciated that if two or more of the associated variable domain pairs ($V_H/V_L$ pairs) have the same antigen specificity, for example if they are derived from the same parent antibody or fragment thereof or from different antibodies which bind the same epitope, then a binding protein which binds more than one molecule of the same type will be produced.

According to one embodiment, where the binding protein according to the invention comprises three antigen binding sites which are able to bind different epitopes from each other, a trivalent trispecific protein is produced.

In another embodiment, where the binding protein according to the invention comprises three associated variable domain pair binding sites, two of which sites bind the same epitopes, a trivalent, bispecific protein is provided. Where all three binding sites have the same antigen specificity, a trivalent, monospecific binding protein is provided.

The invention also provides nucleotide sequences coding for the polypeptides of the multivalent antigen binding protein according to the invention and cloning and expression vectors containing such nucleotide sequences.

The invention further provides host cells transformed with vectors containing such nucleotide sequences and methods of producing such polypeptides by expression of the nucleotide sequences in such hosts.

The invention further provides a process for preparing a multivalent antigen binding protein as set forth above comprising:

(i) transforming one or more hosts by incorporating genes encoding said first and second polypeptides;

(ii) expressing said genes in said host or hosts;

(iii) allowing said first and second polypeptides to combine to form the antigen binding protein.

Suitably the host or hosts may be selected from prokaryotic bacteria, such as Gram-negative bacteria, for example *E. coli*, and Gram-positive bacteria, for example *B. subtilis* or lactic acid bacteria, lower eukaryotes such as yeasts, for example belonging to the genera Saccharomyces Kluyveromyces or Trichoderma, moulds such as those belonging to the genera Aspergillus and Neurospora and higher eukaroytes, such as plants, for example tobacco, and animal cells, examples of which are myeloma cells and CHO, COS cells and insect cells. A particularly preferred host for use in connection with the present invention is COS (monkey kidney) cells.

Techniques for synthesising genes, incorporating them into hosts and expressing genes in hosts are well known in the art and the skilled person would readily be able to put the invention into effect using common general knowledge. Proteins according to the invention may be recovered and purified using conventional techniques such as affinity chromatography, ion exchange chromatography or gel filtration chromatography.

The activity of the multivalent binding proteins according to the invention may conveniently be measured by standard techniques known in the art such as enzyme-linked immunosorbant assay (ELISA), radioimmune assay (RIA) or by using biosensors.

The multivalent antigen binding proteins of the present invention may suitably be used in diagnostics or therapy for example in targeting a tumour cell with natural killer cells and cytotoxic agent. Other uses for which the multivalent binding proteins according to the invention are useful include those uses for which antibodies or fragments thereof are commonly used, including for immunoassays of a test sample and in purification. According to a particular preferred embodiment, multi-enzyme complexes may be assembled, at a target, for example a cell surface. As an illustration, multivalent binding proteins according to the invention may be used to target cell killing enzymes such as an oxidase (for example glucose oxidase) and peroxidase (for example horseradish peroxidase) to a target species which is an antigenic component of dental plaque, such as *S. sanguis* or *S. mutans*. Complexes comprising enzyme, coenzyme and target antigen may also conveniently be assembled.

Accordingly, the invention also provides compositions comprising the multivalent antigen binding proteins according to the invention, conveniently in combination with a cosmetically or pharmaceutically acceptable carrier, diluent or excipient. Methods of treatment using the multivalent antigen binding proteins according to the invention are also provided.

For use in diagnosis or therapy, the multivalent antigen binding proteins according to the invention may conveniently be attached to an appropriate diagnostically or therapeutically effective agent or carrier by methods conventional in the art.

An advantage of using multivalents antigen binding proteins according to the invention over multivalent binding proteins prepared by existing techniques known in the art is that the "self-assembling" association of the respective heavy and light chain variable domains to form the multivalent binding sites avoids the need for chemical coupling steps or the introduction of linking residues to stabilise the multivalent constructs, thereby minimising the risk of eliciting an immune response to such molecules when the resulting multivalent binding proteins are used in therapy.

A particular advantage of molecules according to the present invention is that they may conveniently be purified straight from the supernatant using conventional purification techniques. As they are self-assembling, there is no need to purify individual subunits prior to coupling as in existing techniques.

The present invention may be more fully understood with reference to the following description, when read together with the accompanying drawings.

BRIEF DESCRIPTION OF THE DRAWINGS

FIGS. 1A and 1B show schematic representations of published arrangements of heavy and light chain V-domain gene fragments that have been suggested to produce trispecific or trivalent antibody fragments:
A) scFv1-VLa+scFv2-VHa (2 chains) WO 94/09131
B) Fab1-Vla+Fab2-VHa (4 chains) WO 94/09131
C) scFv1-VLa-CLa+scFv1-VHa-CHa (2 chains) WO 94/09131
D) Fab1-VLa-CLa+Fab2-VHa-CHa (4 chains) WO 94/09131
E) scFv1+scFv2+scFv3 (3 chains) WO 93/11161
F) VH1-VL2+VH2-VL3+VH3-VH1 (3 chains) WO 93/11161

FIGS. 2A1–2B2 show the nucleotide sequence of the EcoRI-HindIII insert of pGOSA.E2t containing DNA encoding pelB leader-VH4715-linker-VL3418 and DNA encoding pelB leader-VL3418-linker-VH4715-hydrophil2 tag (SEQ ID No. 1).

FIGS. 3A1–3A3 show the nucleotide sequence of the HindIII-EcoRI insert of plasmid scFv.Lys with DNA encoding pelB leader-VHLys-linker-VLLys (SEQ ID No. 2).

FIGS. 3B1–3B3 show the nucleotide sequence of the HindIII-EcoRI insert of plasmid scFv.4715.2t with DNA encoding pelB leader-VH4715.2t (SEQ ID No. 3).

FIG. 9 shows the expression of the trispecific Golysan proteins on an SDS-PAGE gel containing total COS culture supernatant. Crude supernatants of COS cells transfected with pSV expression vectors were separated on SDS-PAGE gels. The proteins were transferred onto a nitrocellulose membrane and the VH3 and VL3-2t were detected using anti-VH and anti-hydrophil 2 tag specific monoclonal antibodies respectively. (A=anti-Hydro-II, B=anti-Hydro-II+anti-VH) Samples: M) Low Molecular Weight Markers, 1) pSV.K+pSV.V,2) pSV.K+pSV.W,3) pSV.M+pSV.V,4) pSV.M+pSV.W.

FIGS. 12A and 12B show the nucleotide sequence of the EcoRI-HindIII insert of pUR.4124 containing DNA (see SEQ ID NO: 23) encoding $V_L$Lys-Linker-$V_H$Lys.

FIGS. 13A–13C show the nucleotide sequence of the HindIII-EcoRI insert of plasmid Fv.3418 (see SEQ ID NO: 24) containing DNA encoding pelB leader-$V_H$3418 and pelB leader-$V_L$3418.

FIGS. 14A–14C show the nucleotide sequence of the HindIII-EcoRI insert of plasmid Fv.4715-myc (see SEQ ID NO: 25) containing DNA encoding pelB leader-$V_H$4715 and pelB leader-$V_L$4715-Myc tag.

FIGS. 15A–15C show the nucleotide sequence of the HindIII-EcoRI insert of scFv.4715-myc containing DNA (see SEQ ID NO: 26) encoding pelB leader-$V_H$4715-Linker-$V_L$4715-Myc tag.

FIGS. 16A1–16A3 and 16B1–16B2 show the nucleotide sequence of the HindIII-EcoRI insert of pGOSA.E (see SEQ ID NO: 27) containing DNA encoding pelB leader-$V_H$4715-Linker-$V_L$3418 and pelB leader-$V_L$3418-Linker-$V_H$4715.

Figure 1A:
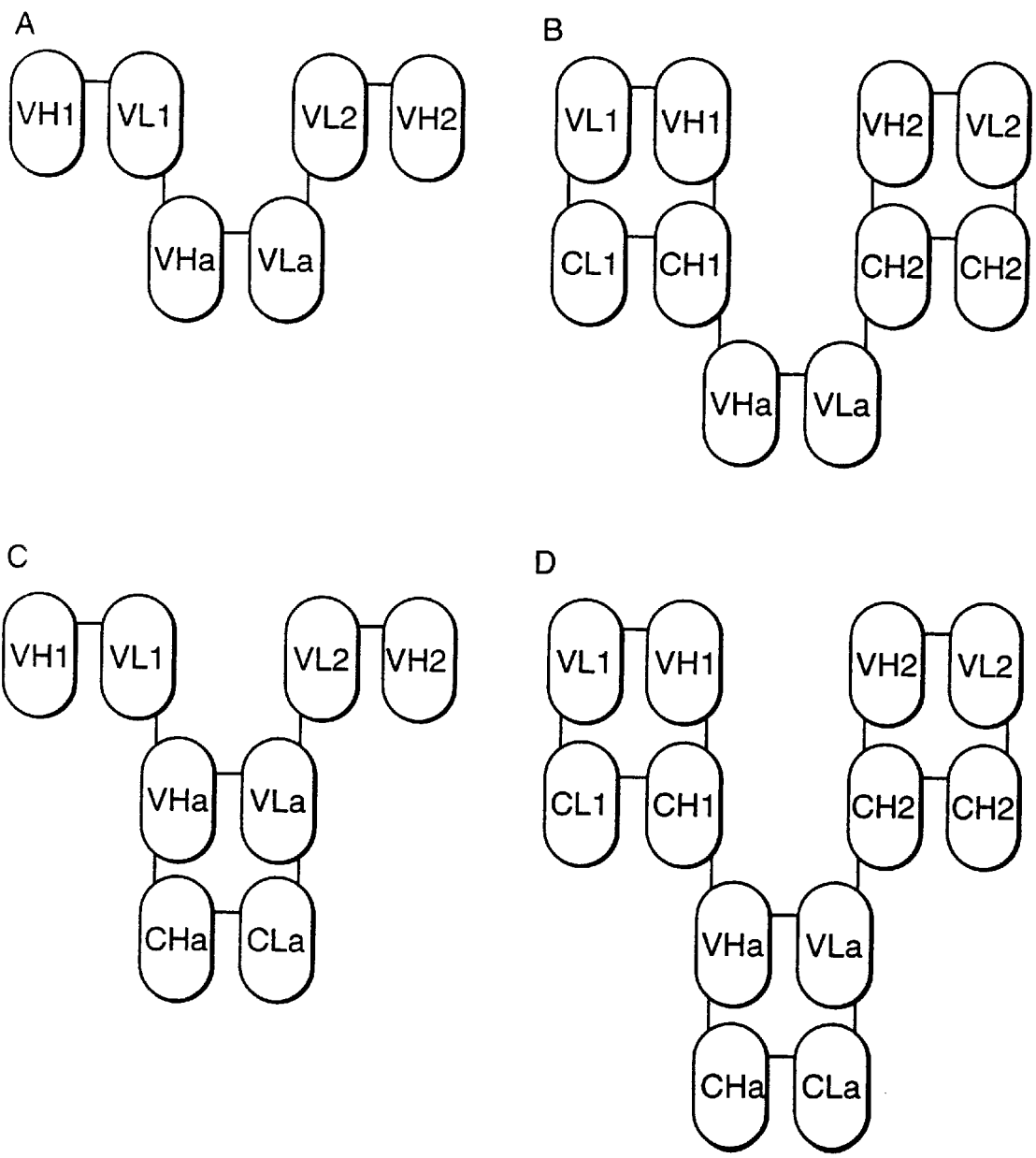

Table 1 shows the nucleotide sequence of all oligonucleotides used in the construction of the described double and triple head constructs.

Table 2 lists all pSV expression constructs described in this specification.

The following examples are provided by way of illustration only:

EXAMPLES

General Experimental

Strains, Plasmids and Media

All cloning steps were performed in *E. coli* JM109 or *E. coli* XL-1 Blue. Cultures were grown in 2×TY/Amp/Glucose medium (16 g tryptone, 10 g yeast extract, 5 g NaCL per liter $H_2O$ supplemented with 2% glucose and 100 g/ml ampicillin). Transformations were plated out on SOBAG plates (20 g tryptone, 5 g yeast extract, 15 g agar, 0.5 g NaCl per liter $H_2O$ plus 10 mM $MgCl_2$, 2% glucose, 100 μg/ml ampicillin). The bicistronic *E. coli* vectors used are derivatives of pUC19. The COS expression vector pSV.51 (LMBP strain nr 1829) was obtained from the LMBP Culture collection (Laboratory of Molecular Biology University Gent). COS-1 cells (ECACC No: 88031701;

African green monkey kidney cells) were obtained from the European Collection of Animal Cell Cultures (ECACC). All tissue culture reagents were from Gibco BRL (Life Technologies, Paisley, UK)

DNA Manipulations

Oligonucleotides and PCR

The oligonucleotide primers used in the PCR reactions were synthesized on an Applied Biosystems 381A DNA Synthesiser by the phosphoramidite method. The primary structures of the oligonucleotide primers used in the construction of the trispecific pSV constructs (Table 2) are shown in Table 1. Reaction mixture used for amplification of DNA fragments were 10 mM Tris-HCl, pH8.3, 2.5 mM $MgCl_2$, 50 mM KCl, 0.01% gelatin (w/v), 0.1% Triton X-100, 400 mM of each dNTP, 5.0 units of Vent DNA polymerase (New England Biolabs), 100 ng of template DNA, and 500 ng of each primer (for 100 μl reactions). Reaction conditions were: 94° C. for 4 minutes, followed by 33 cycles of each 1 minute at 94° C., 1 minute at 55° C., and 1 minute 72° C.

Plasmid DNA\Vector\Insert Preparation and Ligation\Transformation

Plasmid DNA was prepared using the 'Qiagen P-100 and P-500 Midi/Maxi-DNA Preparation' system. Vectors and inserts were prepared by digestion of 10 μg (for vector preparation) or 20 μg (for insert preparation) with the specified restriction endonucleases under appropriate conditions (buffers and temperatures as specified by suppliers). Klenow fill-in reactions and dephosphorylation with Calf Intestine Phosphorylase were performed according to the manufacturers instructions. Vector DNA's and inserts were separated through agarose gel electrophoresis and purified with DEAE-membranes NA45 (Schleicher & Schnell) as described by Maniatis et al. (Molecular cloning: a Laboratory manual, Cold Spring Harbour, N.Y. (1982)) Ligations were performed in 20 μl volumes containing 30 mM Tris-HCl pH7.8, 10 mM $MgCl_2$, 10 mM DTT, 1 mM ATP, 300–400 ng vector DNA, 100–200 ng insert DNA and 1 Weiss unit $T_4$ DNA ligase. After ligation for 2–4 h at room temperature, $CaCl_2$ competent *E. coli* JM109 or XL-1 Blue (Maniatis et al) were transformed using 7.5 μl ligation reaction. The transformation mixtures were plated onto SOBAG plates and grown overnight at 37° C. Correct clones were identified by restriction analysis and verified by automated dideoxy sequencing (Applied Biosystems).

Restriction Digestion of PCR Products

Following amplification each reaction was checked for the presence of a band of the appropriate size by agarose gel electrophoresis. One or two 100 μl PCR reaction mixtures of each of the PCR reactions, together containing approximately 2–4 μg DNA product were subjected to phenol-chloroform extraction, chloroform extraction and ethanol precipitation. The DNA pellets were washed twice with 70% ethanol and allowed to dry. Next, the PCR products were digested overnight (18 h) in 200 μL 1×Buffer with excess of the appropriate restriction enzyme.

Transformation of COS Cells

Cos-1 cells were maintained in DMEM culture medium with glutamine (2 mM), Penicillin (100 U/mL), streptomycin (100 g/mL) containing 10% F.C.S. For transient transfection assays $1-3\times10^5$ COS-1 cells were seeded in 3 cm-diameter tissue culture dishes (2 mL). The cells were incubated at 37° C. in a $CO_2$ incubator until cells were 50–80% confluent (overnight). For each transfection the following mixes were prepared: A) 1 μg of each of the specified DNA's in 100 μL Opti-MEM-I Reduced Serum Medium, B) 1 μL LipofectAmine in 100 μL Opti-MEM-I Reduced Serum Medium. Mixes A and B were combined (gently). After allowing the DNA-liposome complexes to form for 30–45 minutes at room temperature, 0.8 mL Opti-MEM-I Reduced Serum Medium was added to each lipid DNA complex containing tube. The COS-1 cells were washed once with 2 mL of Opti-MEM-I Reduced Serum Medium and overlayed with the diluted complex solution. The COS-1 cells were incubated for 5 hr at 37° C. Following incubation, 2 mL growth medium was added. 20 hours following transfection the medium was replaced with 2 mL fresh growth medium containing 0.1 mM Na-butyrate. After 48 hours incubation at 37° C. the supernatant was harvested and assayed for the presence of antibody fragments.

ELISA

A) GOSA: Glucose Oxidase and *S. sanguis* Binding Activity 96 well ELISA plates (Greiner HC plates) were activated overnight at 37° C. with 200 μl/well of a 1/10 dilution of an overnight culture of *Streptococcus sanguis* cells in 0.05 M sodium carbonate buffer pH9.5 was used to sensitise each well. Following one wash with PBST, the antigen sensitised plates were pre-blocked for 1 hour at 37° C. with 200 μl/well blocking buffer (1% BSA, 0.15% Tween in PBS). 50 μl COS culture supernatants (neat or diluted with PBS) plus 50 μl blocking buffer containing glucose oxidase (50 μg/ml) was added to the *Streptococcus sanguis* sensitised plate and incubated for 2 hours at 37° C. Following 4 washes with PBS-T, bound glucose oxidase was detected by adding 100 μl substrate to each well (70 mM Na-citrate, 320 mM Na-phosphate, 27 mg/ml glucose, 0.5 μg/ml HRP, 100 μg/ml TMB). The colour reaction was stopped after 1 hour by the addition of 35 μl 2M HCl and the A450 was measured.

B) LYSOX: Lysozyme and Glucose Oxidase Binding Activity 96 well ELISA plates (Greiner HC plates) were activated overnight at 37° C. with lysozyme (50 μg/mL in 0.05M sodium carbonate buffer pH9.5; 200 μl/well). Following one wash with PBST, the antigen sensitised plates were pre-blocked for 1 hour at 37° C. with 200 μl/well blocking buffer (1% BSA, 0.15% Tween in PBS). 50 μl COS culture supernatants (neat or diluted with PBS) plus 50 μl blocking buffer containing glucose oxidase (50 μg/ml) was added to the *Streptococcus sanguis* sensitised plate and incubated for 2 hours at 37° C. Following 4 washes with PBS-T, bound glucose oxidase was detected by adding 100 μl substrate to each well (70 mM Na-citrate, 320 mM Na-phosphate, 27 mg/ml glucose, 0.5 μg/ml HRP, 100 μg/ml TMB). The colour reaction was stopped after 1 hour by the addition of 35 μl 2M HCl and the A450 was measured.

C) LYSAN: *S. sanguis* and Lysozyme Binding Activity 96 well ELISA plates (Greiner HC plates) were activated overnight at 37° C. with 200 μl/well of a 1/10 dilution of an overnight culture of *Streptococcus sanguis* cells in 0.05M sodium carbonate buffer pH9.5 was used to sensitise each well. Following one wash with PBST, the antigen sensitised plates were pre-blocked for 1 hour at 37° C. with 200 μl/well blocking buffer (1% BSA, 0.15% Tween in PBS). 50 μl COS culture supernatants (neat or diluted with PBS) plus 50 μl blocking buffer was added to the *Streptococcus sanguis* sensitised plate and incubated for 2 hours at 37° C. Following 4 washes with PBS-T, 50 μL blocking buffer containing Alkaline-Phosphatase conjugated Lysozyme (100 μg/mL). Unbound Lysozyme was removed by 4 washes with PBS-T. Bound Lysozyme was detected by adding 100 μL substrate solution to each well (1 mg/ml pNPP in 1M diethanolamine, 1 mM $MgCl_2$). After 1 hour the A405 was measured.

EXAMPLE 1

Construction of the pSV.Golysan Expression Vectors

The construction of the pSV COS expression vectors consisted of three stages:

1A): Assembly of 2 heavy chain variable domains and 2 light chain variable domains in a pUC based *E. coli* expression vector thus constructing the $VH_A$-$VH_B$ and $VL_A$-$VL_B$ modules respectively.

1B): Assembly of 3 heavy chain variable domains and 3 light chain variable domains in a pUC based *E. coli* expression vector thus constructing the $VH_A$-$VH_B$-$VH_C$ and $VL_A$-$VL_B$-$VL_C$ modules respectively.

2) Linking the $VH_A$-$VH_B$, $VH_A$-$VH_B$-$VH_C$ and $VL_A$-$VL_B$, $VL_A$-$VL_B$-$VL_C$, to the genomic anti-NP leader sequence in the intermediate "EUKA" vectors to ensure efficient secretion by COS cells.

3) Inserting the leader-$VH_A$-$VH_B$, leader-$VH_A$-$VH_B$-$VH_C$ and leader-$VL_A$-$VL_B$, leader-$VL_A$-$VL_B$-$VL_C$ as XbaI/XbaI fragments downstream of the SV40 promoter in the COS expression vector pSV.51.

ad.1) *E. coli* Expression Vectors

The *E. coli* expression vectors are derivatives of pUC.19 containing a HindIII-EcoRI fragment that in the case of the scFv.lys-myc contains a pelB signal sequence fused to the 5' end of the heavy chain V-domain that is directly linked to the corresponding light chain V-domain of the antibody through a connecting sequence that codes for a flexible peptide $(Gly_4Ser)_3$ thus generating a single-chain molecule. In the 'double head' expression vector both the heavy chain and the light chain V-domains of the antibody are preceded by a ribosome binding site and a pelB signal sequence in an artificial dicistronic operon under the control of a single inducible promoter. Expression of these constructs is driven by the inducible lacZ promoter. The nucleotide sequence of the HindIII-EcoRI inserts of the scFv.lys-myc, scFv.4715.2t and pGOSA.E2t constructs used for the generation of the trispecific antibody fragments are listed in FIGS. 3 and 2 respectively.

ad.1A) Assembly of Bi-Specific Fragments or Double Heads

The construct pGOSA.E2t (FIGS. 2 and 6A) is derived from the *E. coli* expression construct pGOSA.E. The construction of pGOSA.E has been described in detail in preparation 1 below.

In contrast with pGOSA.E, pGOSA.E2t contains a peptide tag at the C-terminus of the Variable light chain. Using oligonucleotides DBL3 and DBL.4 the VL4715 gene fragment was amplified using scFv.4715.2t as a template. The SalI/BamHI VH4715.2t PCR fragment and the Hydrophil-2 tag containing BamHI/EcoRI fragment from scFv.4715.2t (FIG. 3B) were used to replace the SalI/EcoRI VH4715 fragment in pGOSA.E thus producing pGOSA.E2t.

Figure 6A:
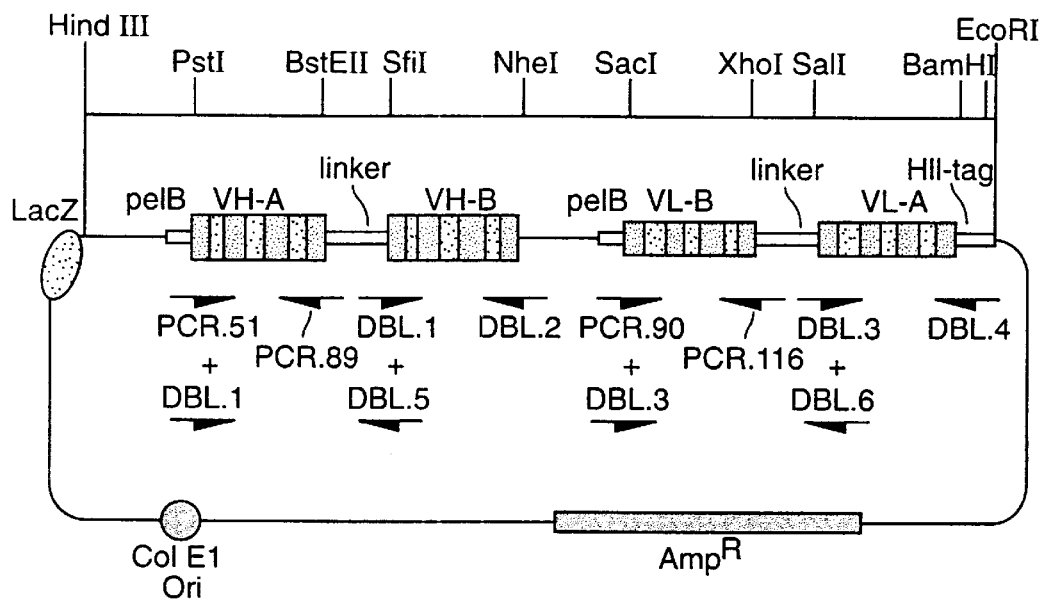
FIG. 6 gives an overview of the pUC19 double head (A) and triple head (B) constructs. The position of the oligonucleotides and the restriction sites used for assembling double and triplehead pUC constructs are indicated.

The vector pGOSA.E2t and the oligonucleotides in Table 1 have been designed to enable most specificities to be cloned into the pGOSA.E2t construct (FIG. 6A). The upstream $V_H$ domain can be replaced by any PstI-BstEII $V_H$ gene fragment obtained with oligonucleotides PCR.51 and PCR.89. The oligonucleotides DBL.1 and DBL.2 were designed to introduce SfiI and NheI restriction sites in the $V_H$ gene fragments thus allowing cloning of those $V_H$ gene fragments into the SfiI-NheI sites as the downstream $V_H$ domain. Using this approach the following $VH_A$-$VH_B$ combinations were constructed: VH4715-VH3416, VH4715-VHlys, VH3418-VHlys, VHlys-VH3418.

All $V_L$ gene fragments obtained with oligonucleotides PCR.116 and PCR.90 can be cloned into the position of the 3418 $V_L$ gene fragment as a SacI-XhoI fragment. A complication here however is the presence of an internal SacI site in the 3418 $V_H$ gene fragment. Oligonucleotides DBL.3 and DBL.4 are designed to allow cloning of $V_L$ gene fragments into the position of the 4715 $V_L$ gene fragment as a SalI-BamHI fragment. A complication here however is the presence of an internal BamHI site in the hydrophil-2-tag gene fragment (2t). Using this approach the following $VL_A$-$VL_B$ combinations were constructed: VL3418-VL4715.2t, VLlys-VL4715.2t and VLlys-VL3418.2t.

ad.1B) Assembly of Tri-Specific Fragments or Triple Heads

Figure 7A:
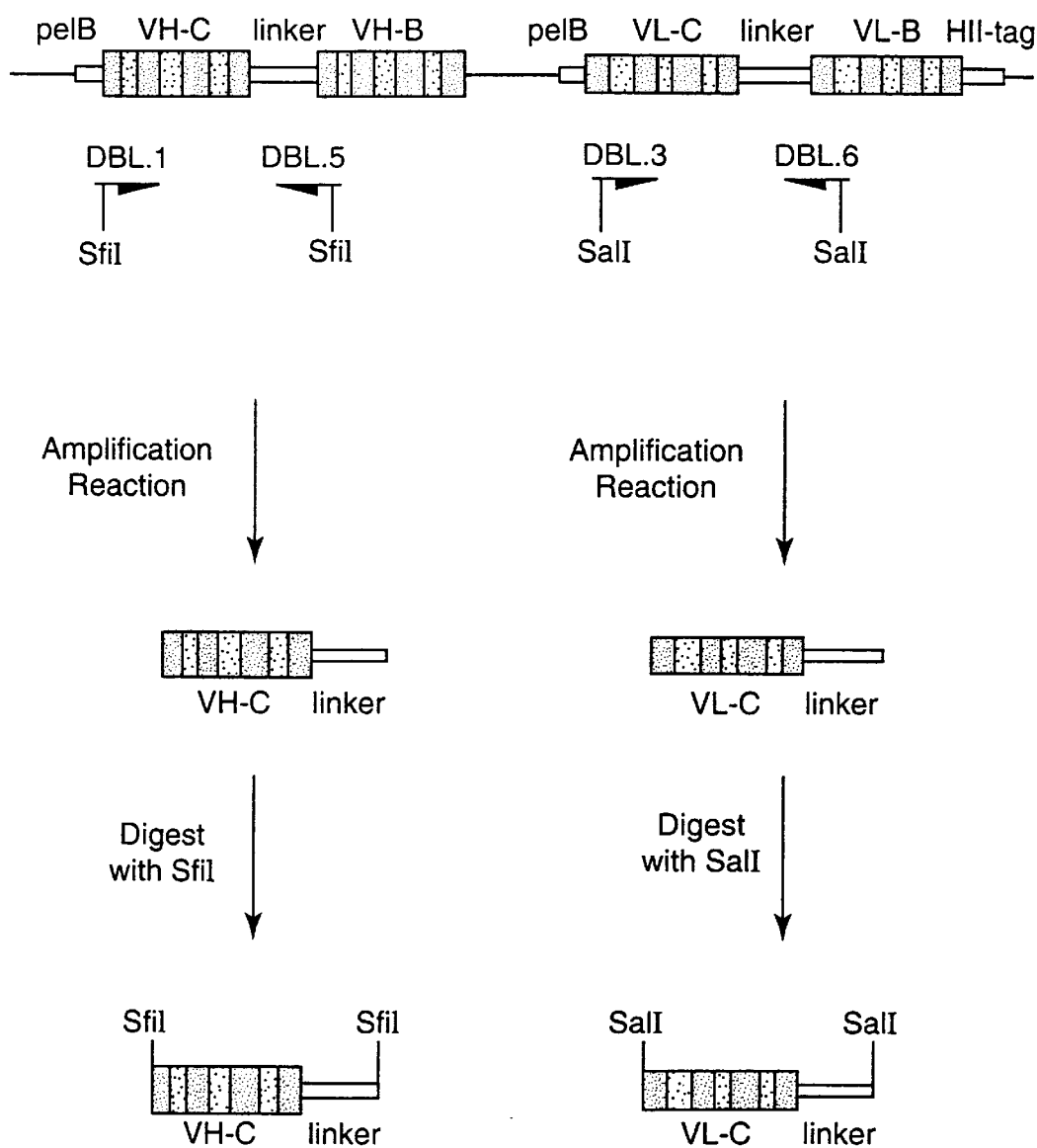
FIG. 7
A) shows the origin of the VH-C-linker and VL-C-linker fragments.
B) gives a schematic representation of the construction of the pUC.19-triple-head vectors.
Figure 7B:
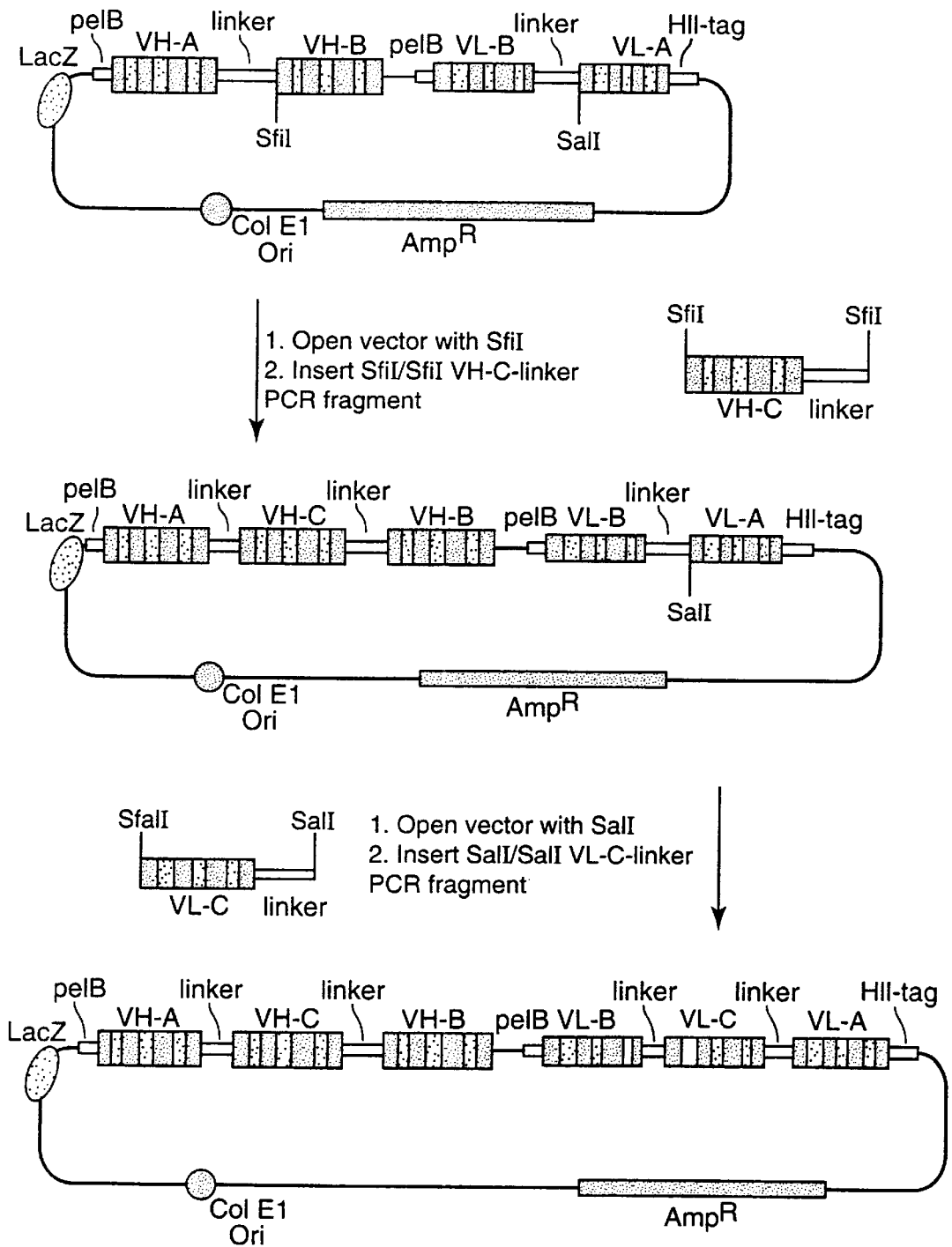

Amplification of the VH-linker fragments using either scFv (VH-linker-VL) or bi-specific constructs (VH-linker-VH) as template with the primer combination DBL.1/DBL.5 (FIG. 7A) yields one of the building blocks for the construction of the $VH_A$-$VH_B$-$VH_C$ modules. The VH-linker DBL.1/DBL.5 PCR fragment is digested with SfiI and inserted into the SfiI site that is present between the linker sequence and the downstream $V_H$ domain in all bi-specific constructs (FIG. 7B) thus producing a $VH_A$-$VH_B$-$VH_C$ module. Using this approach the following $VH_A$-$VH_B$-$VH_C$ combinations were constructed for this filing: VH4715-VHlys-VH3418 and VHlys-VH4715-VH3418.

Using a bi-specific construct (VL-linker-VL) as the template in an amplification reaction with the primer combination DBL.3/DBL.6 (FIG. 7A) yields the VL-linker building block for the construction of the $VL_A$-$VL_B$-$VL_C$ modules. The VL-linker DBL.3/DBL.6 PCR fragment is digested with SalI and inserted into the SalI site that is present between the linker sequence and the downstream VL domain in all bi-specific constructs (FIG. 7B) thus producing a $VL_A$-$VL_B$-$VL_C$ module. Using this approach the following $VL_A$-$VL_B$-$VL_C$ combinations were constructed: VLlys-VL4715-VL3418.2t and VL3418-VLlys-VL4715.2t.

Figure 6B:
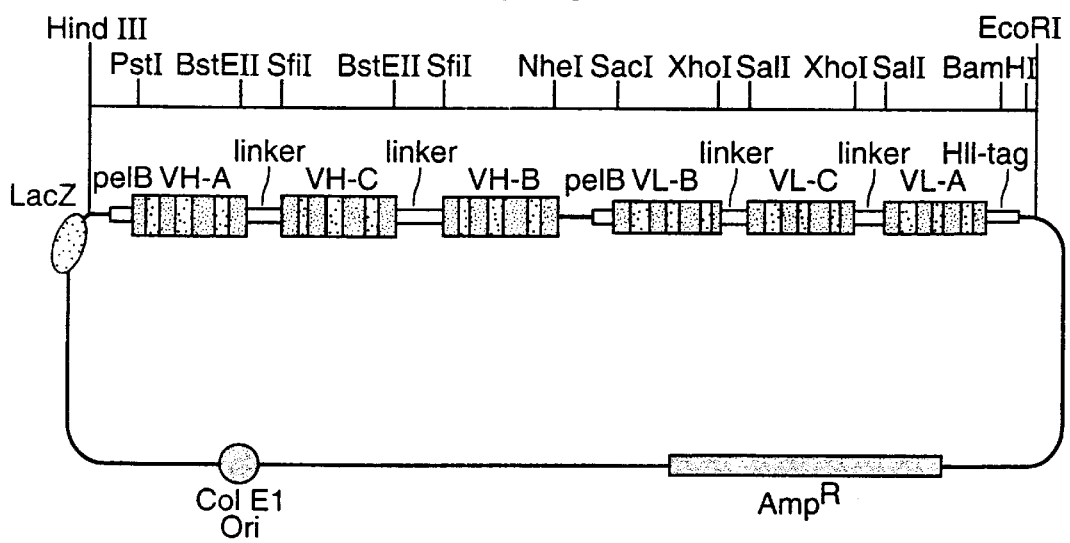

A schematic representation of the final tri-specific constructs is shown in FIG. 6B.

ad.2) Linking the Variable Region Domains to the Leader Sequence

Figure 8A:
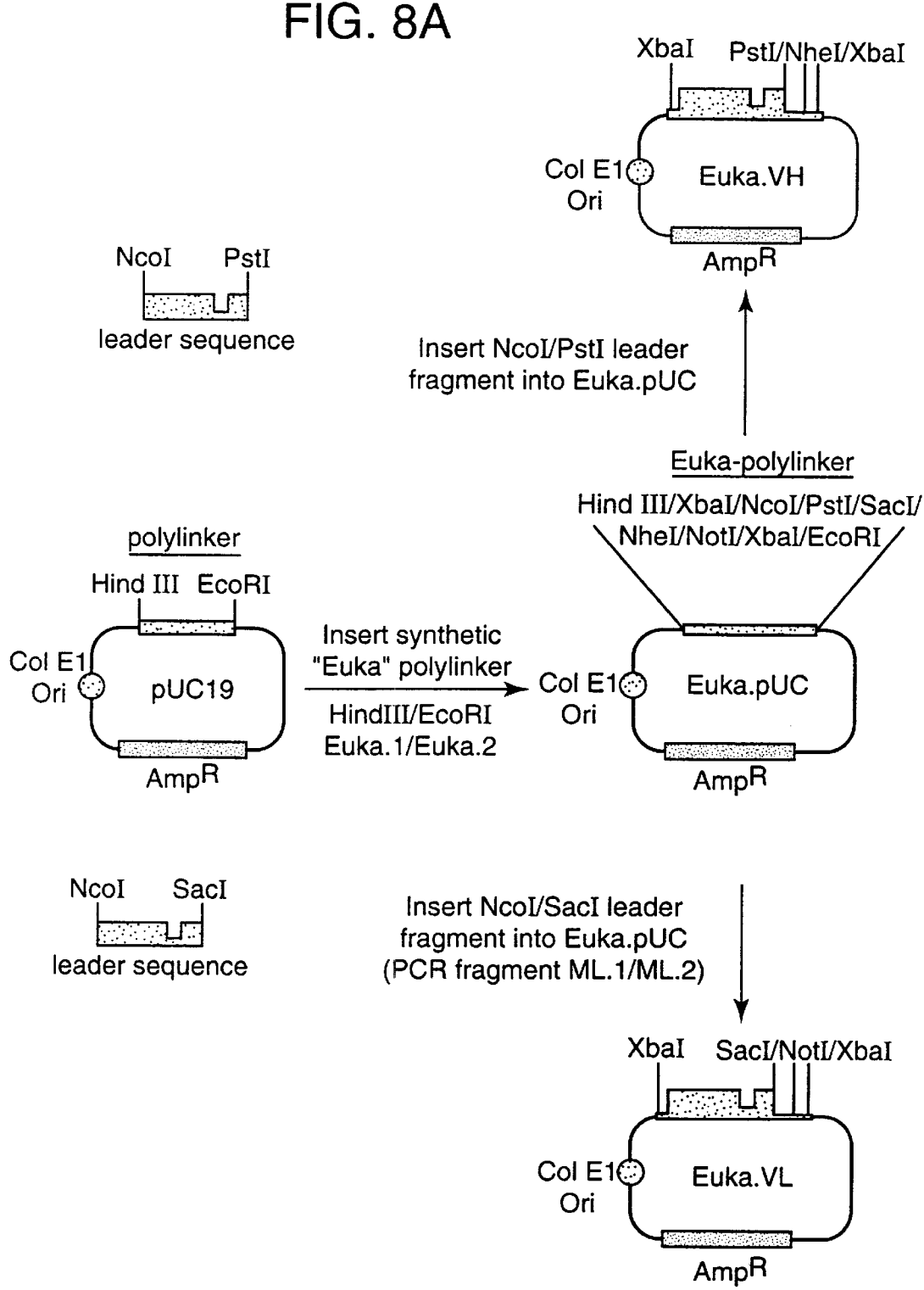
FIG. 8
A) gives a schematic representation of the construction of the Euka.VH and Euka.VL vectors.
B) gives a schematic representation of the construction of the pSV.VH expression vectors.
C) gives a schematic representation of the construction of the pSV.VL expression vectors.

The HindIII/EcoRI polylinker of pUC19 was replaced with a synthetic EcoRI/HindIII 'Euka' polylinker. This was achieved by annealing and inserting the synthetic oligonucleotides Euka.1 and Euka.2 (Table 1) into EcoRI/HindIII digested pUC19 vector. The resulting Euka.pUC vector contains all restriction sites needed for the subcloning of the leader sequence and the VH and VL domains. The NcoI/PstI genomic anti-NP leader sequence fragment was cloned into the NcoI/PstI digested Euka.pUC vector yielding the Euka.VH construct (FIG. 8A).

Oligonucleotides ML.1 and ML.2 (Table 1) were used in an amplification reaction to introduce a SacI site at the 3' end of the leader sequence that allows the construction of leader-VL fusions. The NcoI/SacI leader sequence PCR fragment was inserted into NcoI/SacI digested Euka.pUC vector yielding the Euka.VL construct (FIG. 8A).

Figure 8B:
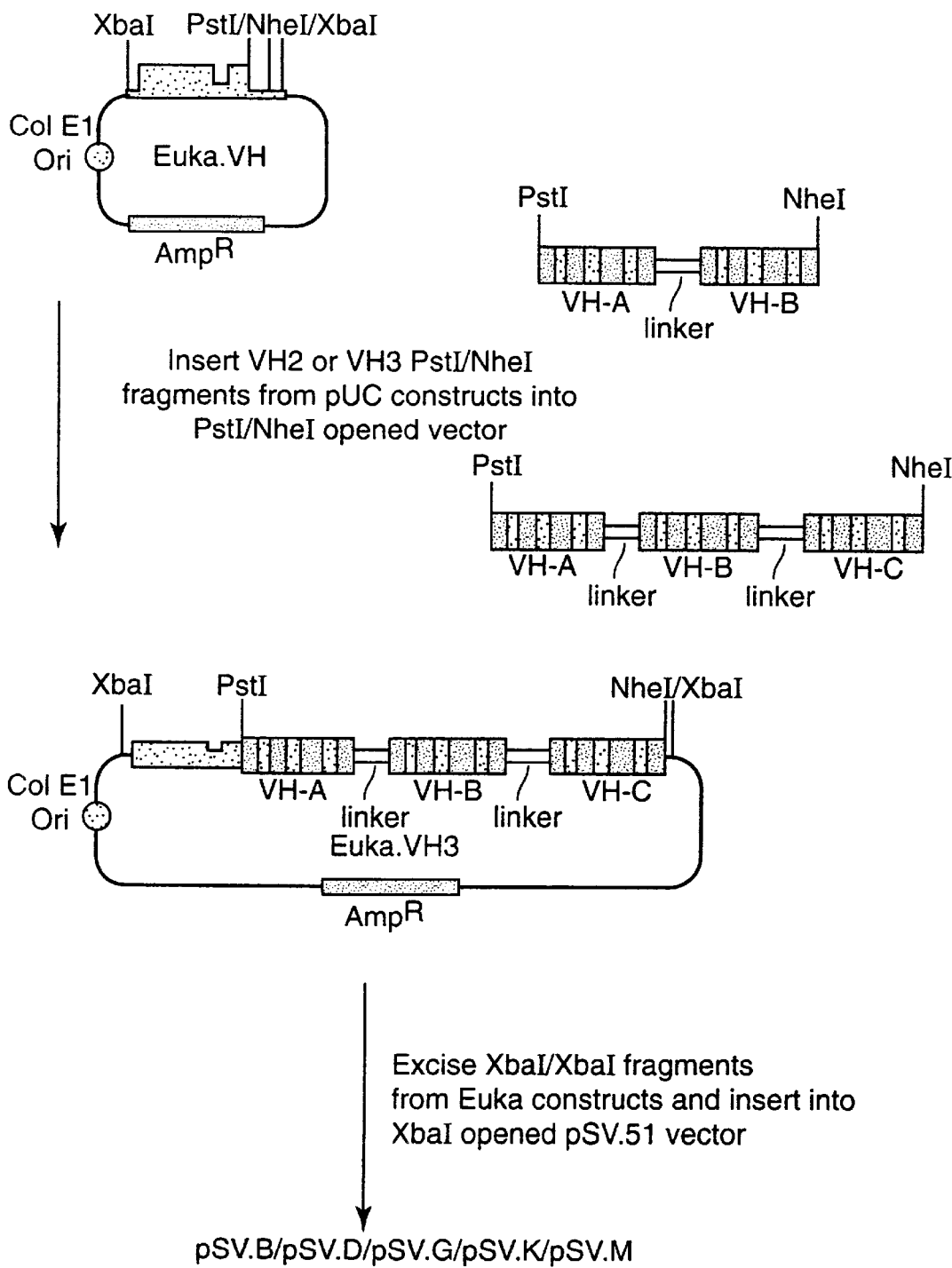

The $VH_A$-$VH_B$ and $VH_A$-$VH_B$-$VH_C$ modules were excised from the pUC expression vectors as PstI/NheI fragments and inserted into PstI/NheI digested Euka.VH vector (FIG. 8B). Using this approach the following leader-$VH_A$-$VH_B$ and leader-$VH_A$-$VH_B$-$VH_C$ combinations were constructed for this filing: Euka.B: leader-VH4715-VH3418, Euka.D: leader-VH4715-VHlys, Euka.G: leader-VH3418-VHlys, Euka.K: leader-VH4715-VHlys-VH3418 and Euka.M: leader-VHlys-VH4715-VH3418.

Figures 4, 5:
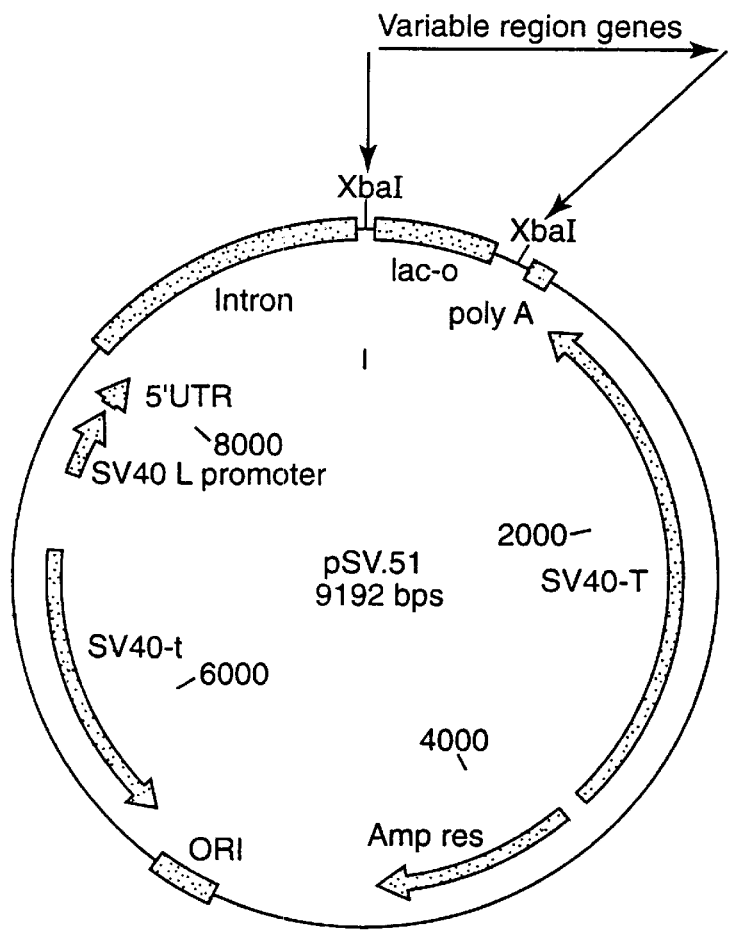
FIG. 4 shows the nucleotide sequence of the genomic leader sequence of the anti-NP antibody (Jones et al, Nature, 321, 522). Exon sequences are indicated with shaded boxes. NcoI and PstI restriction sites are in bold and underlined (SEQ ID No. 4).
FIG. 5 gives a schematic representation of the eukaryotic expression vector pSV.51.
Figure 8C:
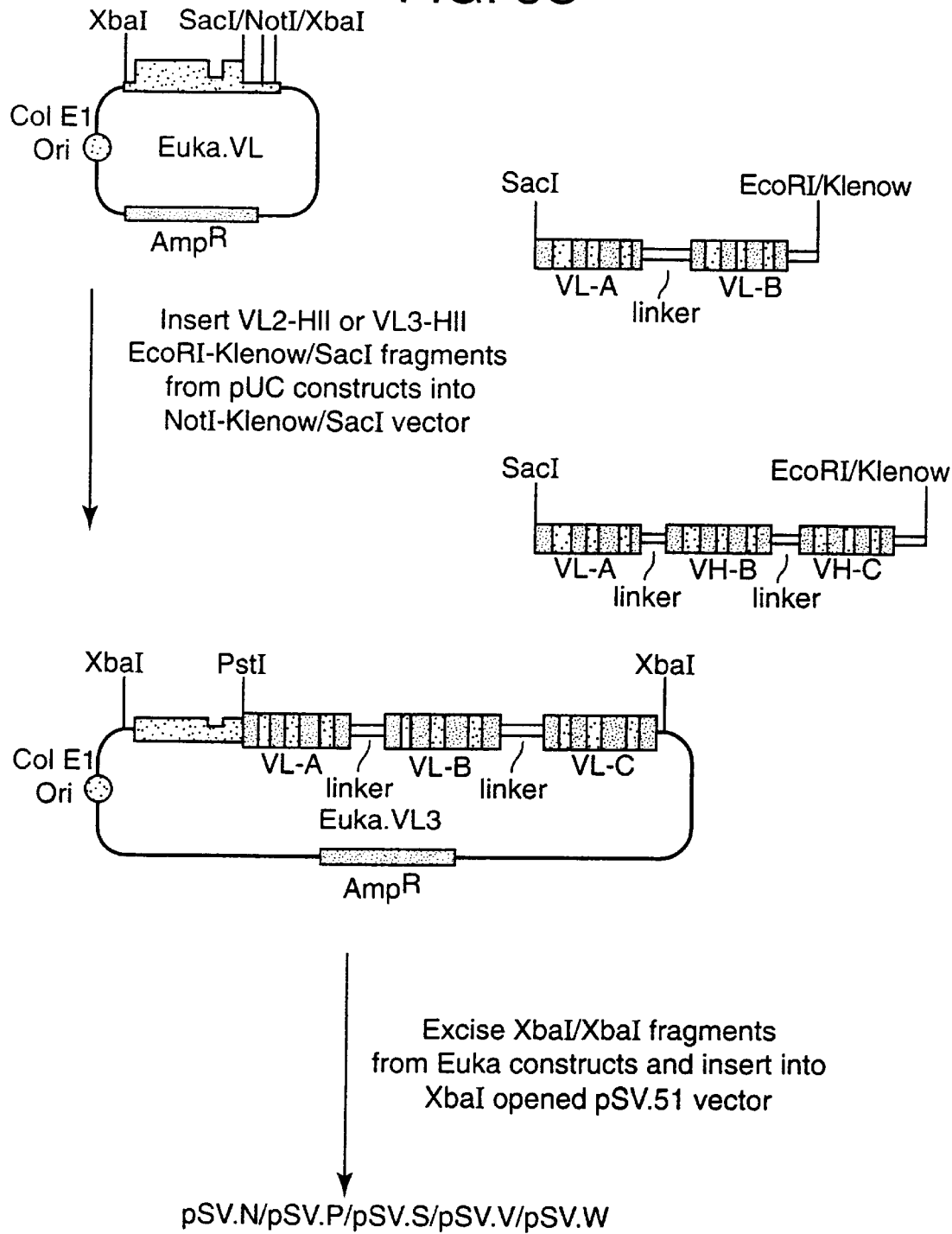

The $VH_A$-$VH_B$ and $VH_A$-$VH_B$-$VH_C$ modules were excised from the pUC expression vectors as EcoRI-Klenow/SacI fragments and inserted into NotI-Klenow/SacI treated Euka.VL vector (FIG. 8C). Using this approach the following leader-$VL_A$-$VL_B$ and leader-$VL_A$-$VL_B$-$VL_C$ combinations were constructed: Euka.N: leader-VL3418-VL4715.2t, Euka.P: leader-VLlys-VL4715.2t Euka.S: leader-VLlys-VL3418.2t, Euka.V: leader-VLlys-VL4715-VL3418.2t and Euka.W: leader-VL3418-VLlys-VL4715.2t.

ad.3) Subcloning of Leader-Variable Domain Fusions Into the pSV.51 Expression Vector All leader-$VH_A$-$VH_B$, leader-$VH_A$-$VH_B$-$VH_C$, leader-$VH_A$-$VH_B$ and leader-$VH_A$-$VH_B$-$VH_C$ combinations were excised from the 'Euka' vectors as XbaI/XbaI fragments and subcloned downstream of the SV40 promoter in pSV.51 (FIG. 5) by insertion into the XbaI site (FIGS. 8B and 8C). After confirmation of the correct orientation of the inserts the pSV expression vectors were used to transfect COS-1 cells (see Example 2). The pSV expression vectors used are listed in Table 2.

EXAMPLE 2

Bifunctional Binding Activity of Golysan Triple Heads

This example describes the production of three types of bispecific binding activity by COS-1 cells transfected with expression plasmids encoding the corresponding $VH_A$-$VH_B$-$VH_C$ and $VL_A$-$VL_B$-$VL_C$ genes fragments.

1. Production of Antibody Fragments by COS-1 Cells

Supernatants of COS-1 cells transfected with combinations of pSV-$VH_A$-$VH_B$-$VH_C$ and pSV-$VH_A$-$VH_B$-$VH_C$ expression plasmids were separated on 10% SDS-PAGE and transferred onto nitrocellulose. The resulting Western blots were screened with a monoclonal antibody recognising a peptide sequence in framework 4 of the VH domains (region encoded by PCR.89: conserved in all used VH domains, {in-house reagent}) and/or a monoclonal specific for the hydrophil-2 tag. As shown in FIG. 9 all supernatants contained products with the expected molecular weight of the $VH_A$-$VH_B$-$VH_C$ and $VL_A$-$VL_B$-$VL_C$ fragments, indicating that the COS cells were successfully tranfected and were secreting the produced antibody fragments into the culture medium at detectable levels.

2. Bifunctional Binding Activity

Figure 10:
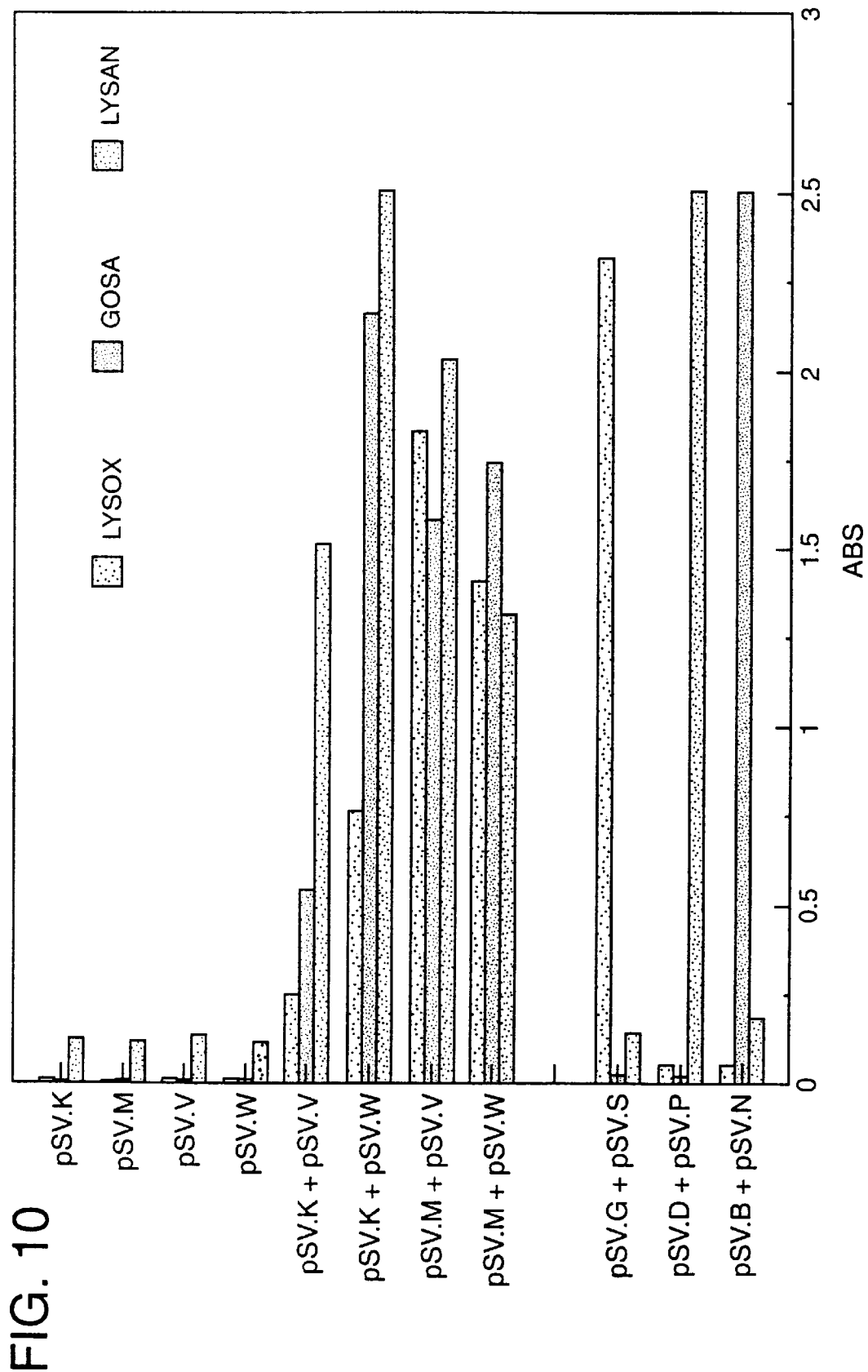
FIG. 10 shows the results of three ELISA's. Lysozyme, Glucose oxidase and S. sanguis binding activity was determined in crude COS supernatants by measuring 1) Lysozyme-Glucose oxidase (=LYSOX), 2) Glucose oxidase -S. sanguis (=GOSA) and 3) Lysozyme-S. sanguis (=LYSAN) bispecific binding activities.

Supernatants of COS-1 cells transfected with single pSV expression plasmids and combinations of pSV expression plasmids were tested for the production of bifunctional binding activity using ELISA format:

Supernatants of COS-1 cells transfected with the bispecific positive controls 'LYSAN' (pSV.D+pSV.P), 'LYSOX' (pSV.G+pSV.S) and 'GOSA' (pSV.B+pSV.N) only produced LYSAN, LYSOX and GOSA bispecific activity respectively (FIG. 10). No significant cross reactivity was detected.

Supernatants of COS-1 cells transfected with only one expression vector encoding either one of the $VH_A$-$VH_B$-$VH_C$ fragments (pSV.K and pSV.M) or one of the $VL_A$-$VL_B$-$VL_C$ fragments (pSV.V and PSV.W) did not exhibit any bispecific binding activity, indicating that no background binding or a specific binding activity is produced.

All tested supernatants of COS-1 cells transfected with an expression vector encoding one of the $VH_A$-$VH_B$-$VH_C$ fragments (pSV.K and pSV.M) and an expression vector encoding one of the $VL_A$-$VL_B$-$VL_C$ fragments (pSV.V and pSV.W) showed significant levels of all three bifunctional binding activities LYSOX, GOSA and LYSAN.

These results show that COS cells transfected with expression vectors encoding $VH_A$-$VH_B$-$VH_C$ and expression vectors encoding $VL_A$-$VL_B$-$VL_C$ fragments produce and secrete molecules that contain three binding activities. In this example those three activities are: Glucose Oxidase binding, *S. sanguis* binding and Lysozyme binding. Furthermore, the results illustrated in FIG. 10 clearly show that at least two of these binding activity are present in one self assembling molecular complex. In this example those combinations are: GOSA (Glucose Oxidase+*S. sanguis*), LYSOX (Lysozyme+Glucose Oxidase) and LYSAN (Lysozyme+*S. sanguis*).

EXAMPLE 3

Trifunctional Binding Activity of Golysan Triple Heads

This example describes experiments that show that the three types of bispecific binding activity that are produced by COS-1 cells transfected with expression plasmids encoding the corresponding $VH_A$-$VH_B$-$VH_C$ and $VL_A$-$VL_B$-$VL_C$ genes fragments are present in one self assembling molecular complex.

Golysan.A (VHlys-VH4715-VH3418+VLlys-VL4715-VL3418.2t) and Golysan.B (VHlys-VH4715-VH3418+VL3418-VLlys-VL4715.2t) was purified by affinity chromatography. 100 ml supernatant of COS-1 cells transfected with expression plasmids pSV.M/pSV.V (Golysan.A) or pSV.M/pSV.W (Golysan.B) were loaded onto a Lysozyme-Sepharose column (CNBr-Sepharose, Pharmacia; column was prepared according to the manufacturer's instructions). After extensive washes with PBS the bound Golysan antibody fragments were eluted in 0.1M glycine buffer at pH=2.2. The fractions were neutralised with Tris and tested for the presence of trispecific binding activity.

Figure 11A:
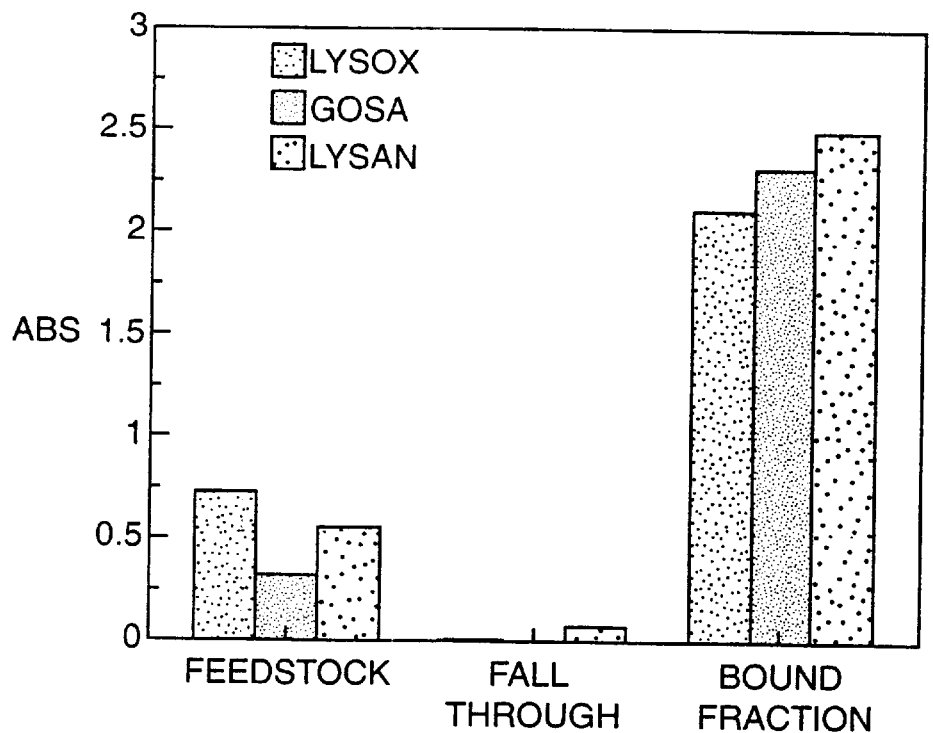
FIG. 11 shows the results of three ELISA's. Lysozyme, Glucose oxidase and S. sanguis binding activity of purified Golysan.A (A) and Golysan.B (B) was determined by measuring 1) Lysozyme-Glucose oxidase (=LYSOX), 2) Glucose oxidase-S. sanguis (=GOSA) and 3) Lysozyme-S. sanguis (=LYSAN) bispecific binding activities.
Figure 11B:
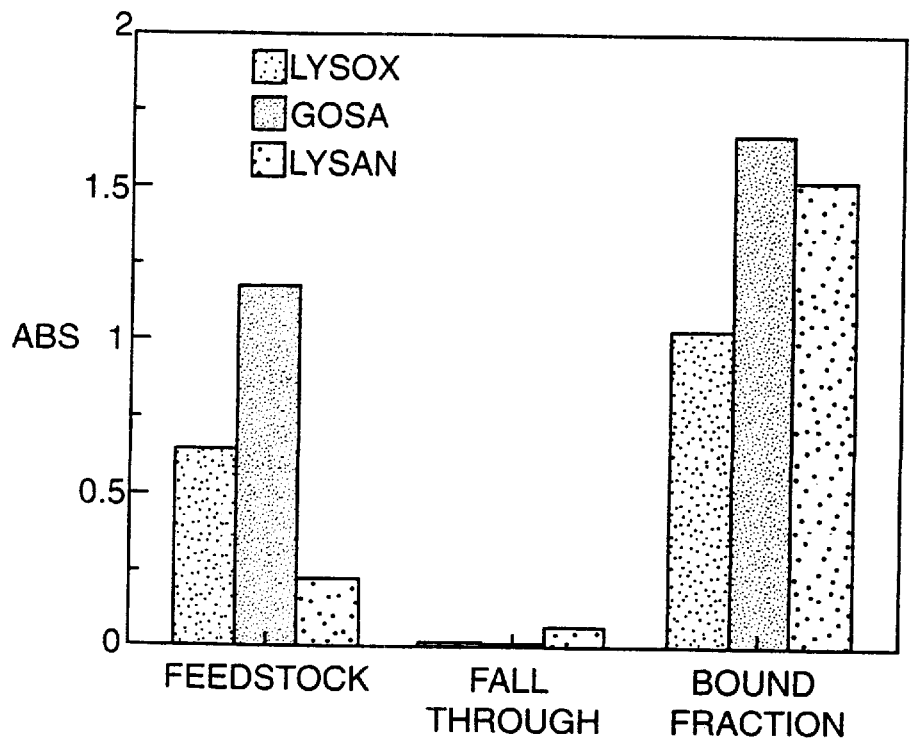

As shown in FIG. 11 no bispecific binding activity was detect in the column fall-through. All three bispecific binding activities (GOSA, LYSOX and LYSAN) were extracted from the COS-1 supernatant by passing over the Lysozyme affinity matrix. After acid elution all three bispecific binding activities (GOSA, LYSOX and LYSAN) were recovered from the column. Since both Golysan.A and B were affinity purified based on the ability to bind to Lysozyme, the finding that these molecules also bind *S. sanguis* and Glucose Oxidase shows that all three binding activities are present in one self assembling molecular complex.

Preparation 1

Construction of the pGOSA.E Double Head Expression Vector

In the pGOSA expression vectors, the DNA fragments encoding both the $V_H$ and $V_L$ of the antibody are preceded by a ribosome binding site and a DNA sequence encoding the pelB signal sequence in an artificial dicistronic operon under the control of a single inducible promoter. Expression of these constructs is driven by the inducible lacZ promoter. The nucleotide sequence of the HindIII-EcoRI inserts of the plasmids pUR.4124 (SEQ ID NO. 23), Fv.3418 (SEQ ID NO. 24), Fv.4715-myc (SEQ ID NO. 25) and scFv.4715-myc (SEQ ID NO. 26) constructs used for the generation of the bispecific antibody fragments are given in FIGS. 12–15, respectively. Moreover, a culture of *E. coli* cells harbouring plasmid scFv.4715-myc and a culture of *E. coli* cells harbouring plasmid Fv.3418 were deposited under the Budapest Treaty at the National Collection of Type Cultures (Central Public Health Laboratory) in London (United Kingdom) with deposition numbers NCTC 12916 and NCTC 12915, respectively.

In agreement with Rule 28 (4) EPC, or a similar arrangement for a State not being a Contracting State of the EPC, it is hereby requested that a sample of such deposit, when requested, will be submitted to an expert only.

The construction of pGOSA.E (see FIG. 16 for the HindIII-EcoRI insert of pUC19) involved several cloning steps. The appropriate restriction sites in the various domains were introduced by PCR directed mutagenesis using the oligonucleotides listed in Table 1 below.

Figure 16C:
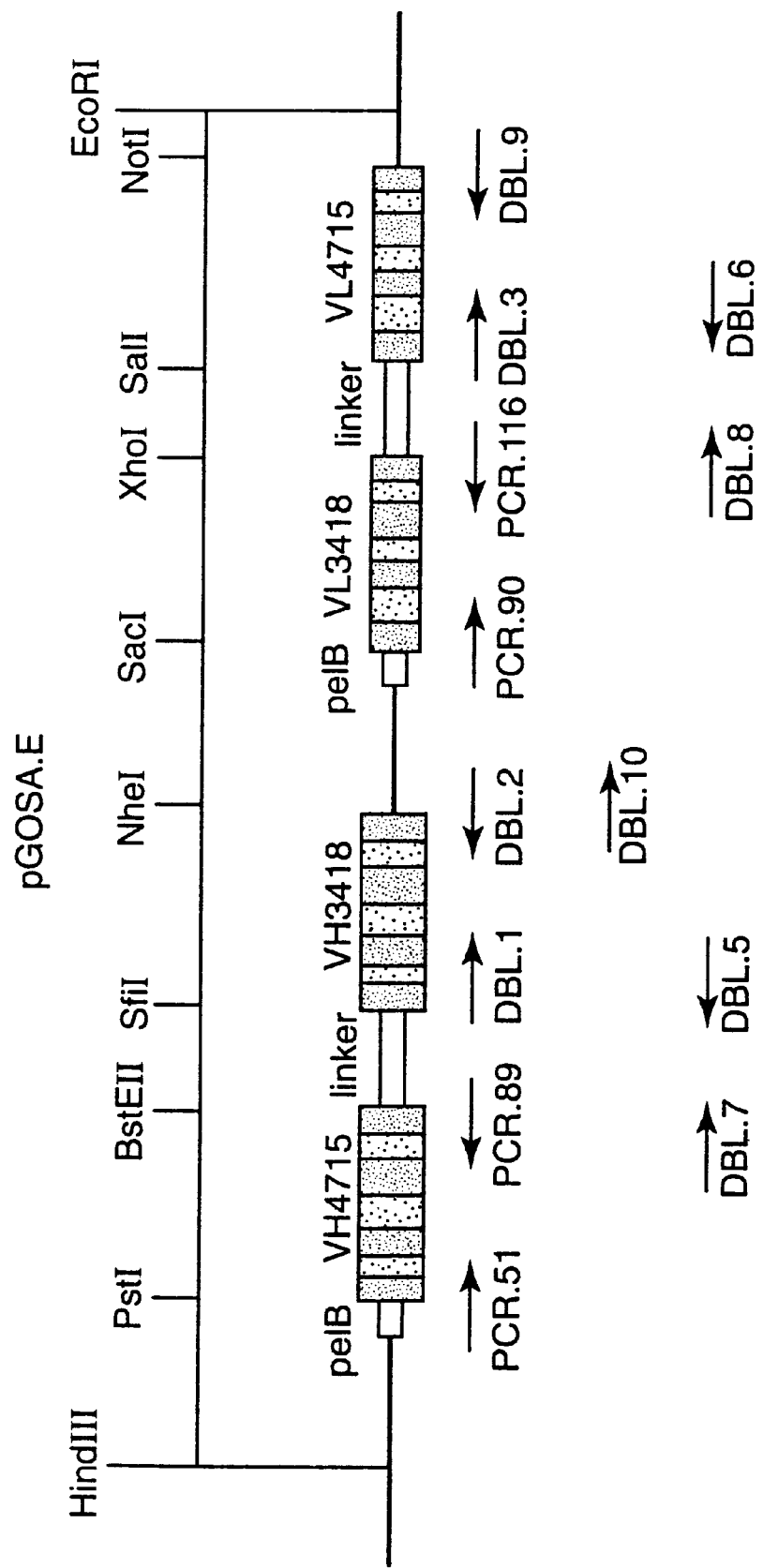
FIG. 16C gives an overview of the oligonucleotides and their positions in pGOSA.E that can be used to replace V-domain gene fragments.
Figure 17:
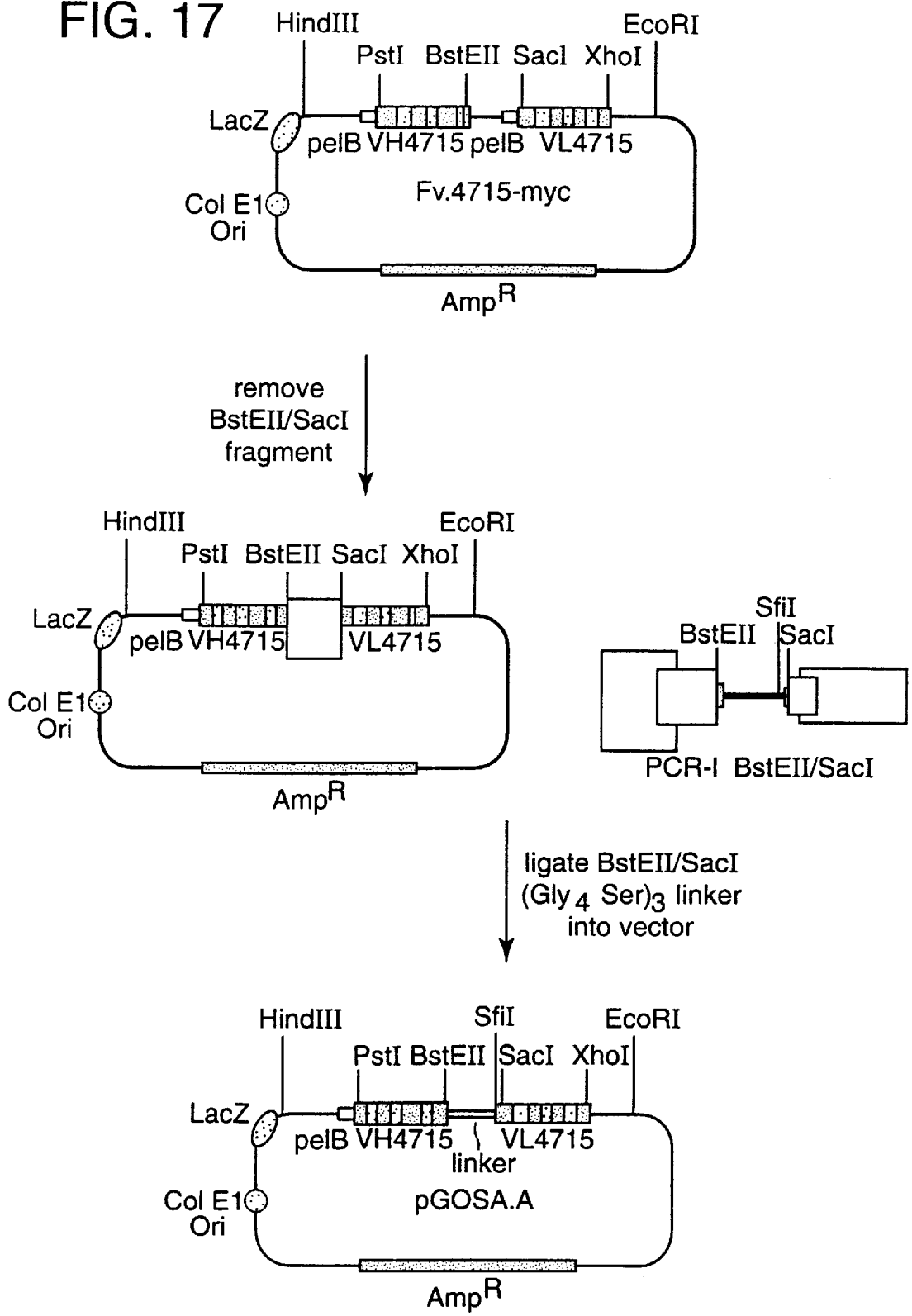
FIG. 17 shows the construction of plasmid pGOSA.A.

The construction of pGOSA.E involved several cloning steps that produced 4 intermediate constructs pGOSA.A to PGOSA.D (see FIGS. 17–21). The final expression vector pGOSA.E and the oligonucleotides in Table 1 have been designed to enable most specificities to be cloned into the final pGOSA.E construct (FIG. 16c). The upstream $V_H$ domain can be replaced by any PstI-BstEII $V_H$ gene fragment obtained with oligonucleotides PCR.51 and PCR.89 (see Table 1). The oligonucleotides DBL.1 and DBL.2 (see Table 1 ) were designed to introduce SfiI and NheI restriction sites in the $V_H$ gene fragments thus allowing cloning of those $V_H$ gene fragments into the SfiI-NheI sites as the downstream $V_H$ domain. All $V_L$ gene fragments obtained with oligonucleotides PCR.116 and PCR.90 (see Table 1) can be cloned into the position of the VL.3418 gene fragment as a SacI-XhoI fragment. A complication here however is the presence of an internal SacI site in the $V_H$.3418gene fragment. Oligonucleotides DBL.3 and DBL.9 (see Table 1) are designed to allow cloning of $V_L$ gene fragments into the position of the $V_L$.4715 gene fragment as a SalI-NotI fragment.

pGOSA.A

Figure 22:
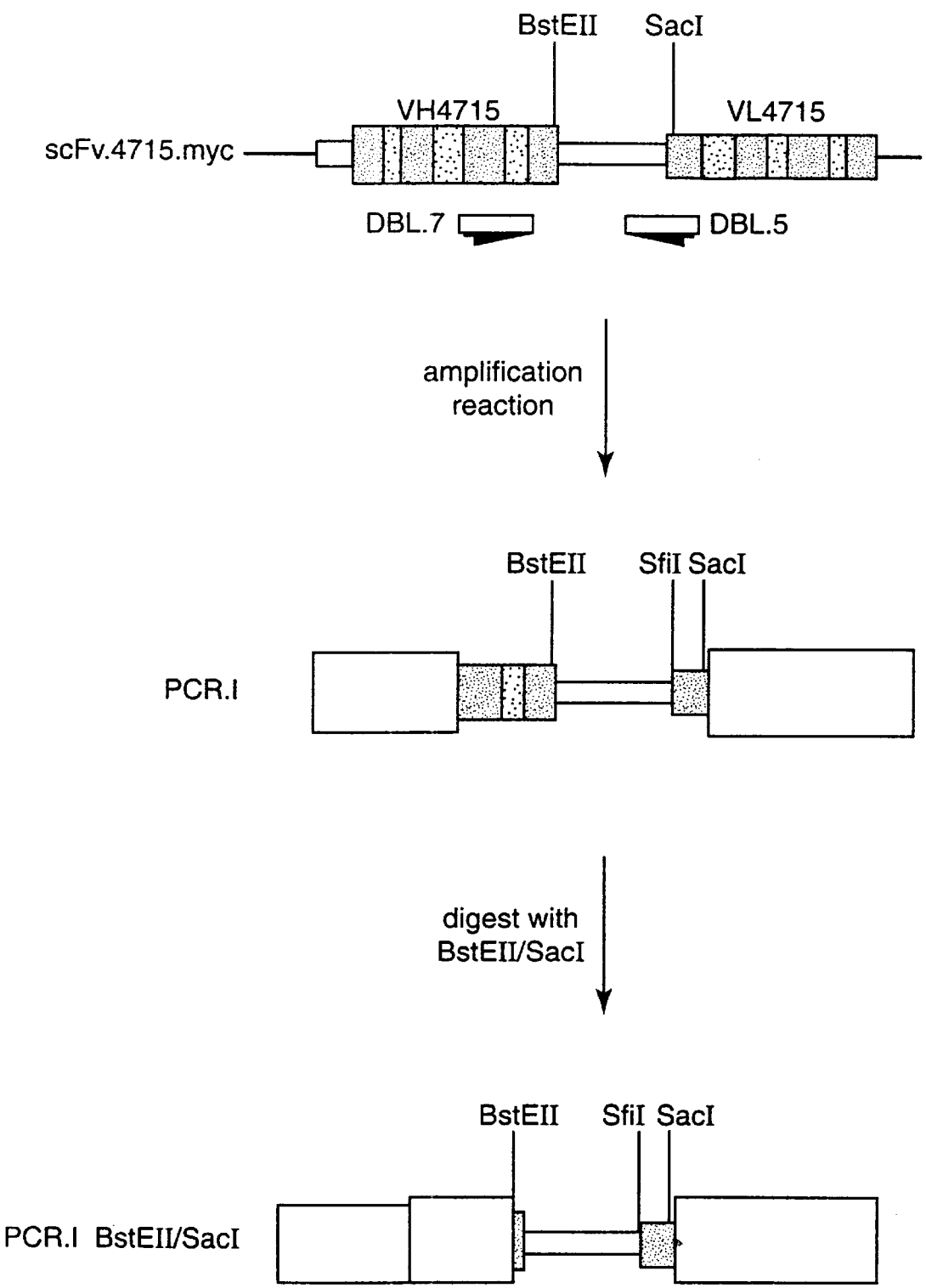
FIG. 22 shows the source of fragment PCR.I BstEII/SacI.

This plasmid is derived from both the Fv.4715-myc construct (SEQ ID NO. 25) and the scFv.4715-myc construct (SEQ IN NO. 26). An SfiI restriction site was introduced between the DNA sequence encoding the $(Gly_4Ser)_3$ linker and the gene fragment encoding the $V_L$ of the scFv.4715-myc construct (see FIG. 17). This was achieved by replacing the BstEII-SacI fragment of the latter construct by the fragment PCR-I BstEII/SacI (FIG. 22) that contains an SfiI site between the DNA encoding the $(Gly_4Ser)_3$ linker and the $V_L$.4715 gene fragment. The introduction of the SfiI site also introduced 4 additional amino acids (AlaGlySerAla) between the $(Gly_4Ser)_3$ linker and $V_L$.4715 resulting in a $(Gly_4Ser)_3$AlaGlySerAla linker (linkerA). The oligonucleotides used to produce PCR-I (DBL.5 and DBL.7, see Table 1) were designed to match the sequence of the framework-3 region of $V_H$.4715 and to prime at the junction of the DNA encoding the $(Gly_4Ser)_3$ linker and the $V_L$.4715 gene fragment, respectively. Thus pGOSA.A can be indicated as:

pelB-$V_H$4715-linkerA-(SfiI)-$V_L$4715-myc.

pGOSA.B

Figure 18:
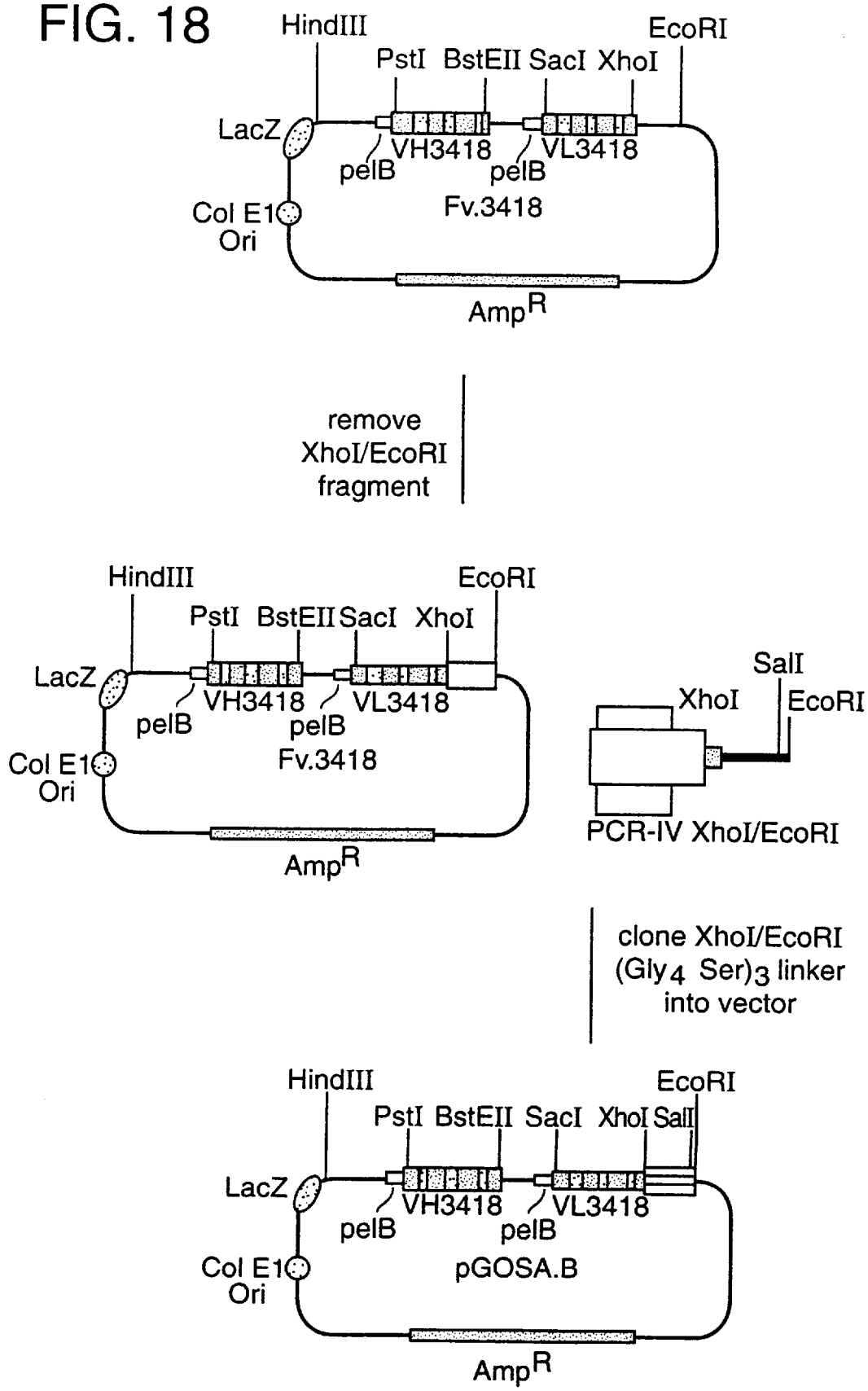
FIG. 18 shows the construction of plasmid pGOSA.B.
Figure 19:
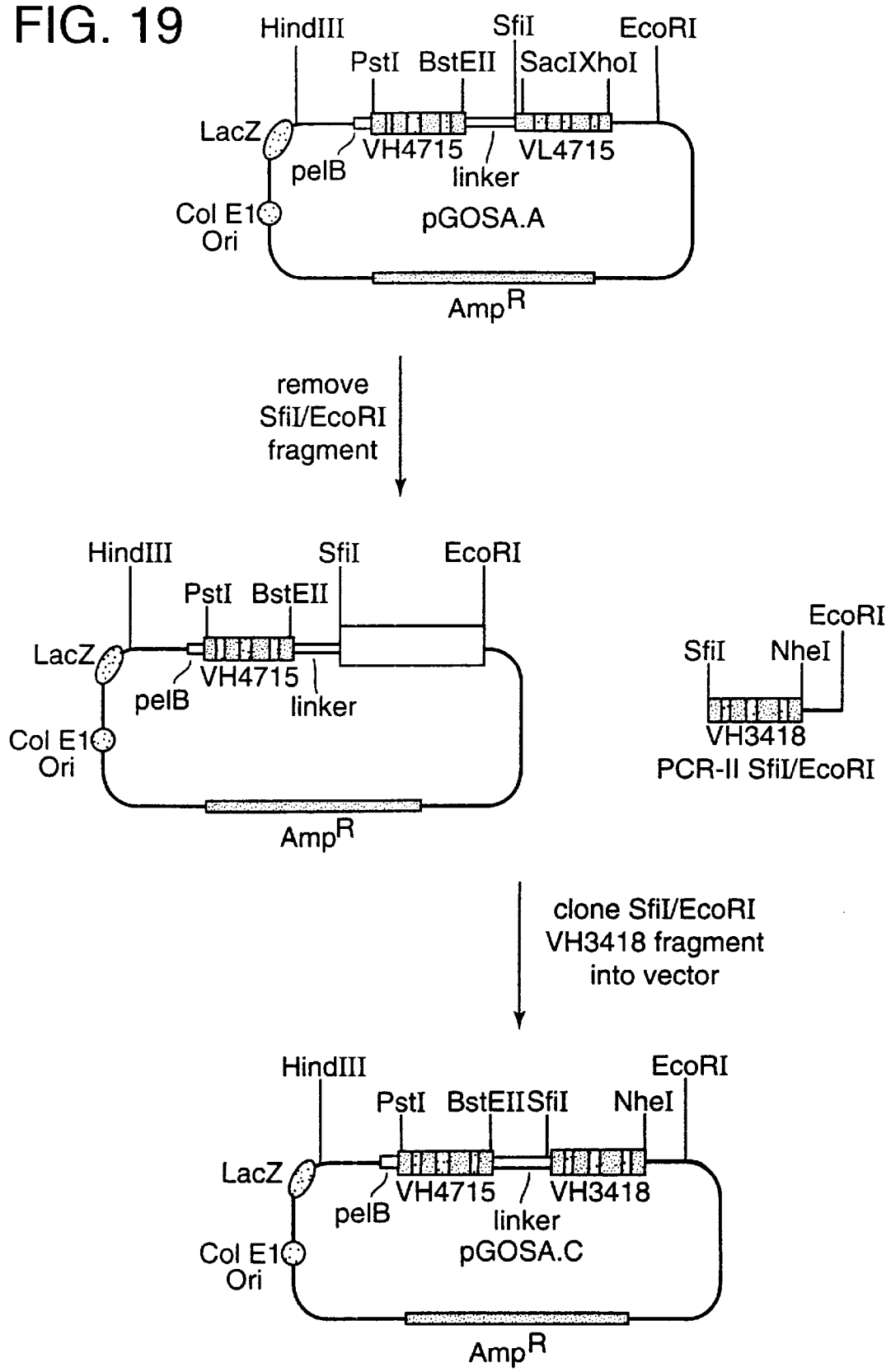
FIG. 19 shows the construction of plasmid pGOSA.C.
Figure 20:
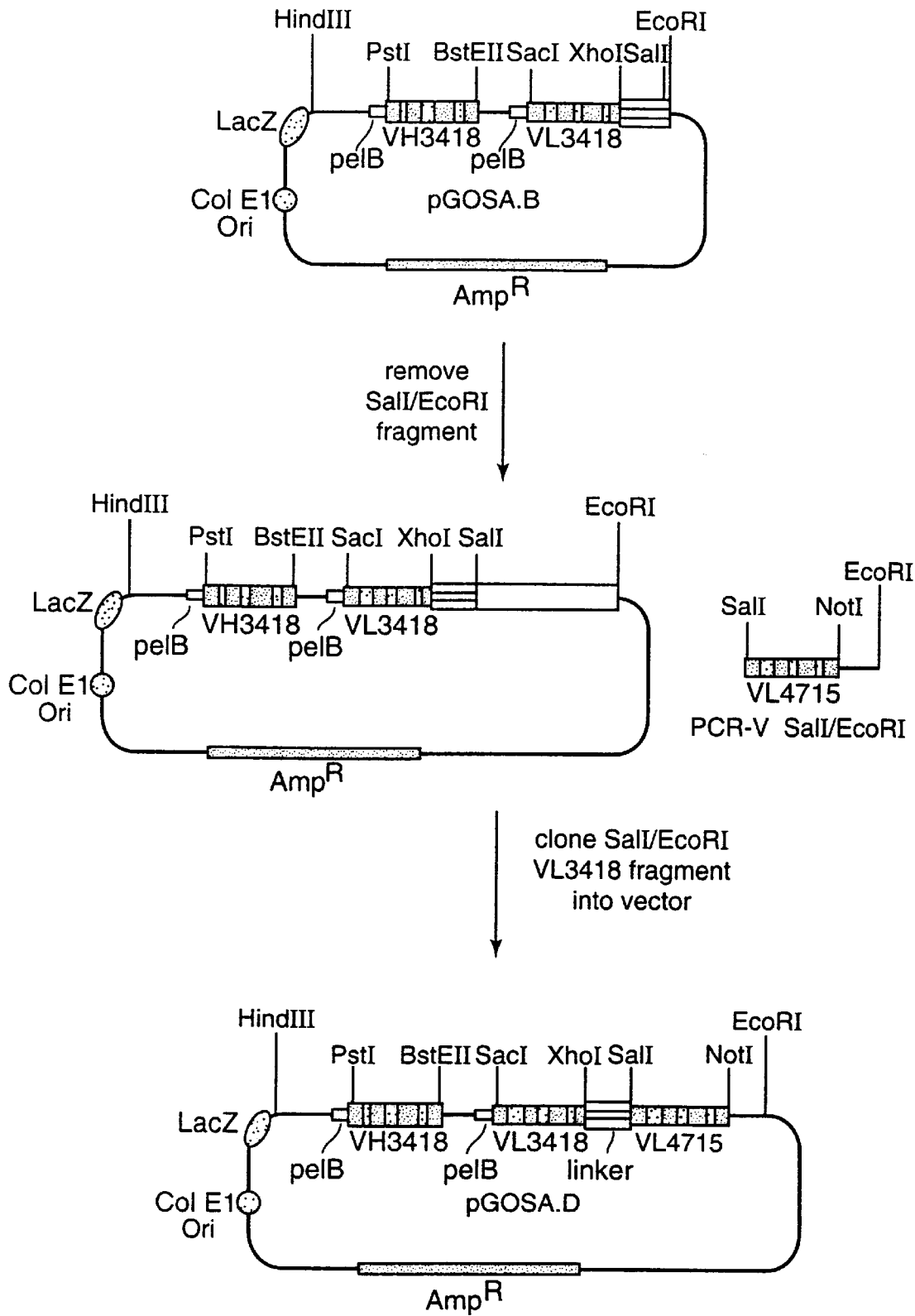
FIG. 20 shows the construction of plasmid pGOSA.D.
Figure 21:
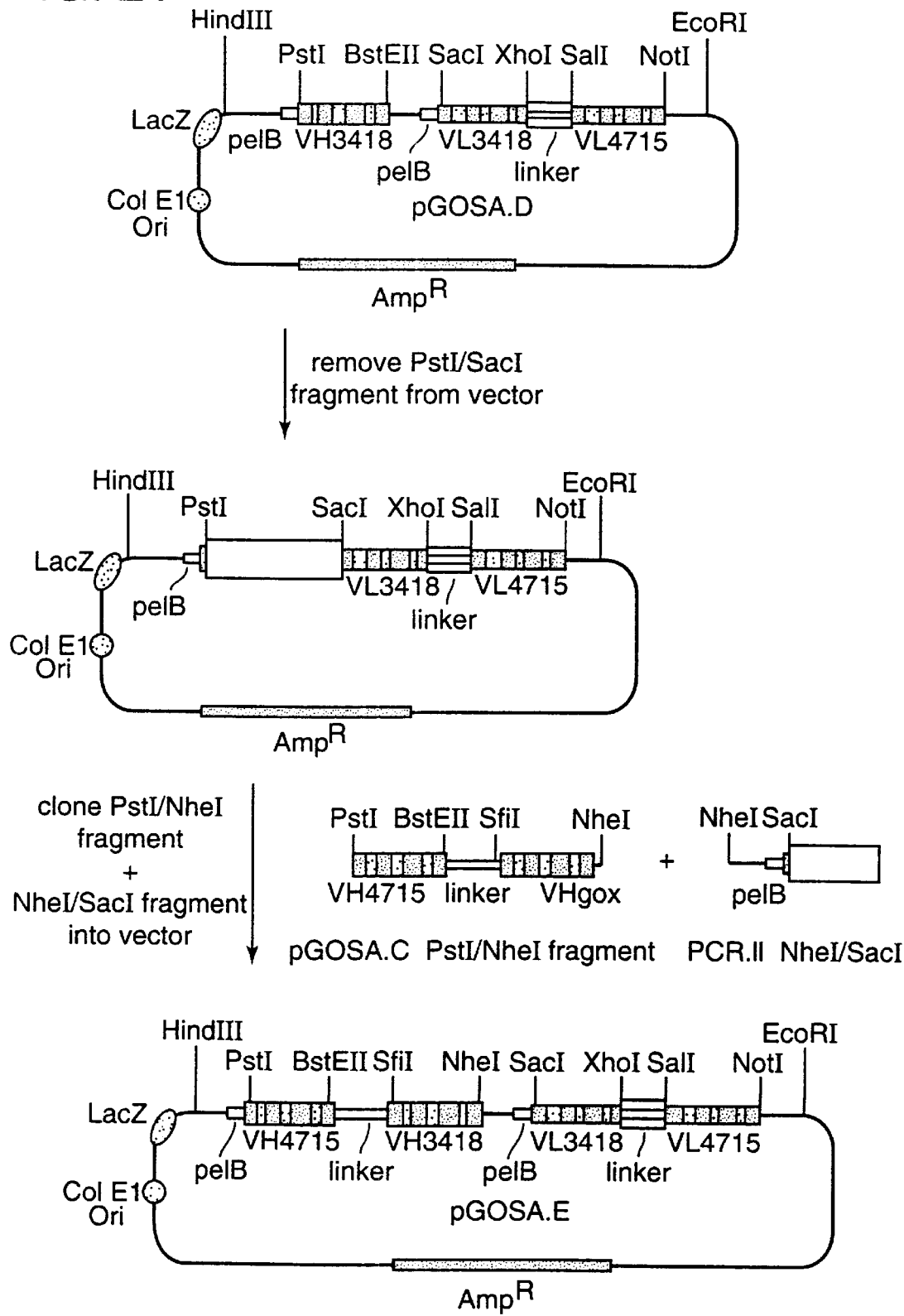
FIG. 21 shows the construction of plasmid pGOSA.E.
Figure 23:
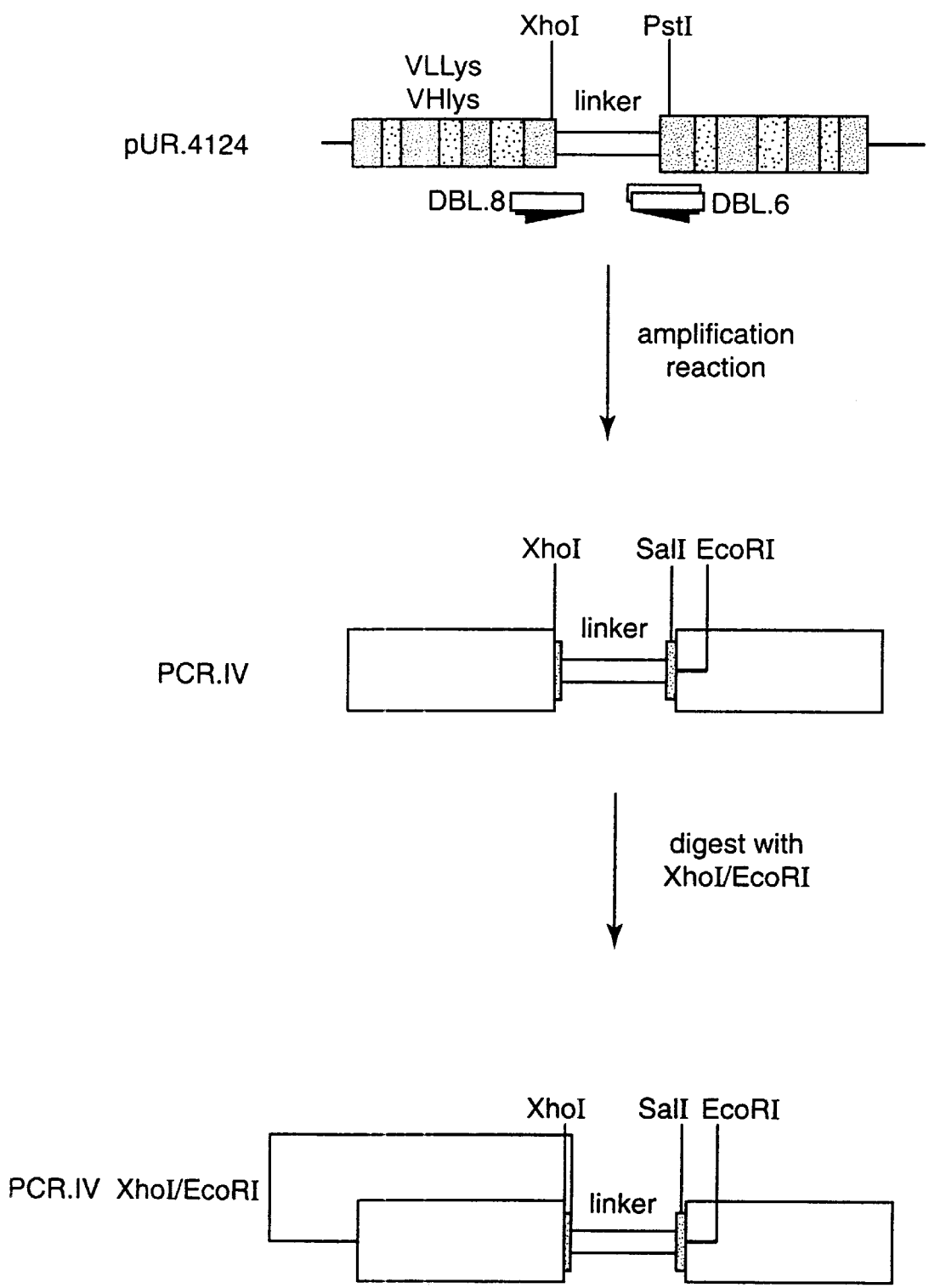
FIG. 23 shows the source of fragment PCR.IV XhoI/EcoRI.

This plasmid is derived from plasmid Fv.3418 (see FIG. 18). The XhoI-EcoRI fragment of plasmid Fv.3418 comprising the 3' end of DNA encoding framework-4 of the $V_L$ including the stop codon was removed and replaced by the fragment PCR-IV XhoI/EcoRI (FIG. 23). The oligonucleotides used to produce PCR-IV (DBL.8 and DBL.6, see Table 1) were designed to match the sequence at the junction of the $V_L$ and the $(Gly_4Ser)_3$ linker perfectly (DBL.8), and to be able to prime at the junction of the $(Gly_4Ser)_3$ linker and the $V_H$ in pUR.4124 (DBL.6). DBL.6 removed the PstI site in the $V_H$ (silent mutation) and introduced a SalI restriction site at the junction of the $(Gly_4Ser)_3$ linker and the $V_H$, thereby replacing the last Ser of the linker by a Val residue resulting in a $(Gly_4Ser)_2Gly_4Val$ linker (linkerV). Thus pGOSA.B can be indicated as:

pelB-$V_H$3418+pelB-$V_L$3418-linkerV-(SalI-EcoRI).

pGOSA.C

This plasmid contains DNA encoding $V_H$.4715 linked by the $(Gly_4Ser)_3$AlaGlySerAla linker to $V_H$.3418 (see FIG. 19), thus:

pelB-$V_H$4715-linkerA-$V_H$3418.

This construct was obtained by replacing the SfiI-EcoRI fragment from pGOSA.A encoding $V_L$.4715 by the fragment PCR-II SfiI/EcoRI containing the $V_H$.3418 gene. The oligonucleotides used to produce PCR-II (DBL.1 and DBL.2, see Table 1) hybridize in the framework-1 and framework-4 region of the gene encoding $V_H$.3418, respectively. DBL.1 was designed to remove the PstI restriction site (silent mutation) and to introduce an SfiI restriction site upstream of the $V_H$ gene. DBL.2 destroys the BstEII restriction site in the framework-4 region and introduces an NheI restriction site downstream of the stopcodon.

pGOSA.D

This plasmid contains a dicistronic operon comprising the $V_H$.3418 gene and DNA encoding $V_L$.3418 linked by the $(Gly_4Ser)_2Gly_4Val$ linker to $V_L$.4715 (see FIG. 20), thus:

pelB-$V_H$3418+peIB-$V_L$3418-linkerV-$V_L$4715.

Figure 24:
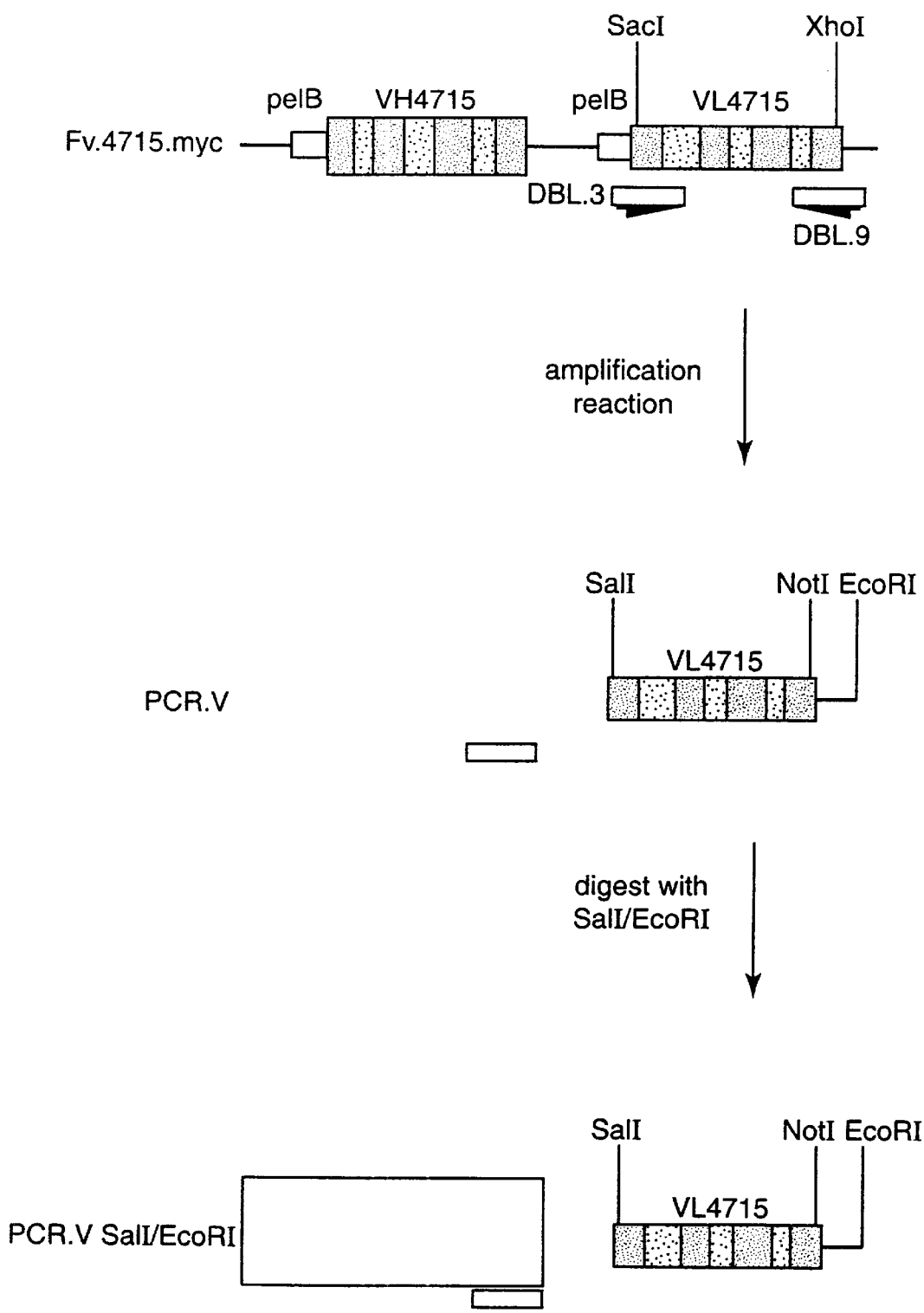
FIG. 24 shows the source of fragment PCR.V SalI/EcoRI.

This construct was obtained by digesting plasmid pGOSA.B with SalI-EcoRI and inserting the fragment PCR-V SalI/EcoRI (FIG. 24) containing the $V_L$.4715 gene. The oligonucleotides used to obtain PCR-V (DBL.3 and DBL.9, see Table 1) were designed to match the nucleotide sequence of the framework-1 and framework-4 regions of the $V_L$.4715 gene, respectively. DBL.3 removed the SacI site from the framework-1 region (silent mutation) and introduced a SalI restriction site upstream of the $V_L$.4715 gene. DBL.9 destroyed the XhoI restriction site in the framework-4 region of the $V_L$.4715 gene (silent mutation) and introduced a NotI and an EcoRI restriction site downstream of the stop codon.

pGOSA.E

This plasmid contains a dicistronic operon comprising DNA encoding $V_H$.4715 linked by the $(Gly_4Ser)$ ₃AlaGlySerAla linker to $V_H$.3418 plus DNA encoding $V_L$.3418 linked by the (Gly₄Ser)₂Gly₄Val linker to $V_L$.4715 (see FIG. 21), thus:

pelB-$V_H$4715-linkerA-$V_H$3418+pelB-$V_L$3418-linkerV-$V_L$4715.

Figure 25:
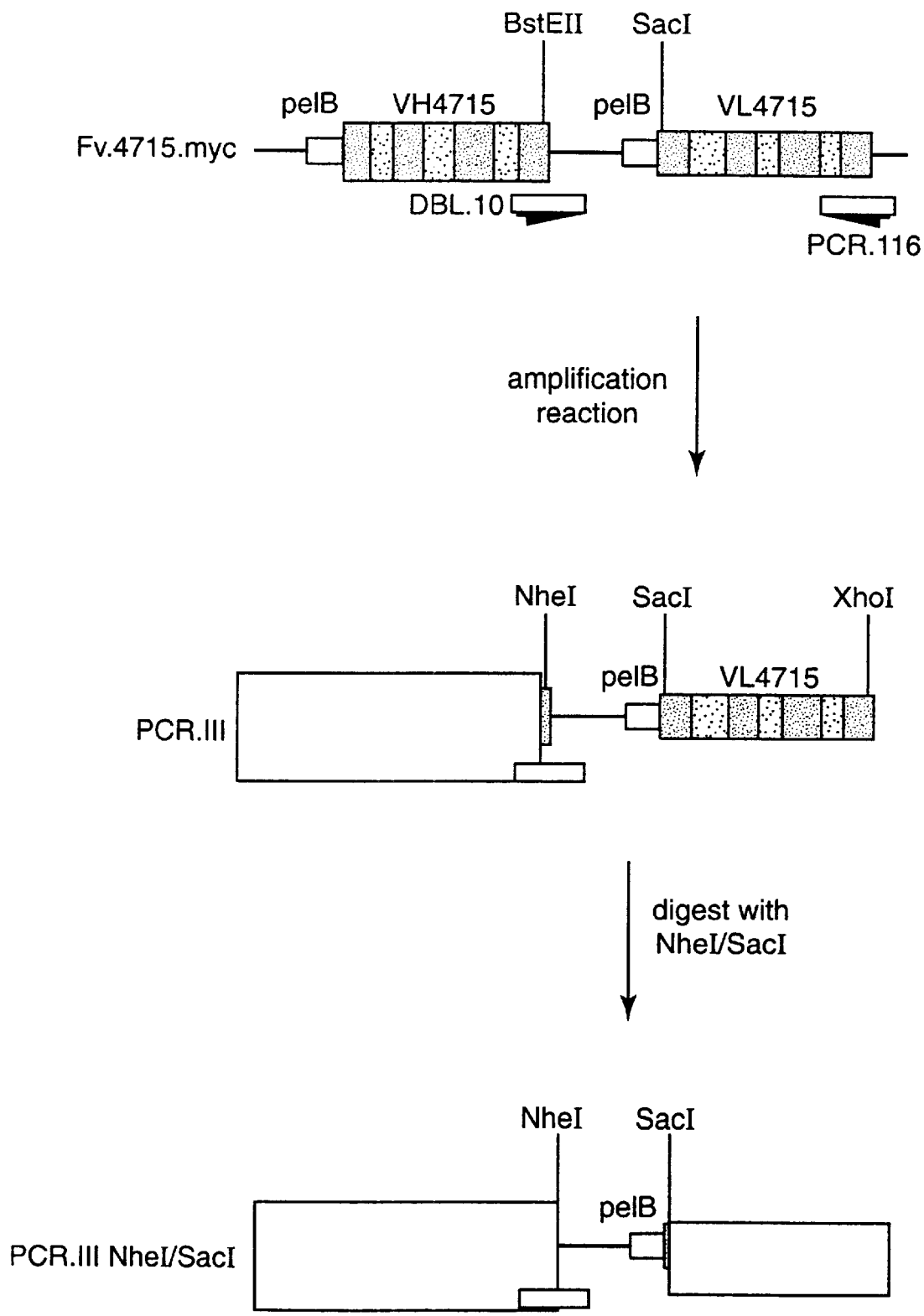
FIG. 25 shows the source of fragment PCR.III NheI/SacI.
Figure 26:
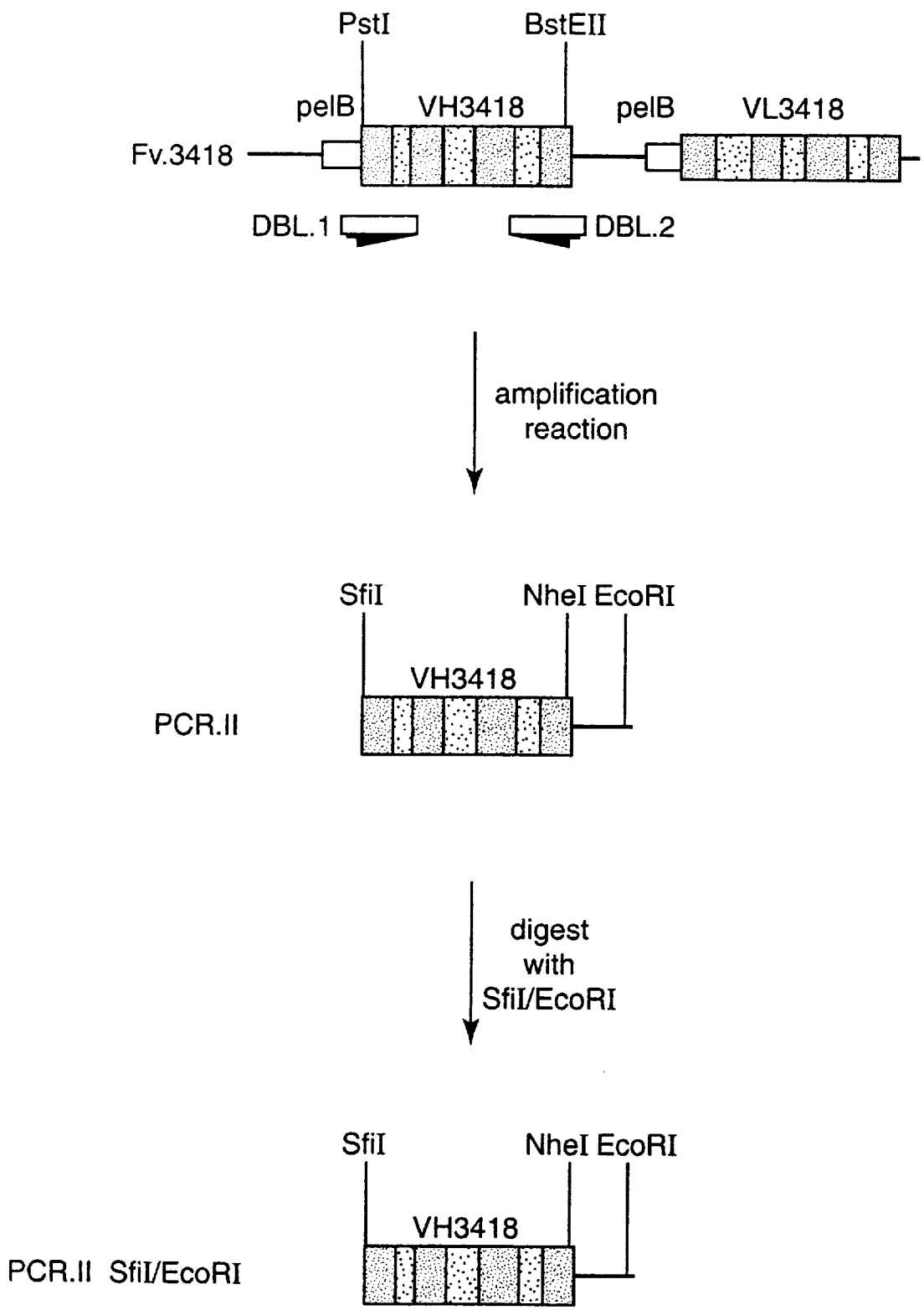
FIG. 26 shows the source of fragment PCR.II SfiI/EcoRI.

Both translational units are preceded by a ribosome binding site and DNA encoding a pelB leader sequence. This plasmid was obtained by a three-point ligation by mixing the vector resulting from pGOSA.D after removal of the $V_H$3418-encoding PstI-SacI insert with the PstI-NheI pGOSA.C insert containing $V_H$.4715 linked to $V_H$.3418 and the PCR-III NheI/SacI fragment (see FIG. 25). The remaining PstI-SacI PGOSA.D vector contains the 5' end of the framework-1 region of $V_H$.3418 up to the PstI restriction site and $V_L$.3418 linked by the (Gly₄Ser)₂Gly₄Val linker to $V_L$.4715 starting from the SacI restriction site in $V_L$.3418. The PstI-NheI pGOSA.C insert contains $V_H$.4715 linked by the (Gly₄Ser)₃AlaGlySerAla linker to $V_H$.3418, starting from the PstI restriction site in the framework-1 region in $V_H$.4715. The NheI-SacI PCR-III fragment provides the ribosome binding site and DNA encoding the pelB leader sequence for the $V_L$.3418-(Gly₄Ser)₂Gly₄Val-$V_L$.4715 construct. The oligonucleotides DBL.10 and PCR.116 (see Table 1) used to generate PCR-III were designed to match the sequence upstream of the ribosome binding site of $V_L$.4715 in Fv.4715 and to introduce an NheI restriction site (DEL.10), and to match the framework-4 region of $V_L$.3418 (PCR.116).

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
        (A) LENGTH: 1745 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
AAGCTTGCAT GGAAATTCTA TTTCAAGGAG ACAGTCATAA TGAAATACCT ATTGCCTACG      60

GCAGCCGCTG GATTGTTATT ACTCGCTGCC CAACCAGCGA TGGCCCAGGT GCAGCTGCAG     120

GAGTCAGGGG GAGACTTAGT GAAGCCTGGA GGGTCCCTGA CACTCTCCTG TGCAACCTCT     180

GGATTCACTT TCAGTAGTTA TGCCTTTTCT TGGGTCCGCC AGACCTCAGA CAAGAGTCTG     240

GAGTGGGTCG CAACCATCAG TAGTACTGAT ACTTATACCT ATTATTCAGA CAATGTGAAG     300

GGGCGCTTCA CCATCTCCAG AGACAATGGC AAGAACACCC TGTACCTGCA AATGAGCAGT     360

CTGAAGTCTG AGGACACAGC CGTGTATTAC TGTGCAAGAC ATGGGTACTA TGGTAAAGGC     420

TATTTTGACT ACTGGGGCCA AGGGACCACG GTCACCGTCT CCTCAGGTGG AGGCGGTTCA     480

GGCGGAGGTG GCTCTGGCGG TGGCGGATCG GCCGGTTCGG CCCAGGTCCA GCTGCAACAG     540

TCAGGACCTG AGCTGGTAAA GCCTGGGGCT TCAGTGAAGA TGTCCTGCAA GGCTTCTGGA     600

TACACATTCA CTAGCTATGT TATGCACTGG GTGAAACAGA AGCCTGGGCA GGGCCTTGAG     660

TGGATTGGAT ATATTTATCC TTACAATGAT GGTACTAAGT ACAATGAGAA GTTCAAAGGC     720

AAGGCCACAC TGACTTCAGA CAAATCCTCC AGCACAGCCT ACATGGAGCT CAGCAGCCTG     780

ACCTCTGAGG ACTCTGCGGT CTATTACTGT TCAAGCGCT TTGACTACTG GGGCCAAGGG     840

ACCACCGTCA CCGTCTCCTC ATAATAAGCT AGCGGAGCTG CATGCAAATT CTATTTCAAG     900

GAGACAGTCA TAATGAAATA CCTATTGCCT ACGGCAGCCG CTGGATTGTT ATTACTCGCT     960

GCCCAACCAG CGATGGCCGA CATCGAGCTC ACCCAGTCTC CATCTTCCAT GTATGCATCT    1020

CTAGGAGAGA GAATCACTAT CACTTGCAAG GCGAGTCAGG ACATTAATAC CTATTTAACC    1080

TGGTTCCAGC AGAAACCAGG GAAATCTCCC AAGACCCTGA TCTATCGTGC AAACAGATTG    1140

CTAGATGGGG TCCCATCAAG GTTCAGTGGC AGTGGATCTG GGCAAGATTA TTCTCTCACC    1200
```

-continued

```
ATCAGCAGCC TGGACTATGA AGATATGGGA ATTTATTATT GTCTACAATA TGATGAGTTG      1260

TACACGTTCG GAGGGGGGAC CAAGCTCGAG ATCAAACGGG GTGGAGGCGG TTCAGGCGGA      1320

GGTGGCTCTG GCGGTGGCGG AGTCGACATC GAACTCACTC AGTCTCCATT CTCCCTGACT      1380

GTGACAGCAG GAGAGAAGGT CACTATGAAT TGCAAGTCCG GTCAGAGTCT GTTAAACAGT      1440

GTAAATCAGA GGAACTACTT GACCTGGTAC CAGCAGAAGC CAGGGCAGCC TCCTAAACTG      1500

TTGATCTACT GGGCATCCAC TAGGGAATCT GGAGTCCCTG ATCGCTTCAC AGCCAGTGGA      1560

TCTGGAACAG ATTTCACTCT CACCATCAGC AGTGTGCAGG CTGAAGACCT GGCAGTTTAT      1620

TACTGTCAGA ATGATTATAC TTATCCGTTC ACGTTCGGAG GGGGGACCAA GCTCGAAATC      1680

AAACGGGGAT CCGGTAGCGG GAACTCCGGT AAGGGGTACC TGAAGTAATA AGCGGCCGCG      1740

AATTC                                                                 1745
```

(2) INFORMATION FOR SEQ ID NO: 2:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
AAGCTTGCAT GCAAATTCTA TTTCAAGGAG ACAGTCATAA TGAAATACCT ATTGCCTACG       60

GCAGCCGCTG GATTGTTATT ACTCGCTGCC CAACCAGCGA TGGCCCAGGT GCAGCTGCAG      120

GAGTCAGGAC CTGGCCTGGT GGCGCCCTCA CAGAGCCTGT CCATCACATG CACCGTCTCA      180

GGGTTCTCAT TAACCGGCTA TGGTGTAAAC TGGGTTCGCC AGCCTCCAGG AAAGGGTCTG      240

GAGTGGCTGG GAATGATTTG GGGTGATGGA AACACAGACT ATAATTCAGC TCTCAAATCC      300

AGACTGAGCA TCAGCAAGGA CAACTCCAAG AGCCAAGTTT TCTTAAAAAT GAACAGTCTG      360

CACACTGATG ACACAGCCAG GTACTACTGT GCCAGAGAGA GAGATTATAG GCTTGACTAC      420

TGGGGCGAAG GCACCACGGT CACCGTCTCC TCAGGTGGAG GCGGTTCAGG CGGAGGTGGC      480

TCTGGCGGTG GCGGATCGGA CATCGAGCTC ACCCAGTCTC CAGCCTCCCT TTCTGCGTCT      540

GTGGGAGAAA CTGTCACCAT CACATGTCGA GCAAGTGGGA ATATTCACAA TTATTTAGCA      600

TGGTATCAGC AGAAACAGGG AAAATCTCCT CAGCTCCTGG TCTATTATAC AACAACCTTA      660

GCAGATGGTG TGCCATCAAG GTTCAGTGGC AGTGGATCAG GAACACAATA TTCTCTCAAG      720

ATCAACAGCC TGCAACCTGA AGATTTTGGG AGTTATTACT GTCAACATTT TTGGAGTACT      780

CCTCGGACGT TCGGTGGAGG CACCAAGCTC GAGATCAAAC GGGAACAAAA ACTCATCTCA      840

GAAGAGGATC TGAATTAATA AGATCAAACG GTAATAAGGA TCCAGCTCGA ATTC           894
```

(2) INFORMATION FOR SEQ ID NO: 3:

(i) SEQUENCE CHARACTERISTICS:
        (A) LENGTH: 930 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
AAGCTTGCAT GCAAATTCTA TTTCAAGGAG ACAGTCATAA TGAAATACCT ATTGCCTACG       60

GCAGCCGCTG GATTGTTATT ACTCGCTGCC CAACCGGCCA TGGCCCAGGT GCAGCTGCAG      120
```

```
GAGTCAGGGG GAGACTTAGT GAAGCCTGGA GGGTCCCTGA CACTCTCCTG TGCAACCTCT      180

GGATTCACTT TCAGTAGTTA TGCCTTTTCT TGGGTCCGCC AGACCTCAGA CAAGAGTCTG      240

GAGTGGGTCG CAACCATCAG TAGTACTGAT ACTTATACCT ATTATTCAGA CAATGTGAAG      300

GGGCGCTTCA CCATCTCCAG AGACAATGGC AAGAACACCC TGTACCTGCA AATGAGCAGT      360

CTGAAGTCTG AGGACACAGC CGTGTATTAC TGTGCAAGAC ATGGGTACTA TGGTAAAGGC      420

TATTTTGACT ACTGGGGCCA AGGGACCACG GTCACCGTCT CCTCAGGTGG AGGCGGTTCA      480

GGCGGAGGTG GCTCTGGCGG TGGCGGATCG GACATCGAGC TCACTCAGTC TCCATTCTCC      540

CTGACTGTGA CAGCAGGAGA GAAGGTCACT ATGAATTGCA AGTCCGGTCA GAGTCTGTTA      600

AACAGTGTAA ATCAGAGGAA CTACTTGACC TGGTACCAGC AGAAGCCAGG GCAGCCTCCT      660

AAACTGTTGA TCTACTGGGC ATCCACTAGG GAATCTGGAG TCCCTGATCG CTTCACAGCC      720

AGTGGATCTG GAACAGATTT CACTCTCACC ATCAGCAGTG TGCAGGCTGA AGACCTGGCA      780

GTTTATTACT GTCAGAATGA TTATACTTAT CCGTTCACGT TCGGAGGGGG GACCAAGCTC      840

GAGATCAAAC GGGGATCCGG TAGCGGGAAC TCCGGTAAGG GGTACCTGAA GTAATAAGAT      900

CAAACGGTAA TAAGGATCCA GCTCGAATTC                                      930

(2) INFORMATION FOR SEQ ID NO: 4:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CCATGGGATG GAGCTGTATC ATCCTCTTCT TGGTAGCAAC AGCTACAGGT AAGGGGCTCA       60

CAGTAGCAGG CTTGAGGTCT GGACATATAT ATGGGTGACA ATGACATCCA CTTTGCCTTT      120

CTCTCCACAG GTGTCCACTC CCAGGTCCAA CTGCAG                               156

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

AGGTSMAMCT GCAGSAGTCW GG                                               22

(2) INFORMATION FOR SEQ ID NO: 6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TGAGGAGACG GTGACCGTGG TCCCTTGGCC CC                                    32
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GACATTGAGC TCACCCAGTC TCCA                                  24

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GTTAGATCTC GAGCTTGGTC CC                                    22

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CAGGATCCGG CCGGTTCGGC CCAGGTCCAG CTGCAACAGT CAGGA          45

(2) INFORMATION FOR SEQ ID NO: 10:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CTACATGAAT TCGCTAGCTT ATTATGAGGA GACGGTGACG GTGGTCCCTT GGC    53

(2) INFORMATION FOR SEQ ID NO: 11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

ATTGGAGTCG ACATCGAACT CACTCAGTCT CCATTCTCC                   39

(2) INFORMATION FOR SEQ ID NO: 12:

(i) SEQUENCE CHARACTERISTICS:
        (A) LENGTH: 36 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CGAATTCGGA TCCCCGTTTG ATTTCGAGCT TGGTCC                         36

(2) INFORMATION FOR SEQ ID NO: 13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GAGCGCGAGC TCGGCCGAAC CGGCCGATCC GCCACCGCCA GAGCC              45

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

ATTGTCGAAT TCGTCGACTC CGCCACCGCC AGAGCC                         36

(2) INFORMATION FOR SEQ ID NO: 15:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

AGCTTCTAGA CCACCATGGA AAACTGCAGA GCTCAAAAGC TAGCGCGGCG GCTCTAG   57

(2) INFORMATION FOR SEQ ID NO: 16:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

AATTCTAGAG CGGCCGCGCT AGCTTTTGAG CTCTGCAGTT TTCCATGGTG GTCTAGA   57

(2) INFORMATION FOR SEQ ID NO: 17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear

```
    (ii) MOLECULE TYPE: DNA (genomic)

(xi) SEQUENCE DESCRIPTION: SEQ ID NO: 17:

ACGGGTGAGC TCGATGTCGG AGTGGACACC TGTGGAGAGA                    40

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GGAAACAGCT ATGACCATGA TTAC                                     24

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(vii) IMMEDIATE SOURCE:
        (B) CLONE: primer DBL.7

(xi) SEQUENCE DESCRIPTION: SEQ ID NO: 19:

CACCATCTCC AGAGACAATG GCAAG                                    25

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(vii) IMMEDIATE SOURCE:
        (B) CLONE: primer DBL.8

(xi) SEQUENCE DESCRIPTION: SEQ ID NO: 20:

ACCAAGCTCG AGATCAAACG GGG                                      23

(2) INFORMATION FOR SEQ ID NO: 21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(vii) IMMEDIATE SOURCE:
        (B) CLONE: primer DBL.9

(xi) SEQUENCE DESCRIPTION: SEQ ID NO: 21:

TGAAGTGAAT TCGCGGCCGC TTATTACCGT TTGATTTCGA GCTTGGTCCC         50
```

(2) INFORMATION FOR SEQ ID NO: 22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(vii) IMMEDIATE SOURCE:
        (B) CLONE: primer DBL.10

(xi) SEQUENCE DESCRIPTION: SEQ ID NO: 22:

```
TAATAAGCTA GCGGAGCTGC ATGCAAATTC TATTTC                              36
```

(2) INFORMATION FOR SEQ ID NO: 23:

(i) SEQUENCE CHARACTERISTICS:
        (A) LENGTH: 737 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: EcoRI-HindIII insert of pUR4124

(ix) FEATURE:
        (A) NAME/KEY: CDS
        (B) LOCATION:11..730
        (D) OTHER INFORMATION:/product= "VLlys-GS-VHlys"

(ix) FEATURE:
        (A) NAME/KEY: mat_peptide
        (B) LOCATION:11..334
        (D) OTHER INFORMATION:/product= "VLlys"

(ix) FEATURE:
        (A) NAME/KEY: misc_RNA
        (B) LOCATION:335..379
        (D) OTHER INFORMATION:/product= "(Gly4Ser)3 linker"

(ix) FEATURE:
        (A) NAME/KEY: mat_peptide
        (B) LOCATION:380..727
        (D) OTHER INFORMATION:/product= "VHlys"

(xi) SEQUENCE DESCRIPTION: SEQ ID NO: 23:

```
GAATTCGGCC GAC ATC GAG CTC ACC CAG TCT CCA GCC TCC CTT TCT GCG      49
           Asp Ile Glu Leu Thr Gln Ser Pro Ala Ser Leu Ser Ala
             1               5                  10

TCT GTG GGA GAA ACT GTC ACC ATC ACA TGT CGA GCA AGT GGG AAT ATT     97
Ser Val Gly Glu Thr Val Thr Ile Thr Cys Arg Ala Ser Gly Asn Ile
 15              20                  25

CAC AAT TAT TTA GCA TGG TAT CAG CAG AAA CAG GGA AAA TCT CCT CAG    145
His Asn Tyr Leu Ala Trp Tyr Gln Gln Lys Gln Gly Lys Ser Pro Gln
 30              35                  40                  45

CTC CTG GTC TAT TAT ACA ACA ACC TTA GCA GAT GGT GTG CCA TCA AGG    193
Leu Leu Val Tyr Tyr Thr Thr Thr Leu Ala Asp Gly Val Pro Ser Arg
             50                  55                  60

TTC AGT GGC AGT GGA TCA GGA ACA CAA TAT TCT CTC AAG ATC AAC AGC    241
Phe Ser Gly Ser Gly Ser Gly Thr Gln Tyr Ser Leu Lys Ile Asn Ser
         65                  70                  75

CTG CAA CCT GAA GAT TTT GGG AGT TAT TAC TGT CAA CAT TTT TGG AGT    289
Leu Gln Pro Glu Asp Phe Gly Ser Tyr Tyr Cys Gln His Phe Trp Ser
             80                  85                  90
```

```
ACT CCT CGG ACG TTC GGT GGA GGG ACC AAG CTC GAG ATC AAA CGG GGT       337
Thr Pro Arg Thr Phe Gly Gly Gly Thr Lys Leu Glu Ile Lys Arg Gly
    95                  100                 105

GGA GGC GGT TCA GGC GGA GGT GGC TCT GGC GGT GGC GGA TCG CAG GTG       385
Gly Gly Gly Ser Gly Gly Gly Gly Ser Gly Gly Gly Gly Ser Gln Val
110             115                 120                 125

CAG CTG CAG GAG TCA GGA CCT GGC CTG GTG GCG CCC TCA CAG AGC CTG       433
Gln Leu Gln Glu Ser Gly Pro Gly Leu Val Ala Pro Ser Gln Ser Leu
                130                 135                 140

TCC ATC ACA TGC ACC GTC TCA GGG TTC TCA TTA ACC GGC TAT GGT GTA       481
Ser Ile Thr Cys Thr Val Ser Gly Phe Ser Leu Thr Gly Tyr Gly Val
            145                 150                 155

AAC TGG GTT CGC CAG CCT CCA GGA AAG GGT CTG GAG TGG CTG GGA ATG       529
Asn Trp Val Arg Gln Pro Pro Gly Lys Gly Leu Glu Trp Leu Gly Met
        160                 165                 170

ATT TGG GGT GAT GGA AAC ACA GAC TAT AAT TCA GCT CTC AAA TCC AGA       577
Ile Trp Gly Asp Gly Asn Thr Asp Tyr Asn Ser Ala Leu Lys Ser Arg
    175                 180                 185

CTG AGC ATC AGC AAG GAC AAC TCC AAG AGC CAA GTT TTC TTA AAA ATG       625
Leu Ser Ile Ser Lys Asp Asn Ser Lys Ser Gln Val Phe Leu Lys Met
190             195                 200                 205

AAC AGT CTG CAC ACT GAT GAC ACA GCC AGG TAC TAC TGT GCC AGA GAG       673
Asn Ser Leu His Thr Asp Asp Thr Ala Arg Tyr Tyr Cys Ala Arg Glu
                210                 215                 220

AGA GAT TAT AGG CTT GAC TAC TGG GGC CAA GGG ACC ACG GTC ACC GTC       721
Arg Asp Tyr Arg Leu Asp Tyr Trp Gly Gln Gly Thr Thr Val Thr Val
            225                 230                 235

TCC TCA TGA TAAGCTT                                                    737
Ser Ser *
        240
```

(2) INFORMATION FOR SEQ ID NO: 24:

(i) SEQUENCE CHARACTERISTICS:
        (A) LENGTH: 920 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert Fv.3418

(ix) FEATURE:
        (A) NAME/KEY: CDS
        (B) LOCATION:36..443
        (D) OTHER INFORMATION:/product= "pelB-VH3418"

(ix) FEATURE:
        (A) NAME/KEY: sig_peptide
        (B) LOCATION:36..101
        (D) OTHER INFORMATION:/product= "pectate lyase"

(ix) FEATURE:
        (A) NAME/KEY: mat_peptide
        (B) LOCATION:102..440
        (D) OTHER INFORMATION:/product= "VH3418"

(ix) FEATURE:
        (A) NAME/KEY: CDS
        (B) LOCATION:495..884
        (D) OTHER INFORMATION:/product= "pelB-VL4318"

(ix) FEATURE:
        (A) NAME/KEY: sig_peptide (B) LOCATION:495..560
        (D) OTHER INFORMATION:/product= "pectate lyase"

(ix) FEATURE:
        (A) NAME/KEY: mat_peptide
        (B) LOCATION:561..881
        (D) OTHER INFORMATION:/product= "VL3418"

(xi) SEQUENCE DESCRIPTION: SEQ ID NO: 24:

```
AAGCTTGCAA ATTCTATTTC AAGGAGACAG TCATA ATG AAA TAC CTA TTG CCT           53
                                      Met Lys Tyr Leu Leu Pro
                                      -22         -20

ACG GCA GCC GCT GGA TTG TTA TTA CTC GCT GCC CAA CCA GCG ATG GCC         101
Thr Ala Ala Ala Gly Leu Leu Leu Leu Ala Ala Gln Pro Ala Met Ala
    -15             -10                 -5

CAG GTG CAG CTG CAG CAG TCA GGA CCT GAG CTG GTA AAG CCT GGG GCT         149
Gln Val Gln Leu Gln Gln Ser Gly Pro Glu Leu Val Lys Pro Gly Ala
 1               5                  10                  15

TCA GTG AAG ATG TCC TGC AAG GCT TCT GGA TAC ACA TTC ACT AGC TAT         197
Ser Val Lys Met Ser Cys Lys Ala Ser Gly Tyr Thr Phe Thr Ser Tyr
                 20                  25                  30

GTT ATG CAC TGG GTG AAA CAG AAG CCT GGG CAG GGC CTT GAG TGG ATT         245
Val Met His Trp Val Lys Gln Lys Pro Gly Gln Gly Leu Glu Trp Ile
             35                  40                  45

GGA TAT ATT TAT CCT TAC AAT GAT GGT ACT AAG TAC AAT GAG AAG TTC         293
Gly Tyr Ile Tyr Pro Tyr Asn Asp Gly Thr Lys Tyr Asn Glu Lys Phe
 50                  55                  60

AAA GGC AAG GCC ACA CTG ACT TCA GAC AAA TCC TCC AGC ACA GCC TAC         341
Lys Gly Lys Ala Thr Leu Thr Ser Asp Lys Ser Ser Ser Thr Ala Tyr
 65                  70                  75                  80

ATG GAG CTC AGC AGC CTG ACC TCT GAG GAC TCT GCG GTC TAT TAC TGT         389
Met Glu Leu Ser Ser Leu Thr Ser Glu Asp Ser Ala Val Tyr Tyr Cys
                 85                  90                  95

TCA AGA CGC TTT GAC TAC TGG GGC CAA GGG ACC ACG GTC ACC GTC TCC         437
Ser Arg Arg Phe Asp Tyr Trp Gly Gln Gly Thr Thr Val Thr Val Ser
             100                 105                 110

TCA TAA TAAGAGCTAT GGGAGCTTGC ATGCAAATTC TATTTCAAGG AGACAGTCAT         493
Ser *
A ATG AAA TAC CTA TTG CCT ACG GCA GCC GCT GGA TTG TTA TTA CTC           539
  Met Lys Tyr Leu Leu Pro Thr Ala Ala Ala Gly Leu Leu Leu Leu
  -22         -20             -15                 -10

GCT GCC CAA CCA GCG ATG GCC GAC ATC GAG CTC ACC CAG TCT CCA TCT         587
Ala Ala Gln Pro Ala Met Ala Asp Ile Glu Leu Thr Gln Ser Pro Ser
         -5                   1                   5

TCC ATG TAT GCA TCT CTA GGA GAG AGA ATC ACT ATC ACT TGC AAG GCG         635
Ser Met Tyr Ala Ser Leu Gly Glu Arg Ile Thr Ile Thr Cys Lys Ala
 10                  15                  20                  25

AGT CAG GAC ATT AAT ACC TAT TTA ACC TGG TTC CAG CAG AAA CCA GGG         683
Ser Gln Asp Ile Asn Thr Tyr Leu Thr Trp Phe Gln Gln Lys Pro Gly
                 30                  35                  40

AAA TCT CCC AAG ACC CTG ATC TAT CGT GCA AAC AGA TTG CTA GAT GGG         731
Lys Ser Pro Lys Thr Leu Ile Tyr Arg Ala Asn Arg Leu Leu Asp Gly
             45                  50                  55

GTC CCA TCA AGG TTC AGT GGC AGT GGA TCT GGG CAA GAT TAT TCT CTC         779
Val Pro Ser Arg Phe Ser Gly Ser Gly Ser Gly Gln Asp Tyr Ser Leu
 60                  65                  70

ACC ATC AGC AGC CTG GAC TAT GAA GAT ATG GGA ATT TAT TAT TGT CTA         827
Thr Ile Ser Ser Leu Asp Tyr Glu Asp Met Gly Ile Tyr Tyr Cys Leu
             75                  80                  85

CAA TAT GAT GAG TTG TAC ACG TTC GGA GGG GGG ACC AAG CTC GAG ATC         875
Gln Tyr Asp Glu Leu Tyr Thr Phe Gly Gly Gly Thr Lys Leu Glu Ile
```

```
                90              95              100             105
AAA CGG TAA TAATGATCAA ACGGTATAAG GATCCAGCTC GAATTC              920
Lys Arg *
```

(2) INFORMATION FOR SEQ ID NO: 25:

(i) SEQUENCE CHARACTERISTICS:
        (A) LENGTH: 999 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of Fv.4715-myc (ix) FEATURE:
        (A) NAME/KEY: CDS
        (B) LOCATION:40..468
        (D) OTHER INFORMATION:/product= "pelB-VH4715"

(ix) FEATURE:
        (A) NAME/KEY: sig_peptide
        (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: CDS
        (B) LOCATION:520..963
        (D) OTHER INFORMATION:/product= "pelB-VL4715-myc"

(ix) FEATURE:
        (A) NAME/KEY: sig_peptide
        (B) LOCATION:520..585
        (D) OTHER INFORMATION:/product= "pectate lyase"

(ix) FEATURE:
        (A) NAME/KEY: mat_peptide
        (B) LOCATION:586..927
        (D) OTHER INFORMATION:/product= "VL4715"

(ix) FEATURE:
        (A) NAME/KEY: misc_RNA
        (B) LOCATION:928..960
        (D) OTHER INFORMATION:/product= "myc-tag"

(xi) SEQUENCE DESCRIPTION: SEQ ID NO: 25:

```
AAGCTTGCAT GCAAATTCTA TTTCAAGGAG ACAGTCATA ATG AAA TAC CTA TTG   54
                                           Met Lys Tyr Leu Leu
                                           -22         -20

CCT ACG GCA GCC GCT GGA TTG TTA TTA CTC GCT GCC CAA CCA GCG ATG  102
Pro Thr Ala Ala Ala Gly Leu Leu Leu Leu Ala Ala Gln Pro Ala Met
        -15                 -10                 -5

GCC CAG GTG CAG CTG CAG GAG TCA GGG GGA GAC TTA GTG AAG CCT GGA  150
Ala Gln Val Gln Leu Gln Glu Ser Gly Gly Asp Leu Val Lys Pro Gly
      1               5                  10                  15

GGG TCC CTG ACA CTC TCC TGT GCA ACC TCT GGA TTC ACT TTC AGT AGT  198
Gly Ser Leu Thr Leu Ser Cys Ala Thr Ser Gly Phe Thr Phe Ser Ser
              20                  25                  30

TAT GCC TTT TCT TGG GTC CGC CAG ACC TCA GAC AAG AGT CTG GAG TGG  246
Tyr Ala Phe Ser Trp Val Arg Gln Thr Ser Asp Lys Ser Leu Glu Trp
              35                  40                  45

GTC GCA ACC ATC AGT AGT ACT GAT ACT TAT ACC TAT TAT TCA GAC AAT  294
```

```
              Val Ala Thr Ile Ser Ser Thr Asp Thr Tyr Tyr Ser Asp Asn
                  50                  55                  60

GTG AAG GGG CGC TTC ACC ATC TCC AGA GAC AAT GGC AAG AAC ACC CTG           342
Val Lys Gly Arg Phe Thr Ile Ser Arg Asp Asn Gly Lys Asn Thr Leu
    65                  70                  75

TAC CTG CAA ATG AGC AGT CTG AAG TCT GAG GAC ACA GCC GTG TAT TAC           390
Tyr Leu Gln Met Ser Ser Leu Lys Ser Glu Asp Thr Ala Val Tyr Tyr
 80                  85                  90                  95

TGT GCA AGA CAT GGG TAC TAT GGT AAA GGC TAT TTT GAC TAC TGG GGC           438
Cys Ala Arg His Gly Tyr Tyr Gly Lys Gly Tyr Phe Asp Tyr Trp Gly
                 100                 105                 110

CAA GGG ACC ACG GTC ACC GTC TCC TCA TAA TAAGAGCTAT GGGAGCTTGC             488
Gln Gly Thr Thr Val Thr Val Ser Ser  *
             115                 120

ATGCAAATTC TATTTCAAGG AGACAGTCAT A ATG AAA TAC CTA TTG CCT ACG            540
                                  Met Lys Tyr Leu Leu Pro Thr
                                   -22         -20

GCA GCC GCT GGA TTG TTA TTA CTC GCT GCC CAA CCA GCG ATG GCC GAC           588
Ala Ala Ala Gly Leu Leu Leu Leu Ala Ala Gln Pro Ala Met Ala Asp
-15             -10                  -5                       1

ATC GAG CTC ACT CAG TCT CCA TTC TCC CTG ACT GTG ACA GCA GGA GAG           636
Ile Glu Leu Thr Gln Ser Pro Phe Ser Leu Thr Val Thr Ala Gly Glu
             5                   10                  15

AAG GTC ACT ATG AAT TGC AAG TCC GGT CAG AGT CTG TTA AAC AGT GTA           684
Lys Val Thr Met Asn Cys Lys Ser Gly Gln Ser Leu Leu Asn Ser Val
             20                  25                  30

AAT CAG AGG AAC TAC TTG ACC TGG TAC CAG CAG AAG CCA GGG CAG CCT           732
Asn Gln Arg Asn Tyr Leu Thr Trp Tyr Gln Gln Lys Pro Gly Gln Pro
 35                  40                  45

CCT AAA CTG TTG ATC TAC TGG GCA TCC ACT AGG GAA TCT GGA GTC CCT           780
Pro Lys Leu Leu Ile Tyr Trp Ala Ser Thr Arg Glu Ser Gly Val Pro
 50                  55                  60                  65

GAT CGC TTC ACA GCC AGT GGA TCT GGA ACA GAT TTC ACT CTC ACC ATC           828
Asp Arg Phe Thr Ala Ser Gly Ser Gly Thr Asp Phe Thr Leu Thr Ile
             70                  75                  80

AGC AGT GTG CAG GCT GAA GAC CTG GCA GTT TAT TAC TGT CAG AAT GAT           876
Ser Ser Val Gln Ala Glu Asp Leu Ala Val Tyr Tyr Cys Gln Asn Asp
             85                  90                  95

TAT ACT TAT CCG TTC ACG TTC GGA GGG GGG ACC AAG CTC GAG ATC AAA           924
Tyr Thr Tyr Pro Phe Thr Phe Gly Gly Gly Thr Lys Leu Glu Ile Lys
             100                 105                 110

CGG GAA CAA AAA CTC ATC TCA GAA GAG GAT CTG AAT TAA TAAGATCAAA            973
Arg Glu Gln Lys Leu Ile Ser Glu Glu Asp Leu Asn  *
 115                 120                 125

CGGTAATAAG GATCCAGCTC GAATTC                                              999
```

(2) INFORMATION FOR SEQ ID NO: 26:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of scFv.4715-myc (ix) FEATURE:
        (A) NAME/KEY: sig_peptide (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: misc_RNA
        (B) LOCATION:466..510
        (D) OTHER INFORMATION:/product= "(Gly4Ser)3-linker"

(ix) FEATURE:
        (A) NAME/KEY: mat_peptide
        (B) LOCATION:511..852
        (D) OTHER INFORMATION:/product= "VL4715"

(ix) FEATURE:
        (A) NAME/KEY: misc_RNA
        (B) LOCATION:853..885
        (D) OTHER INFORMATION:/product= "myc-tag"

(ix) FEATURE:
        (A) NAME/KEY: CDS
        (B) LOCATION:40..888
        (D) OTHER INFORMATION:/product=
            "pelB-VH4715-(Gly4Ser)3-VL4715-myc"

(xi) SEQUENCE DESCRIPTION: SEQ ID NO: 26:

```
AAGCTTGCAT GCAAATTCTA TTTCAAGGAG ACAGTCATA ATG AAA TAC CTA TTG          54
                                           Met Lys Tyr Leu Leu
                                           -22         -20

CCT ACG GCA GCC GCT GGA TTG TTA TTA CTC GCT GCC CAA CCA GCG ATG        102
Pro Thr Ala Ala Ala Gly Leu Leu Leu Leu Ala Ala Gln Pro Ala Met
        -15             -10              -5

GCC CAG GTG CAG CTG CAG GAG TCA GGG GGA GAC TTA GTG AAG CCT GGA        150
Ala Gln Val Gln Leu Gln Glu Ser Gly Gly Asp Leu Val Lys Pro Gly
 1           5                    10                      15

GGG TCC CTG ACA CTC TCC TGT GCA ACC TCT GGA TTC ACT TTC AGT AGT        198
Gly Ser Leu Thr Leu Ser Cys Ala Thr Ser Gly Phe Thr Phe Ser Ser
                20                  25                  30

TAT GCC TTT TCT TGG GTC CGC CAG ACC TCA GAC AAG AGT CTG GAG TGG        246
Tyr Ala Phe Ser Trp Val Arg Gln Thr Ser Asp Lys Ser Leu Glu Trp
            35                  40                  45

GTC GCA ACC ATC AGT AGT ACT GAT ACT TAT ACC TAT TAT TCA GAC AAT        294
Val Ala Thr Ile Ser Ser Thr Asp Thr Tyr Thr Tyr Tyr Ser Asp Asn
        50                  55                  60

GTG AAG GGG CGC TTC ACC ATC TCC AGA GAC AAT GGC AAG AAC ACC CTG        342
Val Lys Gly Arg Phe Thr Ile Ser Arg Asp Asn Gly Lys Asn Thr Leu
65                  70                  75

TAC CTG CAA ATG AGC AGT CTG AAG TCT GAG GAC ACA GCC GTG TAT TAC        390
Tyr Leu Gln Met Ser Ser Leu Lys Ser Glu Asp Thr Ala Val Tyr Tyr
 80                  85                  90                  95

TGT GCA AGA CAT GGG TAC TAT GGT AAA GGC TAT TTT GAC TAC TGG GGC        438
Cys Ala Arg His Gly Tyr Tyr Gly Lys Gly Tyr Phe Asp Tyr Trp Gly
                100                 105                 110

CAA GGG ACC ACG GTC ACC GTC TCC TCA GGT GGA GGC GGT TCA GGC GGA        486
Gln Gly Thr Thr Val Thr Val Ser Ser Gly Gly Gly Gly Ser Gly Gly
            115                 120                 125

GGT GGC TCT GGC GGT GGC GGA TCG GAC ATC GAG CTC ACT CAG TCT CCA        534
Gly Gly Ser Gly Gly Gly Gly Ser Asp Ile Glu Leu Thr Gln Ser Pro
        130                 135                 140

TTC TCC CTG ACT GTG ACA GCA GGA GAG AAG GTC ACT ATG AAT TGC AAG        582
Phe Ser Leu Thr Val Thr Ala Gly Glu Lys Val Thr Met Asn Cys Lys
    145                 150                 155
```

```
TCC GGT CAG AGT CTG TTA AAC AGT GTA AAT CAG AGG AAC TAC TTG ACC      630
Ser Gly Gln Ser Leu Leu Asn Ser Val Asn Gln Arg Asn Tyr Leu Thr
160             165                 170                 175

TGG TAC CAG CAG AAG CCA GGG CAG CCT CCT AAA CTG TTG ATC TAC TGG      678
Trp Tyr Gln Gln Lys Pro Gly Gln Pro Pro Lys Leu Leu Ile Tyr Trp
                180                 185                 190

GCA TCC ACT AGG GAA TCT GGA GTC CCT GAT CGC TTC ACA GCC AGT GGA      726
Ala Ser Thr Arg Glu Ser Gly Val Pro Asp Arg Phe Thr Ala Ser Gly
            195                 200                 205

TCT GGA ACA GAT TTC ACT CTC ACC ATC AGC AGT GTG CAG GCT GAA GAC      774
Ser Gly Thr Asp Phe Thr Leu Thr Ile Ser Ser Val Gln Ala Glu Asp
        210                 215                 220

CTG GCA GTT TAT TAC TGT CAG AAT GAT TAT ACT TAT CCG TTC ACG TTC      822
Leu Ala Val Tyr Tyr Cys Gln Asn Asp Tyr Thr Tyr Pro Phe Thr Phe
    225                 230                 235

GGA GGG GGG ACC AAG CTC GAG ATC AAA CGG GAA CAA AAA CTC ATC TCA      870
Gly Gly Gly Thr Lys Leu Glu Ile Lys Arg Glu Gln Lys Leu Ile Ser
240                 245                 250                 255

GAA GAG GAT CTG AAT TAA TAAGATCAAA CGGTAATAAG GATCCAGCTC GAATTC      924
Glu Glu Asp Leu Asn *
                260
```

(2) INFORMATION FOR SEQ ID NO: 27:

(i) SEQUENCE CHARACTERISTICS:
        (A) LENGTH: 1706 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "cDNA domains with synthetic
            linker(s)"

(vii) IMMEDIATE SOURCE:
        (B) CLONE: HindIII-EcoRI insert of pGOSA.E (ix) FEATURE:
        (A) NAME/KEY: CDS
        (B) LOCATION:40..864
        (D) OTHER INFORMATION:/product= "pelB-VH4715-LiA-VH3418"

(ix) FEATURE:
        (A) NAME/KEY: sig_peptide
        (B) LOCATION:40..105
        (D) OTHER INFORMATION:/product= "pectate lyase"

(ix) FEATURE:
        (A) NAME/KEY: mat_peptide
        (B) LOCATION:106..465
        (D) OTHER INFORMATION:/product= "VH4715"

(ix) FEATURE:
        (A) NAME/KEY: misc_RNA
        (B) LOCATION:466..522
        (D) OTHER INFORMATION:/product= "linkerA
            (Gly4Ser)3AlaGlySerAla"

(ix) FEATURE:
        (A) NAME/KEY: mat_peptide
        (B) LOCATION:523..861
        (D) OTHER INFORMATION:/product= "VH3418"

(ix) FEATURE:
        (A) NAME/KEY: CDS
        (B) LOCATION:913..1689
        (D) OTHER INFORMATION:/product= "pelB-VL3418-LiV-VL4715"

(ix) FEATURE:
        (A) NAME/KEY: sig_peptide
        (B) LOCATION:913..978
        (D) OTHER INFORMATION:/product= "pectate lyase"

-continued (ix) FEATURE:
(A) NAME/KEY: mat_peptide
(B) LOCATION:979..1299
(D) OTHER INFORMATION:/product= "VL3418"

(ix) FEATURE:
(A) NAME/KEY: misc_RNA
(B) LOCATION:1300..1344
(D) OTHER INFORMATION:/product= "linker V
(Gly4Ser)2Gly4Val"

(ix) FEATURE:
(A) NAME/KEY: mat_peptide
(B) LOCATION:1345..1686
(D) OTHER INFORMATION:/product= "VL4715"

(xi) SEQUENCE DESCRIPTION: SEQ ID NO: 27:

```
AAGCTTGCAT GGAAATTCTA TTTCAAGGAG ACAGTCATA ATG AAA TAC CTA TTG                54
                                           Met Lys Tyr Leu Leu
                                           -22         -20

CCT ACG GCA GCC GCT GGA TTG TTA TTA CTC GCT GCA CAA CCA GCG ATG               102
Pro Thr Ala Ala Ala Gly Leu Leu Leu Leu Ala Ala Gln Pro Ala Met
        -15                 -10                 -5

GCC CAG GTG CAG CTG CAG GAG TCA GGG GGA GAC TTA GTG AAG CCT GGA               150
Ala Gln Val Gln Leu Gln Glu Ser Gly Gly Asp Leu Val Lys Pro Gly
    1               5                   10                  15

GGG TCC CTG ACA CTC TCC TGT GCA ACC TCT GGA TTC ACT TTC AGT AGT               198
Gly Ser Leu Thr Leu Ser Cys Ala Thr Ser Gly Phe Thr Phe Ser Ser
                20                  25                  30

TAT GCC TTT TCT TGG GTC CGC CAG ACC TCA GAC AAG AGT CTG GAG TGG               246
Tyr Ala Phe Ser Trp Val Arg Gln Thr Ser Asp Lys Ser Leu Glu Trp
            35                  40                  45

GTC GCA ACC ATC AGT AGT ACT GAT ACT TAT ACC TAT TAT TCA GAC AAT               294
Val Ala Thr Ile Ser Ser Thr Asp Thr Tyr Thr Tyr Tyr Ser Asp Asn
        50                  55                  60

GTG AAG GGG CGC TTC ACC ATC TCC AGA GAC AAT GGC AAG AAC ACC CTG               342
Val Lys Gly Arg Phe Thr Ile Ser Arg Asp Asn Gly Lys Asn Thr Leu
    65                  70                  75

TAC CTG CAA ATG AGC AGT CTG AAG TCT GAG GAC ACA GCC GTG TAT TAC               390
Tyr Leu Gln Met Ser Ser Leu Lys Ser Glu Asp Thr Ala Val Tyr Tyr
80                  85                  90                  95

TGT GCA AGA CAT GGG TAC TAT GGT AAA GGC TAT TTT GAC TAC TGG GGC               438
Cys Ala Arg His Gly Tyr Tyr Gly Lys Gly Tyr Phe Asp Tyr Trp Gly
                100                 105                 110

CAA GGG ACC ACG GTC ACC GTC TCC TCA GGT GGA GGC GGT TCA GGC GGA               486
Gln Gly Thr Thr Val Thr Val Ser Ser Gly Gly Gly Gly Ser Gly Gly
            115                 120                 125

GGT GGC TCT GGC GGT GGC GGA TCG GCC GGT TCG GCC CAG GTC CAG CTG               534
Gly Gly Ser Gly Gly Gly Gly Ser Ala Gly Ser Ala Gln Val Gln Leu
        130                 135                 140

CAA CAG TCA GGA CCT GAG CTG GTA AAG CCT GGG GCT TCA GTG AAG ATG               582
Gln Gln Ser Gly Pro Glu Leu Val Lys Pro Gly Ala Ser Val Lys Met
    145                 150                 155

TCC TGC AAG GCT TCT GGA TAC ACA TTC ACT AGC TAT GTT ATG CAC TGG               630
Ser Cys Lys Ala Ser Gly Tyr Thr Phe Thr Ser Tyr Val Met His Trp
160                 165                 170                 175

GTG AAA CAG AAG CCT GGG CAG GGC CTT GAG TGG ATT GGA TAT ATT TAT               678
Val Lys Gln Lys Pro Gly Gln Gly Leu Glu Trp Ile Gly Tyr Ile Tyr
                180                 185                 190

CCT TAC AAT GAT GGT ACT AAG TAC AAT GAG AAG TTC AAA GGC AAG GCC               726
Pro Tyr Asn Asp Gly Thr Lys Tyr Asn Glu Lys Phe Lys Gly Lys Ala
            195                 200                 205
```

```
ACA CTG ACT TCA GAC AAA TCC TCC AGC ACA GCC TAC ATG GAG CTC AGC      774
Thr Leu Thr Ser Asp Lys Ser Ser Ser Thr Ala Tyr Met Glu Leu Ser
        210                 215                 220

AGC CTG ACC TCT GAG GAC TCT GCG GTC TAT TAC TGT TCA AGA CGC TTT      822
Ser Leu Thr Ser Glu Asp Ser Ala Val Tyr Tyr Cys Ser Arg Arg Phe
225                 230                 235

GAC TAC TGG GGC CAA GGG ACC ACC GTC ACC GTC TCC TCA TAA              864
Asp Tyr Trp Gly Gln Gly Thr Thr Val Thr Val Ser Ser  *
240                 245                 250

TAAGCTAGCG GAGCTGCATG CAAATTCTAT TTCAAGGAGA CAGTCATA ATG AAA TAC     921
                                                    Met Lys Tyr
                                                    -22     -20

CTA TTG CCT ACG GCA GCC GCT GGA TTG TTA TTA CTC GCT GCC CAA CCA      969
Leu Leu Pro Thr Ala Ala Ala Gly Leu Leu Leu Leu Ala Ala Gln Pro
            -15                 -10                 -5

GCG ATG GCC GAC ATC GAG CTC ACC CAG TCT CCA TCT TCC ATG TAT GCA     1017
Ala Met Ala Asp Ile Glu Leu Thr Gln Ser Pro Ser Ser Met Tyr Ala
            1               5                   10

TCT CTA GGA GAG AGA ATC ACT ATC ACT TGC AAG GCG AGT CAG GAC ATT     1065
Ser Leu Gly Glu Arg Ile Thr Ile Thr Cys Lys Ala Ser Gln Asp Ile
        15                  20                  25

AAT ACC TAT TTA ACC TGG TTC CAG CAG AAA CCA GGG AAA TCT CCC AAG     1113
Asn Thr Tyr Leu Thr Trp Phe Gln Gln Lys Pro Gly Lys Ser Pro Lys
30                  35                  40                  45

ACC CTG ATC TAT CGT GCA AAC AGA TTG CTA GAT GGG GTC CCA TCA AGG     1161
Thr Leu Ile Tyr Arg Ala Asn Arg Leu Leu Asp Gly Val Pro Ser Arg
                50                  55                  60

TTC AGT GGC AGT GGA TCT GGG CAA GAT TAT TCT CTC ACC ATC AGC AGC     1209
Phe Ser Gly Ser Gly Ser Gly Gln Asp Tyr Ser Leu Thr Ile Ser Ser
            65                  70                  75

CTG GAC TAT GAA GAT ATG GGA ATT TAT TAT TGT CTA CAA TAT GAT GAG     1257
Leu Asp Tyr Glu Asp Met Gly Ile Tyr Tyr Cys Leu Gln Tyr Asp Glu
        80                  85                  90

TTG TAC ACG TTC GGA GGG GGG ACC AAG CTC GAG ATC AAA CGG GGT GGA     1305
Leu Tyr Thr Phe Gly Gly Gly Thr Lys Leu Glu Ile Lys Arg Gly Gly
    95                  100                 105

GGC GGT TCA GGC GGA GGT GGC TCT GGC GGT GGC GGA GTC GAC ATC GAA     1353
Gly Gly Ser Gly Gly Gly Gly Ser Gly Gly Gly Gly Val Asp Ile Glu
110             115                 120                     125

CTC ACT CAG TCT CCA TTC TCC CTG ACT GTG ACA GCA GGA GAG AAG GTC     1401
Leu Thr Gln Ser Pro Phe Ser Leu Thr Val Thr Ala Gly Glu Lys Val
            130                 135                 140

ACT ATG AAT TGC AAG TCC GGT CAG AGT CTG TTA AAC AGT GTA AAT CAG     1449
Thr Met Asn Cys Lys Ser Gly Gln Ser Leu Leu Asn Ser Val Asn Gln
            145                 150                 155

AGG AAC TAC TTG ACC TGG TAC CAG CAG AAG CCA GGG CAG CCT CCT AAA     1497
Arg Asn Tyr Leu Thr Trp Tyr Gln Gln Lys Pro Gly Gln Pro Pro Lys
            160                 165                 170

CTG TTG ATC TAC TGG GCA TCC ACT AGG GAA TCT GGA GTC CCT GAT CGC     1545
Leu Leu Ile Tyr Trp Ala Ser Thr Arg Glu Ser Gly Val Pro Asp Arg
        175                 180                 185

TTC ACA GCC AGT GGA TCT GGA ACA GAT TTC ACT CTC ACC ATC AGC AGT     1593
Phe Thr Ala Ser Gly Ser Gly Thr Asp Phe Thr Leu Thr Ile Ser Ser
190                 195                 200                 205

GTG CAG GCT GAA GAC CTG GCA GTT TAT TAC TGT CAG AAT GAT TAT ACT     1641
Val Gln Ala Glu Asp Leu Ala Val Tyr Tyr Cys Gln Asn Asp Tyr Thr
        210                 215                 220
```

-continued

```
TAT CCG TTC ACG TTC GGA GGG GGG ACC AAG CTC GAA ATC AAA CGG TAA      1689
Tyr Pro Phe Thr Phe Gly Gly Gly Thr Lys Leu Glu Ile Lys Arg  *
            225                 230                 235

TAAGCGGCCG CGAATTC                                                    1706
```

What is claimed is:

1. A multivalent antigen binding protein comprising:
   a first polypeptide comprising, in series, three or more variable domains of an antibody heavy chain; and
   a second polypeptide comprising, in series, three or more variable domains of an antibody light chain,
   said first and second polypeptides being linked by association of the respective heavy chain and light chain variable domains, each associated variable domain pair forming an antigen binding site.

2. A protein according to claim 1 comprising a trivalent antigen binding protein.

3. A protein according to claim 1 or claim 2 wherein the variable domains of the antibody heavy chain of said first polypeptide are linked by a peptide linker and the variable domains of the antibody light chain of said second polypeptide are linked by a peptide linker.

4. A protein according to any one of claims 1 to 3 wherein the associated variable domain pair binding sites are able to bind different epitopes from each other.

5. A protein according to any one of claims 1 to 3 wherein the associated variable domain pair binding sites are able to bind the same epitope as each other.

6. A process for preparing a multivalent antigen binding protein according to any one of claims 1 to 5 comprising
   (i) transforming one or more hosts by incorporating genes encoding said first and second polypeptides;
   (ii) expressing said genes and said host or hosts; and
   (iii) allowing said first and second polypeptides to associate to form the protein.

7. A protein according to any one of claims 1 to 5 for use in medicine.

8. A diagnostic or therapeutic composition comprising a protein according to any one of claims 1 to 5.

9. A method of diagnosis or therapy comprising administering a protein according to any one of claims 1 to 5.

10. A method of preparing an agent for diagnosis or therapy comprising combining a composition according to claim 8 with at least one suitable pharmaceutical carrier or excipient.

11. A method for immunoassay or purification comprising contacting a composition according to one of claims 1 to 5 with a test sample.

* * * * *